(12) United States Patent
Rezaei-Araghi et al.

(10) Patent No.: US 11,142,554 B2
(45) Date of Patent: Oct. 12, 2021

(54) SELECTIVE MCL-1 BINDING PEPTIDES

(71) Applicants: MASSACHUSETTS INSTITUTE OF TECHNOLOGY, Cambridge, MA (US); Dana-Farber Cancer Institute, Inc., Boston, MA (US)

(72) Inventors: Raheleh Rezaei-Araghi, Brookline, MA (US); Amy Keating, Arlington, MA (US); Gregory H. Bird, Pelham, NH (US); Loren Walensky, Pelham, MA (US)

(73) Assignees: MASSACHUSETTS INSTITUTE OF TECHNOLOGY, Cambridge, MA (US); Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 15/558,443

(22) PCT Filed: Mar. 18, 2016

(86) PCT No.: PCT/US2016/023118
§ 371 (c)(1),
(2) Date: Sep. 14, 2017

(87) PCT Pub. No.: WO2016/149613
PCT Pub. Date: Sep. 22, 2016

(65) Prior Publication Data
US 2018/0201658 A1    Jul. 19, 2018

Related U.S. Application Data

(60) Provisional application No. 62/134,904, filed on Mar. 18, 2015.

(51) Int. Cl.
A61K 38/16    (2006.01)
A61K 38/00    (2006.01)
C07K 14/47    (2006.01)

(52) U.S. Cl.
CPC .......... C07K 14/4702 (2013.01); A61K 38/16 (2013.01); A61K 38/00 (2013.01)

(58) Field of Classification Search
None
See application file for complete search history.

(56) References Cited

U.S. PATENT DOCUMENTS

| | | |
|---|---|---|
| 5,446,090 A | 8/1995 | Harris |
| 6,348,558 B1 | 2/2002 | Harris et al. |
| 7,723,468 B2 | 5/2010 | Daffre et al. |
| 8,889,632 B2 | 11/2014 | Bernal et al. |
| 2004/0067503 A1 | 4/2004 | Tan et al. |
| 2005/0250680 A1 | 11/2005 | Walensky et al. |
| 2008/0027145 A1 | 1/2008 | Huang |
| 2008/0199890 A1 | 8/2008 | Letai |
| 2009/0092582 A1 | 4/2009 | Bogin et al. |
| 2009/0275519 A1 | 11/2009 | Nash et al. |
| 2010/0273704 A1 | 10/2010 | Korsmeyer et al. |
| 2010/0286057 A1 | 11/2010 | Walensky et al. |
| 2012/0172285 A1 | 7/2012 | Walensky et al. |
| 2014/0363434 A1 | 12/2014 | Lasters et al. |
| 2015/0045310 A1 | 2/2015 | Link et al. |
| 2016/0095315 A1 | 4/2016 | Wei et al. |
| 2018/0128813 A1 | 5/2018 | Letai et al. |

FOREIGN PATENT DOCUMENTS

| | | |
|---|---|---|
| WO | WO1999/014259 | 3/1999 |
| WO | WO1999/034833 | 7/1999 |
| WO | WO2006/135985 | 12/2006 |
| WO | WO2008/121767 | 10/2008 |
| WO | WO2010/060112 | 5/2010 |
| WO | WO2010/068684 | 6/2010 |
| WO | WO2010/148335 | 12/2010 |
| WO | WO2013/116829 | 8/2013 |

OTHER PUBLICATIONS

Okamoto, T., et al., Stabilizing the pro-apoptotic BimBH3 helix (BimSAHB) does not necessarily enhance affinity or biological activity, ACS Chem Biol Feb. 15, 2013;8(2):297-302 (Year: 2013).*
International Search Report and Written Opinion dated Sep. 23, 2016 in international application No. PCT/US2016/023118, 17 pgs.
Altschul et al., "Gapped BLAST and PSI-BLAST: a new generation of protein database search programs", Nucleic Acids Res., 25: 3389-3402, 1997.
Blackwell et al., "Highly Efficient Synthesis of Covalently Cross-Linked Peptide Helices by Ring-Closing Metathesis", Angew Chem. Int. Ed. 37: 3281, 1994.
Araghi et al., "Rapid Optimization of Mcl-1 Inhibitors using Stapled Peptide Libraries Including Non-Natural Side Chains", ACS Chem. Biol., Epub, 19, 11(5):1238-44; p. 1239, Table 1, 2016.
Armstrong et al., "The (i, i+4) Phe-His Interaction Studied in an Alanine-based (X-Helix", J. Mol. Biol., 230(1), 284, 1993.
Bird et al., "Chemical Synthesis of Hydrocarbon-Stapled Peptides for Protein Interaction Research and Therapeutic Targeting", Current Protocols in Chemical Biology, 99-117, 2011.
Bird et al., "Synthesis and Biophysical Characterization of Stabilized a-Helices of BCL-2 Domains", Methods in Enzymol., 446:369-386, 2008.
Blackwell et al., "Ring-Closing Metathesis of Olefinic Peptides: Design, Synthesis, and Structural Characterization of Macrocyclic Helical Peptides", J. Org. Chem., 66: 5291-5302, 2001.
Boersma et al., "Hydrophile scanning as a complement to alanine scanning for exploring and manipulating protein-protein recognition: Application to the Bim BH3 domain", Protein Sci., 2008, 17(7), 1232.

(Continued)

Primary Examiner — Thomas S Heard
(74) Attorney, Agent, or Firm — Fish & Richardson P.C.

(57) ABSTRACT

Provided herein are stabilized peptides that bind Mcl-1. Also provided are compositions containing these polypeptides and methods of using such peptides in the treatment of cancer that include administering to a subject one of the polypeptides.

16 Claims, 15 Drawing Sheets

Specification includes a Sequence Listing.

(56) References Cited

OTHER PUBLICATIONS

Burke et al., "Discovery of Try cyclic Indoles that Potently Inhibit Mcl-1 using Fragment-Based Methods and Structure-Based Design", J. Med. Chem., 2015, 58(9), 3794.
Bumelle et al., "MCL-1-dependent leukemia cells are more sensitive to chemotherapy than BCL-2-dependent counterparts", J. Cell. Biol., 2009, 187(3),429.
Deng et al., "BH3 Profiling Identifies Three Distinct Classes of Apoptotic Blocks to Predict Response to ABT-737 and Conventional Chemotherapeutic Agents", Cancer Cell, 12(2), 171, 2015.
Devi et al., "Antibodies to poly[(2-*)-a-N-acetylneuraminicacid] and poly [(2-9)-a-N-acetylneuraminic acid] are elicited by immunization of mice with *Escherichia coli* k92 conjugates: Potential vaccines for groups B and C meningococci and *E. coli* K1", Proc. Natl. Acad. Sci. USA 88:7175-7179, 1991.
Dutta et al., "Determinants of BH3 binding specificity for Mcl-1 vs. Bcl-x", J. Mol. Biol. 2010, 398(5), 747.
Fattom et al., "Serum Antibody Response in Adult Volunteers Elicited by Injection of *Streptococcus pneumoniae* Type 12F Polysaccharide Alone or Conjugated to Diphtheria Toxoid", Infect. Immun., 58:2309-2312, 1990.
Foight et al., "Designed BH3 Peptides with High Affinity and Specificity for Targeting Mcl-1 in Cells", ACS Chem. Biol., 2014, 9(9), pp. 1962-1968.
International Search Report in International Application No. PCT/US2016/059320, dated May 22, 2017, 5 pages.
Kawamoto et al., "Design of Triazole-stapled BCL9 a-Helical Peptides to Target the B-Catenin/B-cell CLL/lymphoma 9 (BCL9) Protein-Protein Interaction", Journal of Medicinal Chemistry 55:1137-1146, 2012.
Kim et al., "Synthesis of all-hydrocarbon stapled a-helical peptides by ring-closing olefin metathesis", Nat. Protoc., 6(6), 761, 2011.
Kritzer, "Stapled Peptides: Magic bullets in nature's arsenal", Nature Chemical Biology, Aug. 1, 2010, vol. 6, No. 8, pp. 566-567.
Ryan et al., "BH3 Profiling in Whole Cells by Fluorimeter or FACS", Methods 2013, 61(2), 156.
Ryan et al., "Heightened mitochondiral priming is the basus for apoptotic hypersensitivity of CD4+ CD8+ thymocytes", Proc. Natl. Acad. Sci., 2010, 107(29), 12895.
Schafmiester et al., "An All-Hydrocarbon Cross-Linking System for Enhancing the Helicity and Metabolic Stability of Peptides", J. Am Chem. Soc., 122: 5891-5892, 2000.
Stewart et al., "The MCL-1 BH3 Helix is an Exclusive MCL-1 inhibitor and Apoptosis Sensitizer", Nat. Chem. Biol., 2010, 6(8),595.
Szu et al., "Comparative Immunogenicities of Vi Polysaccharide-Protein Conjugates Composed of Cholera Toxin or Its B Subunit as a Carrier Bound to High- or Lower-Molecular-Weight Vi", Infect. Immun., 57:3823-3827, 1989.
Szu et al., "Laboratory and Preliminary Clinical Characterization of Vi Capsular Polysaccharide-Protein Conjugate Vaccines", Infect. Immun,, 62:4440-4444, 1994.
Szu et al., "Relation between Structure and Immunologic Properties of the Vi Capsular Polysaccharide", Infect. Immun. 59:4555-4561, 1991.
Szu et al., "Vi Capsular Polysaccharide-Protein Conjugates for Prevention of Typhoid Fever", J. Exp. Med., 166:1510-1524, 1987.
Walensky et al., "Activation of Apoptosis in Vivo by a Hydrocarbon-Stapled BH3 Helix", Science, 305:1466-1470, 2004.
Wilen et al., "Strategies in Optical Resolutions", Tetrahedron 33:2725, 1977.
Wilen et al., "Tales of Resolving Agents and Optical Resolutions", p. 268, University of Notre Dame Press,1972.
Williams et al., "Asymmetric Synthesis of Monosubstituted and a, a-Disubstituted -Amino Acids via Diastereoselective Glycine Enolate Alkylations", J. Am. Chem. Soc., 113: 9276, 1991.
Williams et al., "Efficient Asymmetric Synthesis of N-tert-Butoxycarbonyl □-Aminoacids Using 4-tert-Butoxycarbonyl-5,6-Diphenylmorpholin-2-One: (R)-(Ntert-Butoxycarbonyl)Allylglycine [(4-Pentenoic acid, 2-[[(1,1-dimethylethoxy)carbonyl]amino]-, (2R)-)]", Org. Synth., 80:31, 2003.
Xiao et al., "Immobilized OBOC combinatorial bead array to facilitate multiplicative screening", Comb. Chem. High Throughput Screen, 2013, 16(6), 441.
European Supplementary Search Report in Appln. No. EP16765822, dated Jul. 24, 2018, 22 pages.
International Search Report in International Application No. PCT/US2013/24617, dated May 20, 2013, 3 pages.
Adams et al., "Measuring the sequence-affinity landscape of antibodies with massively parallel titration curves," eLife, Dec. 30, 2016, 5, e23156.
Alford et al., "The Rosetta All-Atom Energy Function for Macromolecular Modeling and Design," Journal of Chemical Theory and Computation, Jun. 13, 2017, 13(6), 3031-3048.
Arkadash et al., "Development of High Affinity and High Specificity Inhibitors of Matrix Metalloproteinase 14 through Computational Design and Directed Evolution," Journal of Biological Chemistry, Jan. 13, 2017, 292(8), 3481-3495.
Arkin et al., (2014). "Small-Molecule Inhibitors of Protein-Protein Interactions: Progressing toward the Reality," Chemistry & Biology, Sep. 18, 2014, 21(9), 1102-1114.
Bechara et al., "Cell-penetrating peptides: 20 years later, where do we stand?," FEBS Lett., Jun. 19, 2013, 587(12):1693-1702.
Bedbrook et al., "Machine learning to design integral membrane channelrhodopsins for efficient eukaryotic expression and plasma membrane localization," PLOS Computational Biology, Oct. 23, 2017, 13(10), e1005786.
Berger et al., "Computationally designed high specificity inhibitors delineate the roles of BCL2 family proteins in cancer," eLife, Nov. 2, 2016, 5, 1422-1432.
Berman et al., "The Protein Data Bank," Nucleic Acids Research, Jan. 1, 2000, 28(1), 235-242.
Bird et al., "Biophysical determinants for cellular uptake of hydrocarbon-stapled peptide helices," Nature Chemical Biology, Aug. 22, 2016, 12(10), 845-852.
Bird et al., "Chemical Synthesis of Hydrocarbon-Stapled Peptides for Protein Interaction Research and Therapeutic Targeting," Current Protocols in Chemical Biology, Sep. 1, 2011, 99-117.
Bird et al., "Synthesis and Biophysical Characterization of Stabilized a-Helices of BCL-2 Domains," Methods in Enzymol., Jan. 1, 2008, 446:369-386.
Bose et al., "Mcl-1 as a therapeutic target in acute myelogenous leukemia (AML)," Leukemia Research Reports, Jan. 1, 2013, 2(1), 12-14.
Cang et al., "ABT-199 (venetoclax) and BCL-2 inhibitors in clinical development," Journal of Hematology & Oncology, Dec. 2015, 8(1).
Chames et al., "Therapeutic antibodies: successes, limitations and hopes for the future," British Journal of Pharmacology. May 2009, 157: 220-33.
Chao et al., "Isolating and engineering human antibodies using yeast surface display," Nature Protocols, Aug. 2006, 1(2), 755-768.
Chatr-Arvamontri et al., "The BioGRID interaction database: 2017 update," Nucleic Acids Research, Jan. 4, 2017, 45(D1), D369-D379.
Chaudhury et al., "PyRosetta: a script-based interface for implementing molecular modeling algorithms using Rosetta," Bioinformatics, Jan. 7, 2010, 26(5), 689-691.
Chen et al., "Designing specific protein-protein interactions using computation, experimental library screening, or integrated methods," Protein Science, Jul. 2012, 21(7), 949-963.
Chen et al., "Structure-Based Redesign of the Binding Specificity of Anti-Apoptotic Bcl-xL," Journal of Molecular Biology, Jan. 9, 2013, 425(1), 171-185.
Chevalier et al., "Massively parallel de novo protein design for targeted therapeutics," Nature Publishing Group; Oct. 2017, 550: 74-79.
Chica et al., "Generation of longer emission wavelength red fluorescent proteins using computationally designed libraries," Proceedings of the National Academy of Sciences, Nov. 23, 2010, 107(47), 20257-20262.

(56) References Cited

OTHER PUBLICATIONS

Choi et al., "Bcl-xL promotes metastasis independent of its anti-apoptotic activity," Nature Communications, Jan. 20, 2016, 7, 10384.
Computational Design of Ligand Binding Proteins, 2016, Chapter 14, 15 pages.
Crooks et al., "WebLogo: A Sequence Logo Generator," Genome Research, 2004, 14(6), 1188-1190.
Czabotar et al., "Mutation to Bax beyond the BH3 Domain Disrupts Interactions with Pro-survival Proteins and Promotes Apoptosis," Journal of Biological Chemistrv, Mar. 4, 2011, 286(9), 7123-7131.
Davey et al., "Improving the accuracy of protein stability predictions with multistate design using a variety of backbone ensembles." Proteins: Structure, Function, and Bioinformatics, 2013, [82(5), 771-784.].
DeBartolo et al., "Genome-Wide Prediction and Validation of Peptides That Bind Human Prosurvival Bcl-2 Proteins," PLoS Computational Biology, Jun. 26, 2014, 10(6), e1003693.
DeBartolo et al., "Predictive Bcl-2 Family Binding Models Rooted in Experiment or Structure," Journal of Molecular Biology, Sep. 7, 2012, 422(1), 124-144.
Dutta et al., "Peptide Ligands for Pro-survival Protein Bfl-1 from Computationally Guided Library Screening," ACS Chemical Biology, Feb. 21, 2013, 8(4), 778-788.
Dutta et al., "Potent and Specific Peptide Inhibitors of Human Pro-Survival Protein Bcl-xL," Journal of Molecular Biology, Mar. 27, 2015, 427(6), 1241-1253.
Eckert et al., "Characterization of the steric defense of the HIV-1 gp41 N-trimer region," Protein Science, Dec. 2008, 17(12), 2091-2100.
Edgar "Search and clustering orders of magnitude faster than BLAST," Bioinformatics, Aug. 12, 2010, 26(19), 2460-2461.
Emsley et al., "Features and development of Coot," Acta Crystallographica Section D Biological Crystallography, Apr. 1, 2010, 66(4), 486-501.
Feng et al., "A topological and conformational stability alphabet for multipass membrane proteins," Nature Chemical Biology, Mar. 2016, 12(3), 167-173.
Fernandez-Fuentes et al., "A supersecondarv structure library and search algorithm for modeling loops in protein structures," Nucleic Acids Research, Jan. 1, 2006, 34(7), 2085-2097.
Fire et al., "Mcl-1-Bim complexes accommodate surprising point mutations via minor structural changes," Protein Science, Mar. 2010, 19: 507-19.
Fleishman et al., "Computational Design of Proteins Targeting the Conserved Stem Region of Influenza Hemagglutinin," Science, May 13, 2011, 332(6031), 816-821.
Foight et al., "Enriching peptide libraries for binding affinity and specificity through computationally directed library design," Methods Mol. Biol., 2014, 1561:213-232.
Foight et al., "Locating Herpesvirus Bcl-2 Homologs in tire Specificity Landscape of Anti-Apoptotic Bcl-2 Proteins," Journal of Molecular Biology, Jul. 31, 2015, 427(15), 2468-2490.
Fowler et al., "High-resolution mapping of protein sequence-function relationships," Nature Methods, Sep. 2010, 7(9), 741-746.
Frappier et al., "PixelDB: Protein-peptide complexes annotated with structural conservation of the peptide binding mode," Protein Science, Jan. 2018, 27(1), 276-285.
Gai et al., "Yeast surface display for protein engineering and characterization," Current Opinion in Structural Biology, Aug. 1, 2007 17(4), 467-473.
Gautier et al., "Heliquest: a web server to screen sequences with specific-helical properties," Bioinformatics, Jul. 28, 2008, 24(18), 2101-2102.
Gietz et al., "Transformation of yeast by lithium acetate/single-stranded carrier DNA/polyethylene glycol method. Methods Enzymol," Jan. 1, 2002, 350:87-96.
Gorelik et al., "Inhibition of SCF ubiquitin ligases by engineered ubiquitin variants that target the Cul1 binding site on the Skp1-F-box interface," Proceedings of the National Academy of Sciences, Mar. 29, 2016, 113(13), 3527-3532.
Grigoryan et al., "Design of protein-interaction specificity gives selective bZIP-binding peptides," Nature, Apr. 2009, 458(7240), 859-864.
He et al., "Compositional Bias in Naïve and Chemically-modified Phase-Displayed Libraries uncovered by Paired-end Deep Sequencing," Scientific Reports, Jan. 19, 2018, 8(1), 1214.
Henikoff et al., "Amino acid substitution matrices from protein blocks," Proceedings of the National Academy of Sciences, Nov. 15, 1992, 89(22), 10915-10919.
Herman et al., "Completing the family portrait of the anti-apoptotic Bcl-2 proteins: Crystal structure of human Bfl-1 in complex with Bim," FEES Letters, Oct. 29, 2008, 582(25-26), 3590-3594.
Hiraki et al.,"Targeting MUC1-C suppresses BCL2A1 in triple-negative breast cancer," Signal Transduction and Targeted Therapy, May 12, 2018, 3(1).
Jacobs et al., "Design of structurally distinct proteins using strategies inspired by evolution," Science, May 6, 2016, 352(6286), 687-690.
Jacobs et al., "SwiftLib: rapid degenerate-codon-library optimization through dynamic programming," Nucleic Acids Research, Dec. 24, 2015, 43(5), e34-e34.
Jenson et al "Peptide design by optimization on a data-parameterized protein interaction landscape," Proceedings of the National Academy of Sciences, Oct. 30, 2018, 115(44):E10342-E10351.
Jenson et al., "Epistatic mutations in PUMA BH3 drive an alternate binding mode to potently and selectively inhibit anti-apoptotic Bfl-1," Elife, Jun. 8, 2017, 6, e255741.
Karanicolas et al., "Computational design of affinity and specificity at protein-protein interfaces," Current Opinion in Structural Biology, Aug. 1, 2009, 19(4), 458-463.
Kingsford et al., "Solving and analyzing side-drain positioning problems using linear and integer programming," Bioinformatics, Nov. 16, 2004, 21(7), 1028-1039.
Koss et al., "Defining specificity and on-target activity of BH3-mimetics using engineered B-ALL cell lines," Oncotarget, Mar. 8, 2016, 7(10):11500-11511.
Kotschy et al., "The MCL1 inhibitor S63845 is tolerable and effective in diverse cancer models," Nature, Oct. 2016, 538(7626), 477-482.
Kuang et al., "Dommino 2.0: integrating structurally resolved protein-, RNA-, and DNA-mediated macromolecular interactions," Database, Jan. 1, 2016, 2016: 1-2.
Kumar et al., "Novel Polymeric Nanoparticles for Intracellular Delivery of Peptide Cargos: Antitumor Efficacy of the BCL-2 Conversion Peptide NuBCP-9," Cancer Research, Jun. 15, 2014, 74(12), 3271-3281.
Larkin et al., "Clustal W and Clustal X version 2.0," Bioinformatics, Nov. 1, 2007, 23(21), 2947-2948.
Lee et al., "ConformationalChangesinBcl-2Pro-survivalProteins DetermineTheirCapacitytoBindLigands," J. Biol. Chem., Oct. 30, 2009, 284:30508-30517.
Lee et al., "Novel Bcl-2 Homology-3 Domain-like Sequences Identified from Screening Randomized Peptide Libraries for Inhibitors of the Pro-survival Bcl-2 Proteins," Journal of Biological Chemistry, Nov. 6, 2009, 284(45), 31315-31326.
Lessene et al., "Structure-guided design of a selective BCL-XL inhibitor," Nature Chemical Biology, Jun. 2013, 9(6), 390-397.
Lewis et al., "Anchored Design of Protein-Protein Interfaces," PLoS One, Jun. 17, 2011, 6(6), e20872.
Mackenzie et al., "Protein structural motifs in prediction and design," Current Opinion in Structural Biology, Jun. 1, 2017, 44, 161-167.
Mackenzie et al., "Tertiary alphabet for the observable protein structural universe," Proceedings of the National Academy of Sciences, Nov. 22, 2016, 113(47), E7438-E7447.
Malik et al., "Role of Capsid Structure and Membrane Protein Processing in Determining the Size and Copy Number of Peptides Displayed on the Major Coat Protein of Filamentous Bacteriophage," Journal of Molecular Biology, Jul. 5, 1996, 260(1), 9-21.

(56) References Cited

OTHER PUBLICATIONS

Matochko et al., "Prospective identification of parasitic sequences in phage display screens," Nucleic Acids Research, Nov. 9, 2013, 42(3), 1784-1798.
McConkey et al., "Discrimination of native protein structures using atom-atom contact scoring," Proceedings of the National Academy of Sciences, Mar. 18, 2003, 100(6), 3215-3220.
McCoy et al., "Phaser crystallographic software," Journal of Applied Crystallography, Aug. 1, 2007, 40(4):658-674.
Miles et al., "Hydrocarbon constrained peptides—understanding preorganisation and binding affinity," Chemical Science, 2016, 7(6), 3694-3702.
Moldoveanu et al., "Many players in BCL-2 family affairs," Trends in Biochemical Sciences, Mar. 1, 2014, 39(3), 101-111.
Montero et al., "Why do BCL-2 inhibitors work and where should we use them in the clinic?" Cell Death & Differentiation, Jan. 2018, 25(1), 56-64.
Muñoz et al., "Development of the multiple sequence approximation within the AGADIR model of α-helix formation: Comparison with Zimm-Bragg and Lifson-Roig formalisms," Biopolymers, Apr. 15, 1997, 41(5), 495-509.
Needleman et al., "A general method applicable to the search for similarities in the amino acid sequence of two proteins," Journal of Molecular Biology, Mar. 28, 1970 48(3), 443-453.
Negron et al., "A Set of Computationally Designed Orthogonal Antiparallel Homodimers that Expands the Synthetic Coiled-Coil Toolkit," Journal of the American Chemical Society, Nov. 13, 2014, 136(47), 16544-16556.
Nischan et al., "Covalent Attachment of Cyclic TAT Peptides to GFP Results in Protein Delivery into Live Cells with Immediate Bioavailability," Angewandte Chemie International Edition, Feb. 2, 2014, 54(6), 1950-1953.
Olsson et al., "Upregulation of bfl-1 is a potential mechanism of chemoresistance in B-cell chronic lymphocytic leukaemia," British Journal of Cancer, Sep. 2007, 97(6), 769-777.
Oltersdorf et al., "An inhibitor of Bcl-2 family proteins induces regression of solid tumours," Nature, Jun. 2005, 435(7042), 677-681.
Opferman, "Attacking cancer's Achilles heel: antagonism of anti-apoptotic BCL-2 family members," The FEBS Journal, Jul. 1, 2015, 283(14), 2661-2675.
Otwinowski et al., "[20] Processing of X-ray diffraction data collected in oscillation mode," Methods Enzymol, Jan. 1, 1997, 276:307-326.
PCT International Search Report and Written Opinion in International Appln. No. PCT/US2017/43219, dated Jan. 8, 2018, 14 pages.
PCT International Search Report and Written Opinion in International Appln. No. PCT/US2019/51410, dated Feb. 18, 2020, 11 pages.
Potapov et al., "Data-Driven Prediction and Design of bZIP Coiled-Coil Interactions," PLOS Computational Biology, Feb. 19, 2015, 11(2), e1004046.
Procko et al., "A Computationally Designed Inhibitor of an Epstein-Bair Viral Bcl-2 Protein Induces Apoptosis in Infected Cells," Cell, Jun. 19, 2014, 157(7), 1644-1656.
Qian, et al., "Discovery and Mechanism of Highly Efficient Cyclic Cell-Penetrating Peptides," Biochemistry, Apr. 28, 2016, 55(18), 2601-2612.
Reich et al. "Generating Hish-Accuracv Peptide-Binding Data in High Throughput with Yeast Surface Display and SORTCERY," Computational Design of Ligand Binding Proteins, 2016, 233-247.
Reich et al., "SORTCERY—A High-Throughput Method to Affinity Rank Peptide Ligands." Journal of Molecular Biology, Jun. 5, 2015, 427(11), 2135-2150.
Rezaei et al., "Iterative optimization yields Mcl-1-targetine stapled peptides with selective cytotoxicity to Mcl-1-dependent cancer cells," Proceedings of the National Academy of Sciences, Jan. 30, 2018, 115(5), E886-E895.

Roberts et al., "Computational Design of a PDZ Domain Peptide Inhibitor that Rescues CFTR Activity," PLoS Computational Biology, Apr. 19, 2012, 8(4), e1002477.
Roehrl et al., "A General Framework for Development and Data Analysis of Competitive High-Throughput Screens for Small-Molecule Inhibitors of Protein-Protein Interactions by Fluorescence Polarization," Biochemistry, Dec. 28, 2004, 43(51), 16056-16066.
Romero et al., "Navigating the protein fitness landscape with Gaussian processes," Proceedings of the National Academy of Sciences, Jan. 15, 2013, 110(3), E193-E201.
Roosenburg et al., "Stabilized 111 In-labeled sCCK8 analogues for targeting CCK2-receptor positive tumors: synthesis and evaluation," Bioconjugate Chem., Mar. 19, 2010, 21(4), 663-670.
Ryan et al., "iBH3: simple, fixable BH3 profiling to determine apoptotic priming in primary tissue by flow cytometr," Biol. Chem., Jul. 1, 2016, 397:671-678.
Ryvkin et al., "Phage display peptide libraries: deviations from randomness and correctives," Nucleic Acids Research, Feb. 6, 2018, 46(9), e52-e52.
Salvat et al., "Computationally optimized deimmunization libraries yield highly mutated enzymes with low immunogenicity and enhanced activity," Proceedings of the National Academy of Sciences, Jun. 27, 2017, 201621233.
Scherr et al., "Bcl-xL is an oncogenic driver in colorectal cancer," Cell Death & Disease, Aug. 2016, 7(8), e2342-e2342.
Schoenwaelder et al., "Bcl-xL-inhibitory BH3 mimetics can induce a transient thrombocytopathy that undermines the hemostatic function of platelets," Blood, Aug. 11, 2011, 118(6), 1663-1674.
Schwarze et al., "In Vivo Protein Transduction: Deliverv of a Biologically Active Protein into the Mouse," Science, Sep. 3, 1999, 285(5433), 1569-1572.
Schymkowitz et al., "The FoldX web server: an online force field," Nucleic Acids Research, Jul. 1, 2005, 33 (Web Server), W382-W388.
Senft, et al., "Selective Induction of Cell Death in Melanoma Cell Lines through Targeting of Mcl-1 and A1," PLoS One, Jan. 24, 2012, 7(1), e30821.
Shannon & Weerapana, "Covalent protein modification: the current landscape of residue-specific electrophiles," Curr. Opin. Chem. Biol., Feb. 1, 2015, 24, 18-26.
Shirian et al., "Converting a broad matrix metalloproteinase family inhibitor into a specific inhibitor of MMP-9 and MMP-14," FEBS Letters, Apr. 1, 2018 592(7), 1122-1134.
Smola et al., "A tutorial on support vector regression," Statistics and computing, Aug. 1, 2004, 14(3):199-222.
Souers et al., "ABT-199, a potent and selective BCL-2 inhibitor, achieves antitumor activity while sparing platelets," Nature Medicine, Feb. 2013, 19(2), 202-208.
Stebbins et al., "Structure-based design of covalent Siah inhibitors," Chem Biol., Aug. 22, 2013, 20(8):973-82.
Tompa et al., "A Million Peptide Motifs for the Molecular Biologist," Molecular Cell, Jul. 17, 2014, 55(2), 161-169.
UniProt Consortium, "UniProt: the universal protein knowledgebase," Nucleic Acids Research, Nov. 28, 2016, 45(D1), D158-D169.
Vanhee et al., "BriX: a database of protein building blocks for structural analysis, modeling and design," Nucleic Acids Research, Oct. 22, 2010, 39(suppl_1), D435-D442.
Verma et al., "Pareto optimization of combinatorial mutagenesis libraries," IEEE/ACM Transactions on Computational Biology and Bioinformatics, Jul. 23, 2018, 1-1.
Walensky et al., "Hydrocarbon-Stapled Peptides: Principles, Practice, and Progress," Journal of Medicinal Chemistry, Mar. 6, 2014, 57(15), 6275-6288.
Wang et al., "Alignment of distantly related protein structures: algorithm, bound and implications to homology modeling," Bioinformatics, Jul. 26, 2011, 27(18), 2537-2545.
Wenzel et al., "MCL1 is deregulated in subgroups of diffuse large B-cell lymphoma," Leukemia, Jun. 2012, 27(6), 1381-1390.
Whitehead et al., "Optimization of affinity, specificity and function of designed influenza inhibitors using deep sequencing," Nature Biotechnology, Jun. 2012, 30(6), 543-548.

(56) References Cited

OTHER PUBLICATIONS

Wong et al., "Direct visualization of Bcl-2 family protein interactions using live cell fluorescent protein redistribution assays," Cell death & disease, Mar. 3, 2012; 3(3):e288.

Yecies et al., "Acquired resistance to ABT-737 in lymphoma cells that up-regulate MCL-1 and BFL-1," Blood, Apr. 22, 2010, 115(16), 3304-3313.

Zheng et al., "Computational Design of Selective Peptides to Discriminate between Similar PDZ Domains in an Oncogenic Pathway," Journal of Molecular Biology, Jan. 30, 2015, 427(2), 491-510.

Zheng et al., "Sequence statistics of tertiary structural motifs reflect protein stability," PLOS One, May 26, 2017, 12(5), e0178272.

Zheng et al., "Tertiary Structural Propensities Reveal Fundamental Sequence/Structure Relationships," Structure, May 5, 2015, 23(5), 961-971.

Zhou et al., biorxiv.org [online], "A general-purpose protein design framework based on mining sequence-structure relationships in experimentally-derived protein structures," available Oct. 1, 2018, retrieved Oct. 2, 2019, retrieved from URL <https://www.biorxiv.org/content/10.1101/431635v1>, 15 pages.

\* cited by examiner

| peptide | Mcl-1 | Bfl-1 | Bcl-w | Bcl-$x_L$ | Bcl-2 | KSBcl-2 |
|---|---|---|---|---|---|---|
| MS1 | 1.9 ± 1.0 | 5000 ± 3200 | 1300 ± 230 | 1600 ± 1500 | 2300 ± 1500 | 2.9 ± 0.68 |
| MS2 | 1.5 ± 1.2 | 3100 ± 2300 | 250 ± 76 | 1400 ± 500 | 6200 ± 4100 | <1 |
| MS3 | 2.0 ± 1.2 | 790 ± 140 | 340 ± 69 | 2300 ± 1000 | >3000 | 3.3 ± 1.6 |
| A12 | 2.4 ± 2.3 | 22 ± 6.6 | 210 ± 110 | 9.8 ± 3.1 | 42 ± 8.9 | 4.0 ± 2.6 |
| B3 | <1 | 26 ± 7.7 | 16 ± 6.2 | 4.2 ± 2.1 | 35 ± 11 | 1.43 ± 1.39 |
| NoxaA | 46 ± 11 | ND | ND | ND | ND | ND |
| Bim 23-mer | <1 | <1 | 1.75 ± 1.0 | 2.6 ± 1.9 | 1.9 ± 1.3 | 1.2 ± 0.79 |
| Bim_A2eT | <1 | 31 ± 6.8 | 39 ± 9.4 | 17 ± 4.8 | 43 ± 12 | 1.8 ± 0.81 |
| Bim_A2eT_I2dM | <1 | 150 ± 69 | 260 ± 52 | 83 ± 53 | 210 ± 71 | 0.75 ± 0.37 |
| Bim_A2eT_E2gG | 1.6 ± 0.57 | 250 ± 63 | 94 ± 36 | 37 ± 7.0 | 150 ± 27 | 0.66 ± 0.31 |
| Bim_A2eT_I3dL | <1 | 120 ± 27 | 12 ± 2.6 | 7.6 ± 3.8 | 37 ± 14 | 1.0 ± 0.38 |
| Bim_A2eT_F4aI | <1 | 7.9 ± 2.1 | 16 ± 4.1 | 110 ± 62 | 150 ± 43 | 1.7 ± 0.80 | receptor

FIG. 1

| Peptide | Sequence | IC$_{50}$(nM) | Charge | LDH release | Cellular integration (Light Units) |
|---|---|---|---|---|---|
| MS1 | RPEIWNleTQGLRRLGDEINAYYAR | ≈2200 | 1 | Negative | 6 |
| 3 | IWNleXQGLXRLGDEINAYYARR | 90 | 1 | Positive | - |
| 11 | IWNleXQGLXRLGDEINAYYAR | 105 | -1 | Negative | 700 |
| 12 | EIWNleXQGLXRLGDEINAYYAR | 60 | -1 | Negative | 700 |
| 13 | EIWNleXQGLXRLGDEINAYYA | 84 | -2 | Negative | 351 |
| 14 | IWNleXQELXRLGDEINAYYARR | 55 | 0 | Negative | 814 |
| 15 | IWNleXQSLXRLGDEINAYYARR | 97 | -1 | Negative | 970 |
| 16 | IWNleXQSLXRLGDEINAYYAR | 180 | 0 | Negative | 799 |
| 17 | IWNleXQELXRLGDEINAYYAR | 64 | 0 | Negative | 722 |
| 18 | IWNleXQGLXRLGDEINARYAR | 98 | 0 | Negative | 276 |
| 19 | IWNleXQELXRLGDEINARYAR | 25 | 0 | Negative | 1018 |
| 20 | IWNleXRGLXRLGDEINAYYAR | >1000 | 0 | Negative | 368 |

FIG. 6

| Stapled peptides | Mcl1-2640 (murine) | Mcl1-2643 (murine) | WT MEF | Weak Mcl-1 LP1 | Bcl-2 OCI-LY1 | Bcl-xL MB231 |
|---|---|---|---|---|---|---|
| 11 | - | - | -7.23 | - | >-6 | >-6 |
| 12 | -7.37 | -7.81 | -6.91 | -6.7 | >-6 | >-6 |
| 13 | -7.20 | -7.52 | -6.55 | -6.6 | >-6 | >-6 |
| 14 | -6.63 | - | -6.88 | - | >-6 | >-6 |
| 15 | -7.28 | - | -6.76 | - | >-6 | >-6 |
| 16 | - | - | -6.65 | - | >-6 | >-6 |
| 17 | -6.28 | - | -6.85 | - | >-6 | >-6 |
| 18 | -6.5 | - | - | - | >-6 | >-6 |
| 19 | -7.35 | - | -7.7 | - | >-6 | >-6 |
| 20 | - | - | >-6 | - | >-6 | >-6 |
| Non-cross-linked 3 | >-6 | >-6 | >-6 | >-6 | >-6 | >-6 |
| Bim | -6.3 | -9.0 | -6.3 | -6.9 | -6.2 | -6.3 |
| Bid | -4.6 | -6.7 | -5.2 | -5.4 | -5.9 | -5.0 |
| Puma | -6.3 | -7.6 | -5.3 | -5.7 | -4.9 | -5.8 |
| BMF | -6.3 | -5.5 | -5.8 | -6.3 | -5.4 | -7.1 |
| Bad | >-4 | -4.7 | -6.1 | -7.0 | >-4 | -7.7 |
| NoxaA | >-4 | -4.7 | >-4 | >-4 | -4.6 | >-4 |
| MS1 | >-4 | -5.1 | >-4 | >-4 | -6.6 | >-4 |
| HRK | >-4 | -4.9 | >-4 | >-4 | >-4 | -5.2 |

FIG. 7

| Peptide | Sequence | Cellular integrated intensity | IC50 (nM) |
|---|---|---|---|
| MB2 | IWFAQEIDRIGDEVNAYYARR | 1 | 90 |
| B1 SAHBa | IWFAQEIDXIGDXVNAYYARR | 586 | 189 |
| B1 SAHBf | IWFAQEIDRIGDEVXAYYXRR | 13 | 152 |
| B1 SAHBd | IWFXQEIXRIGDEVNAYYARR | 136.5 | 60 |
| B2 SAHBd | IWFXQEIXRIGDEVNAYYAR | 1056 | 93 |
| B3 SAHBd | EIWFXQEIXRIGDEVNAYYAR | 199 | 33 |
| B1SAHBg | IWFAXEIDXIGDEVNAYYARR | - | 180 |
| B1SAHBh | XWFAQEIDXIGDEVNAYYARR | - | >500 |

FIG. 8

| Dependency: | Weak MCL1 | BFL1/B CLXL | BCL2 | BCL2 | MCL1 | MCL1 |
|---|---|---|---|---|---|---|
| B1 SAHBd | >-6 | >-6 | >-6 | >-6 | -8.2 | -6.6 |
| B1 SAHBa | >-6 | >-6 | >-6 | >-6 | -6.6 | -7.1 |
| B1 SAHBf | >-6 | >-6 | >-6 | >-6 | -7.7 | -8.1 |
| B2 SAHBd | >-6 | >-6 | >-6 | >-6 | -8.3 | -8.7 |
| B3 SAHBd | >-6 | >-6 | >-6 | >-6 | -6.0 | -6.0 |
| B1 SAHBg | >-6 | >-6 | >-6 | >-6 | -7.3 | -6.9 |

FIG. 9

SELECTIVE MCL-1 BINDING PEPTIDES

CROSS-REFERENCE TO RELATED APPLICATIONS

This application is a § 317 National Stage Application of PCT/US2016/023118, filed Mar. 18, 2016, which claims the benefit of U.S. Provisional Application Ser. No. 62/134,904, filed on Mar. 18, 2015. The entire contents of the foregoing are incorporated herein by reference.

TECHNICAL FIELD

This disclosure relates to structurally stabilized therapeutic peptides that bind Mcl-1 with enhanced potency and specificity and methods of using such peptides in the treatment of cancer.

BACKGROUND

Mcl-1 is one of the most frequently amplified genes in cancers and an important factor in resistance to chemotherapeutic agents. Mcl-1 is a member of a family of anti-apoptotic proteins that have homology to Bcl-2 and contain a so-called BH3 domain. Mcl-1 and others members of the family (e.g., Bcl-xL, Bcl-2, Bcl-w, Bfl-1 and Bcl-b) block apoptosis by interfering with the homo-oligomerization of Bak and Bax. The anti-apoptotic proteins either bind directly to Bax and Bak or bind related pro-apoptotic activator proteins (Bim, Bid and Puma), preventing activation of Bax and Bak. Other proteins having a BH3-domain, called sensitizers, antagonize anti-apoptotic function by binding competitively to anti-apoptotic targets and thereby displacing activated Bax/Bak or their direct activator proteins.

Agents that selectively bind Mcl-1 compared to other members of the Bcl-2 family of anti-apoptotic proteins, such as Bcl-xL or Bcl-2, may be useful in treating a variety of cancers.

SUMMARY

The present disclosure provides structurally stabilized peptides that bind human Mcl-1. The stabilized peptides are relatively selective for binding Mcl-1 in that they bind human Mcl-1 with greater affinity than they bind one or more of several proteins considered human homologs of Mcl-1, for example, Bfl-1, Bcl-w, Bcl-xL and Bcl-2.

In some aspects, the present disclosure provides internally cross-linked polypeptides comprising the amino acid sequence F1 G1 A2 B2 C2 D2 E2 F2 G2 A3 B3 C3 D3 E3 F3 G3 A4 B4 C4 D4 E4 F4 G4 A5 (SEQ ID NO:1) wherein F1 is R or a conservative substitution or is missing; G1 is P or a conservative substitution or is missing; A2 is E or a conservative substitution or is missing; B2 is I or a conservative substitution; C2 is W or a conservative substitution; D2 is M or a conservative substitution, L or a conservative substitution, F or a conservative substitution or norleuicine; E2 is T or a conservative substitution, A or a conservative substitution, V or a conservative substitution, Aib or a conservative substitution; F2 is Q or a conservative substitution, R or a conservative substitution; G2 is G, H, E, S or a conservative substitution of one of G, H, E, and S; A3 is L or a conservative substitution, I or a conservative substitution; B3 is R or a conservative substitution, D or a conservative substitution, Q or a conservative substitution, Aib or a conservative substitution, Me-Leu or a conservative substitution; C3 is R or a conservative substitution; D3 is L or a conservative substitution, I or a conservative substitution; E3 is G or a conservative substitution; F3 is D or a conservative substitution; G3 is E or a conservative substitution; A4 is I or a conservative substitution, V or a conservative substitution; B4 is N or a conservative substitution; C4 is A or a conservative substitution; D4 is Y or a conservative substitution; E4 is Y or a conservative substitution; F4 is A or a conservative substitution; G4 is R or a conservative substitution or is missing; A5 is R or a conservative or is missing; wherein the side chains of two amino acids separated by two, three or six amino acids are replaced by an internal staple; the side chains of three amino acids are replaced by internal staples and/or an internal stitch; the side chains of four amino acids are replaced by internal staples, internal stiches, or a combination of internal staples and stiches; or the side chains of at least four amino acids are replaced by internal staples, internal stiches, or a combination of internal staples and stiches.

In some cases the internally cross-linked polypeptides comprise the amino acid sequence F1 G1 A2 B2 C2 D2 E2 F2 G2 A3 B3 C3 D3 E3 F3 G3 A4 B4 C4 D4 E4 F4 G4 A5 (SEQ ID NO:1) wherein F1 is R or is missing; G1 is P or is missing; A2 is E or a conservative substitution or is missing; B2 is I; C2 is W; D2 is M, L, F or norleuicine; E2 is T, A, V, or Aib; F2 is Q or R; G2 is G, H, E, or S; A3 is L or I; B3 is R, D, Q, Aib, or Me-Leu; C3 is R; D3 is L or I; E3 is G; F3 is D; G3 is E; A4 is I or V; B4 is N; C4 is A; D4 is Y; E4 is Y; F4 is A; G4 is R or is missing; A5 is R or is missing; wherein the side chains of two amino acids separated by two, three or six amino acids are replaced by an internal staple; the side chains of three amino acids are replaced by internal staples and/or an internal stitch; the side chains of four amino acids are replaced by internal staples, internal stiches, or a combination of internal staples and stiches; or the side chains of at least four amino acids are replaced by internal staples, internal stiches, or a combination of internal staples and stiches. In some cases, E2 and B3 can be replaced by a hydrocarbon staple.

In some cases internally the cross-linked polypeptides comprise the amino acid sequence F1 G1 A2 B2 C2 D2 E2 F2 G2 A3 B3 C3 D3 E3 F3 G3 A4 B4 C4 D4 E4 F4 G4 A5 (SEQ ID NO:1) wherein F1 is R or is missing; G1 is P or is missing; A2 is E or a conservative substitution or is missing; B2 is I; C2 is W; D2 is M, L, F or norleuicine; E2 is T; F2 is Q or R; G2 is G, H, E, or S; A3 is L; B3 is R, D, Q, Aib, or Me-Leu; C3 is R; D3 is L or I; E3 is G; F3 is D; G3 is E; A4 is I or V; B4 is N; C4 is A; D4 is Y; E4 is Y; F4 is A; G4 is R or is missing; A5 is R or is missing; wherein the side chains of two amino acids separated by two, three or six amino acids are replaced by an internal staple; the side chains of three amino acids are replaced by internal staples and/or an internal stitch; the side chains of four amino acids are replaced by internal staples, internal stiches, or a combination of internal staples and stiches; or the side chains of at least four amino acids are replaced by internal staples, internal stiches, or a combination of internal staples and stiches. In some cases E2 and B3 can be replaced by a hydrocarbon staple.

For example, the side chains of two amino acids separated by 3 or 6 amino acids can be replaced by an internal cross-link, for example a hydrocarbon staple. For example the side chains of E2 and B3 can be replaced by a hydrocarbon staple (position D), the side chains of C3 and G3 can be replaced by a hydrocarbon staple (A position), the side chains of F2 and C3 can be replaced by a hydrocarbon staple (G position) or the sides chains of B2 and B3 are replaced by a hydrocarbon staple (H position).

In some cases internally cross-linked polypeptides include the sequence RPEIWMTQGLRRLGDEINAYYAR (SEQ ID NO:2), wherein: none, one or more (e.g., 1, 2, 3, 4, 5, 6, or 7) of the amino acids are replaced, e.g., by a conservative amino acid substitution, and the side chains of two amino acids are replaced by an internal crosslink. In addition, one or two or three additional amino acids can be removed from or added to (independently) one or both of to the amino or carboxy terminus of SEQ ID NO:2. For example, RPE, RE, or E can be removed from the amino terminus and R can be appended to the carboxy terminus or R can be added to the amino terminus so the sequence terminates in RR. Pairs of amino acids can be replaced by a cross-link in SEQ ID NO:2 (are indicated by X in the following sequences:

```
                                          (SEQ ID NO: 3)
RPEIWMXQGLXRLGDEINAYYA (SEQ ID NO: 4)
RPEIWMTQGLRXLGDXINAYYA (SEQ ID NO: 5)
RPEIWMTQGLRRLGDEINAYYR.
```

In some cases the internally cross-linked polypeptide includes the sequence IWNleXQELXRLGDEINARYAR (SEQ ID NO:18) wherein: X represents the internal cross-link, none, one or more (e.g., 1, 2, 3, 4, 5, 6, or 7) of the amino acids are replaced, e.g., by a conservative amino acid substitution. In addition, one or two or three additional amino acids can added to (independently) one or both of to the carboxy terminus of SEQ ID NO:18. For example R can be added to the carboxy terminus so the sequence terminates in RR. In some cases, the L in SEQ ID NO:18 are not substituted, the sequence GD is not substituted and the second I is not substituted.

In some cases the internally cross-linked polypeptide includes the sequence IWNleTQGLRRLGDEINAYYARR (M1; SEQ ID NO:6), wherein: none, one or more (e.g., 1, 2, 3, 4, 5, 6, or 7) of the amino acids are replaced, e.g., by a conservative amino acid substitution, and the side chains of two amino acids are replaced by an internal crosslink. In addition, one or two or three additional amino acids can be appended to the amino or carboxy terminus of SEQ ID NO:6. For example, RPE, RE, or E can be appended to the amino terminus and R or RR can be appended to the carboxy terminus. Preferred pairs of amino acids that can be replaced by a cross-link are indicated by X in the following sequences:

```
                                          (SEQ ID NO: 20)
EIWMXQGLXRLGDEINAYYA (SEQ ID NO: 21)
PEIWMTQGLRXLGDXINAYYA (SEQ ID NO: 22)
PEIWMTQGLRRLGDEINAYYR.
```

In some cases the internally cross-linked polypeptide includes the sequence IWFAQEIDRIGDEVNAYYARR (B1; SEQ ID NO:23), wherein: none, one or more (e.g., 1, 2, 3, 4, 5, 6, or 7) of the amino acids are replaced, e.g., by a conservative amino acid substitution, and the side chains of two amino acids are replaced by an internal crosslink. In addition, one or two or three additional amino acids can be appended to the amino or carboxy terminus of any of SEQ ID NOs:1-32. For example, RPE, RE, or E can be appended to the amino terminus and R or RR can be appended to the carboxy terminus. Preferred pairs of amino acids to be replaced by a cross-link in SEQ ID NOs:1-32 are indicated by X in the following sequences:

```
                                          (SEQ ID NO: 20)
EIWMXQGLXRLGDEINAYYA (SEQ ID NO: 21)
PEIWMTQGLRXLGDXINAYYA (SEQ ID NO: 22)
PEIWMTQGLRRLGDEINAYYR.
```

In some cases, the internally cross-linked peptide is at least 80% (e.g., 80%, 85%, 90%, 95%, 98%, 99%, 99.5%, or 100%) identical to the sequence of any of SEQ ID NOs:1-32. In some cases, the internally cross-linked peptide is at least 80% (e.g., 80%, 85%, 90%, 95%, 98%, 99%, 99.5%, or 100%) identical to the sequence of any of SEQ ID NOs:1-54. The amino acid side chains that are replaced by a cross-link are considered non-identical in calculating percent identity.

In some embodiments, internally cross-linked polypeptides of the disclosure comprise one of the following peptides (SEQ ID NOs: 6-19):

```
                                          (SEQ ID NO: 6)
IWNleTQGLRRLGDEINAYYARR;

(SEQ ID NO: 7)
IWNleTQGLRXLGDXINAYYARR (peptide 7);

(SEQ ID NO: 8)
IWNleTQGLRRLGDEIXAYYXRR (peptide 10);

(SEQ ID NO: 9)
IWNleXQGLXRLGDEINAYYARR (peptide 3);

(SEQ ID NO: 10)
IWNleXQGLXRLGDEINAYYAR (peptide 11);

(SEQ ID NO: 1)
EIWNleXQGLXRLGDEINAYYAR (peptide 12);

(SEQ ID NO: 12)
EIWNleXQGLXRLGDEINAYYA (peptide 13);

(SEQ ID NO: 13)
IWNleXQELXRLGDEINAYYARR (peptide 14);

(SEQ ID NO: 14)
IWNleXQSLXRLGDEINAYYARR (peptide 15);

(SEQ ID NO: 15)
IWNleXQSLXRLGDEINAYYAR (peptide 16);

(SEQ ID NO: 16)
IWNleXQELXRLGDEINAYYAR (peptide 17);

(SEQ ID NO: 17)
IWNleXQGLXRLGDEINARYAR (peptide 18);

(SEQ ID NO: 18)
IWNleXQELXRLGDEINARYAR (peptide 19);
and (SEQ ID NO: 19)
IWNleXRGLXRLGDEINAYYAR (peptide 20);
``` wherein the side chains of two amino acids separated by three amino acids are replaced by an internal cross-link (indicated by X; Nle is norleucine). In addition, 1, 2, 3, 4, 5, 6, 7 amino acids in any of these peptides can be substituted, e.g., conservatively. In some cases SEQ ID NO:8 is not substituted at the L following QG. In some cases SEQ ID NO:8 is not substituted at the L following QG and is not substituted at the T following WNle. In some cases SEQ ID NO:8 is not substituted at the T following WNle.

In some embodiments, internally cross-linked polypeptides of the disclosure comprise one of the following peptides (SEQ ID NOs:23 -30):

IWFAQEIDRIGDEVNAYYARR; (SEQ ID NO: 23)

IWFAQEIDXIGDXVNAYYARR; (SEQ ID NO: 24)

IWFAQEIDRIGDEVXAYYXRR; (SEQ ID NO: 25)

IWFXQEIXRIGDEVNAYYARR; (SEQ ID NO: 26)

IWFXQEIXRIGDEVNAYYAR; (SEQ ID NO: 27)

EIWFXQEIXRIGDEVNAYYAR; (SEQ ID NO: 28)

IWFAXEIDXIGDEVNAYYARR; and (SEQ ID NO: 29)

XWFAQEIXRIGDEVNAYYARR; (SEQ ID NO: 30)

wherein the side chains of two amino acids separated by three amino acids are replaced by an internal cross-link (indicated by X). In addition, 1, 2, 3, 4, 5, 6, 7 amino acids in any of these peptides can be substituted, e.g., conservatively.

In some embodiments of all of the polypeptides described herein, an RR dipeptide can be appended to the amino or carboxy terminus of the stapled peptide. In some embodiments of all of the polypeptides described herein, the polypeptide is modified as needed, such that the RR is the carboxy terminal sequence.

In some embodiments of all of the polypeptides described herein, the cross-link is an alkyl, alkenyl or alkynyl group. When the side chains of two amino acids separated by three amino acids are replaced by an internal cross-link, the cross-link is preferably a C8 alkenyl group with a single double bond between the $4^{th}$ and $5^{th}$ carbons.

In some cases there can be a pair of internal cross-links that join the alpha carbons of three amino acids (a central amino acid is cross-linked to each of two amino acids). In some embodiments, internally cross-linked polypeptides of the disclosure include an internal staple replacing the side chains of two amino acids separated by three or six amino acids. In some embodiments, the internal staples and/or the internal stitch comprises at least two internal staples (replacing the side chains of 4 amino acids, i.e., each staple is between two amino acids separated by 3 amino acids). In some embodiments, the internal staples and/or the internal stitch comprises a combination of at least one internal staple and an internal stitch. In some embodiments, the internal stitch replaces the side chain of a first amino acid and a second and a third amino acid thereby cross-linking the first amino acid (which lies between the second and third amino acids) to the second and third amino acid via an internal cross-link, wherein the first and second amino acid are separated by two, three, or six amino acids, the first and the third amino acids are separated by two, three, or six amino acids, and the second and third amino acids are distinct amino acids. In some embodiments, the internal stitch replacing the side chains of the three amino acids cross-links a pair of amino acids separated by two, three, or six amino acids. In some embodiments, the side chains of the four amino acids of the internally cross-linked polypeptides of the disclosure are replaced by two distinct internal staples. In some embodiments, a first of the two distinct internal staples cross-links a first pair of amino acids separated by two, three, or six amino acids, and a second of the at least two distinct internal staples cross-links a second pair of amino acids separated by two, three, or six amino acids. In some embodiments, internally cross-linked polypeptides of the disclosure include internal staples, internal stiches, or a combination of internal staples and internal stitches replacing the side chains of at least four amino acids, such as at least one staple and at least one stitch. In some embodiments, the at least one staple cross-links a pair of amino acids separated by two, three, or six amino acids and the at least one stitch cross-links a first amino acid to a second amino acid and a third amino acid, wherein the first and second amino acid are separated by two, three, or six amino acids, the first and the third amino acids are separated by two, three, or six amino acids, and the second and third amino acids are distinct amino acids.

In some aspects, the disclosure provides pharmaceutical compositions that include one or more internally cross-linked polypeptides of the disclosure. In some embodiments, such pharmaceutical compositions can also include one or more medicaments for the treatment of cancer and/or the alleviation of one or more symptoms associated with cancer.

In some aspects, the disclosure provides methods for treating cancer in a subject; any of the types of cancers referred to herein. These methods can include selecting a subject suffering from cancer; and administering to the subject an effective amount of the stabilized peptide described herein. In some embodiments, methods include assessing a level of Mcl-1 in the subject before treatment. For example, the peptides disclosed herein can be used, to treat a subject suffering from one or more of a cancer or tumor, e.g. of the lung, breast, epithelium, large bowel, rectum, testicle, gallbladder, bile duct, biliary tract, prostate, colon, stomach, esophagus, pancreas, liver, uterus, ovary, or brain.

In some cases the polypeptides of the disclosure comprise the amino acid sequence of SEQ ID NO: 1, wherein A3 is L, D3 is L, E3 is G, F3 is D, and A4 is I. In some cases the amino acid sequence of the peptide comprises IWNleXQELXRLGDEINARYAR (SEQ ID NO:18). In some cases, A3 is L, D3 is isoleucine, E3 is G, F3 is D, and A4 is I. In some cases, A3 is isoleucine, D3 is L, E3 is G, F3 is D, and A4 is I. In some cases, A3 is isoleucine, D3 is isoleucine, E3 is G, F3 is D, and A4 is I.

In some cases the polypeptides of the disclosure comprise the amino acid sequence of IWFAQEIDRIGDEVNAYYAR (SEQ ID NO:31). In some cases the polypeptides of the disclosure comprise the amino acid sequence of EIWFAQEIDRIGDEVNAYYAR (SEQ ID NO:32). In some cases the polypeptides of the disclosure comprise the amino acid sequence of RPEIWLTQSLQRLGDEINAYYAR (SEQ ID NO:33). In some cases the polypeptides of the disclosure comprise the amino acid sequence of RPEIWLTQHLQRLGDEINAYYAR (SEQ ID NO:34). In some cases the polypeptides of the disclosure comprise the amino acid sequence of RPEIWITQELRRIGDEINAYYAR (SEQ ID NO:44).

In some cases the polypeptides of the disclosure comprise the amino acid sequence of IWMTQGLRRLGDEINAYYAR (SEQ ID NO:45). In some cases the polypeptides of the disclosure comprise the amino acid sequence of IXNleTQXIRRLGDEINAYYARR (SEQ ID NO:46) (peptide 1) and X represents the internal cross-link. In some cases the polypeptides of the disclosure comprise the amino acid sequence of IWXTQGXRRLGDEINAYYARR (SEQ ID NO:47) (peptide 2) and X represents the internal cross-link. In some cases the polypeptides of the disclosure comprise the amino acid sequence of IWNleXQGLXRLGDEINAYYARR (SEQ ID NO:9) (peptide 3) and X represents the internal cross-link. In some cases the polypeptides of the disclosure comprise the amino acid sequence of IWNleTQXLRRXGDEINAYYARR (SEQ ID NO:48) (peptide 4) and X represents the internal cross-link. In some cases the polypeptides of the disclosure comprise the amino acid sequence of IWNleTQGXRRLXDEINAYYARR (SEQ ID NO:49) (peptide 5) and X represents the internal cross-link. In some cases the polypeptides of the disclosure comprise the amino acid sequence of IWNleTQGLXRLGXEINAYYARR (SEQ ID NO:50) (peptide 6) and X represents the internal cross-link. In some cases the polypeptides of the disclosure comprise the amino acid sequence of IWNleTQGLRXLGDXINAYYARR (SEQ ID NO:7) (peptide 7) and X represents the internal cross-link. In some cases the polypeptides of the disclosure comprise the amino acid sequence of IWNleTQGLRRLXDEIXAYYARR (SEQ ID NO:51) (peptide 8) and X represents the internal cross-link. In some cases the polypeptides of the disclosure comprise the amino acid sequence of IWNleTQGLRRLGDXINAXYARR (SEQ ID NO:52) (peptide 9) and X represents the internal cross-link. In some cases the polypeptides of the disclosure comprise the amino acid sequence of IWNleTQGLRRLGDEIXAYYXRR (SEQ ID NO:8) (peptide 10) and X represents the internal cross-link.

In some cases the polypeptides of the disclosure comprise the amino acid sequence of RPEIWNleTQGLRRLGDEINAYYAR (SEQ ID NO:53). In some cases the polypeptides of the disclosure comprise the amino acid sequence of IWMTQGLRRLGDEINAYYARR (SEQ ID NO:54). In some cases the polypeptides of the disclosure comprise the amino acid sequence of EIWNleXQGLXRLGDEINAYYAR (SEQ ID NO:11) and X represents the internal cross-link. In some cases the polypeptides of the disclosure comprise the amino acid sequence of EIWNleXQGLXRLGDEINAYYA (SEQ ID NO:12) and X represents the internal cross-link. In some cases the polypeptides of the disclosure comprise the amino acid sequence of IWNleXQELXRLGDEINAYYARR (SEQ ID NO:13) and X represents the internal cross-link. In some cases the polypeptides of the disclosure comprise the amino acid sequence of IWNleXQSLXRLGDEINAYYARR (SEQ ID NO:14) and X represents the internal cross-link. In some cases the polypeptides of the disclosure comprise the amino acid sequence of IWNleXQSLXRLGDEINAYYAR (SEQ ID NO: 15) and X represents the internal cross-link. In some cases the polypeptides of the disclosure comprise the amino acid sequence of IWNleXQELXRLGDEINAYYAR (SEQ ID NO:16) and X represents the internal cross-link. In some cases the polypeptides of the disclosure comprise the amino acid sequence of IWNleXQGLXRLGDEINARYAR (SEQ ID NO:17) and X represents the internal cross-link. In some cases the polypeptides of the disclosure comprise the amino acid sequence of IWNleXRGLXRLGDEINAYYAR (SEQ ID NO:19) and X represents the internal cross-link.

In some embodiments of all of the polypeptides described herein, the peptides comprise an amino acid sequence of no more than 30 amino acids. In some embodiments of all of the polypeptides described herein, the peptides comprise an amino acid sequence of no more than 24 amino acids. In some cases the peptide consists of no more than 30 amino acids and comprises the amino acid sequence of any one of SEQ ID NOs: 35-43.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF THE DRAWINGS

FIG. 1|Results of binding studies.

FIG. 2a. shows a modeling of Mcl-1:Bim BH3; and Bfl-1:Bim BH3. FIG. 2b. shows a modeling of Bfl-1:Bim BH3; and Mcl-1:Bim BH3. FIG. 2c. shows a modeling of Mcl-1:Bim BH3; and Bcl-xL:Bim BH3. FIG. 2d. shows a modeling of Bcl-xL:Bim BH3.

FIG. 6|Distribution of length, net charge, and charge distribution of various internally cross-linked peptides. Columns left to right: amino acid sequence of stapled peptides, Mcl-1 binding activities as measured by competition FP assay with fluorescently labeled 23mer Bim-BH3, net charge, lactate dehydrogenase (LDH) release and cellular integrated intensity of fluoresceinated peptides, reflecting cell uptake. Peptides 3, 11-20 are SEQ ID NOs: 9-19 respectively.

FIG. 7|Results of BH3 profiling studies. EC50 values (given as the logarithm of the peptide concentration in nM) for mitochondrial depolarization induced by stapled BH3 peptides as measured by BH3 profiling. The table lists cell lines tested, which have different dependencies on anti-apoptotic proteins for survival. Peptides 11-20 are SEQ ID NOs: 10-19 respectively.

FIG. 8|Results of studies assessing cell permeability of various internally cross-linked peptides. Stapled peptides based on MB2 lead peptide are shown. Columns left to right: Name, Amino acid sequence of stapled peptides, cellular integrated intensity of fluoresceinated peptides (reflecting cell uptake), Mcl-1 binding activities as measured by competition FP assay with fluorescently labeled 23mer Bim-BH3. MB2 (SEQ ID NO:23); B1 SAHBa (SEQ ID NO:24); B1 SAHBf (SEQ ID NO:25); B1 DAHBd (SEQ ID NO:26); B2 SAHBd (SEQ ID NO:27); B3 SAHBd (SEQ ID NO:28); B1 SAHBg (SEQ ID NO:29); B1 SAHBh (SEQ ID NO:30).

FIG. 9|Results of BH3 profiling studies. EC50 values (given as the logarithm of the peptide concentration in nM) for mitochondrial depolarization induced by stapled BH3 peptides as measured by BH3 profiling. Sequences are given in FIG. 8.

FIG. 10|Results of cell viability assay.

```
IWNleXQSLXRLGDEINAYYARR is SEQ ID NO: 14
and

IWNleXQELXRLGDEINARYAR is SEQ ID NO: 18.
```

Figure 11:
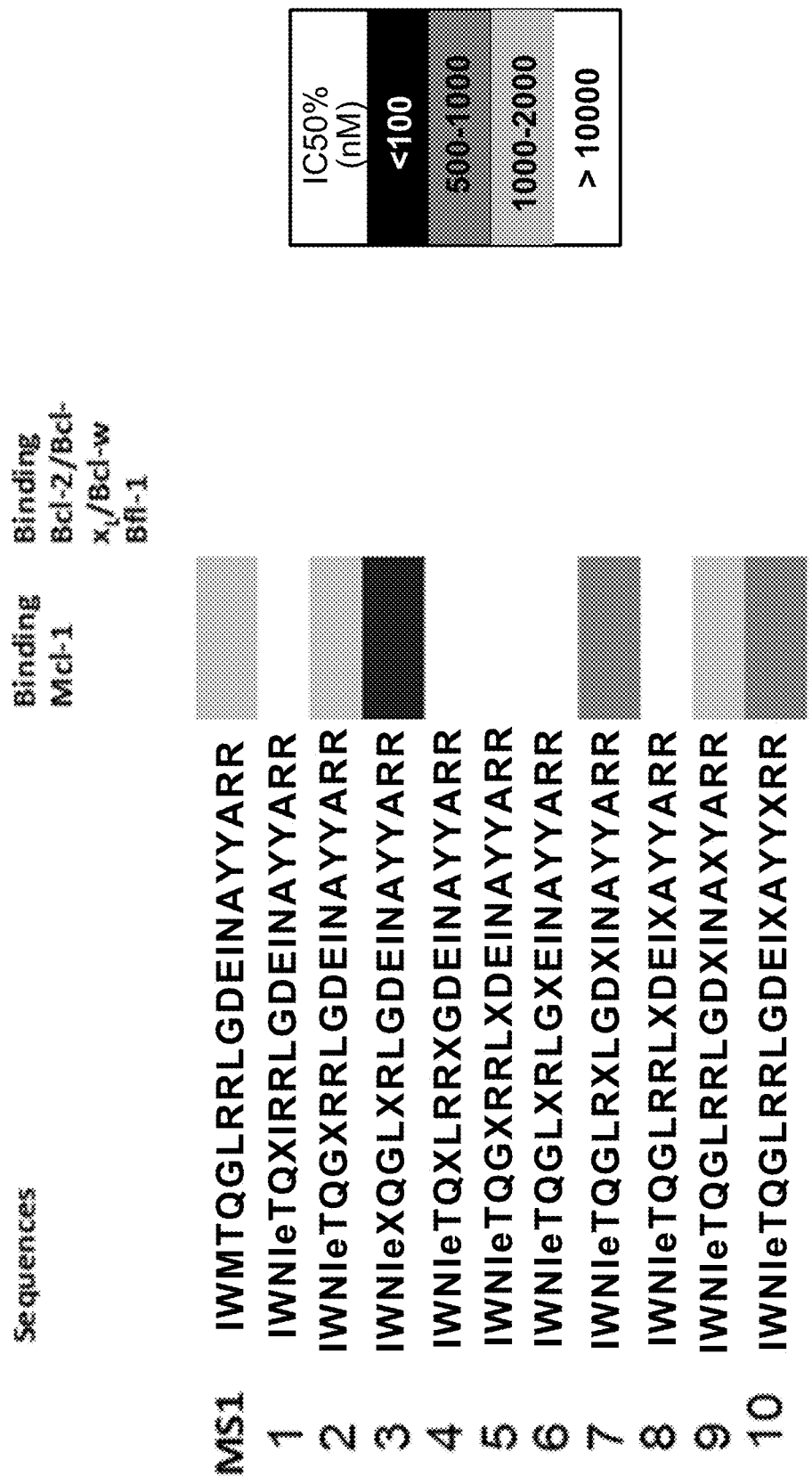

FIG. 11|Table listing amino acid sequences of stapled MS1 peptides and Bcl-2 family protein binding activities as measured by competition FP assay with fluorescently labeled 23mer Bim-BH3. Peptides 1-10 are SEQ ID NOs: 46, 47, 9, 48, 49, 50, 7, 51, 52, and 8 respectively.

Figure 12:
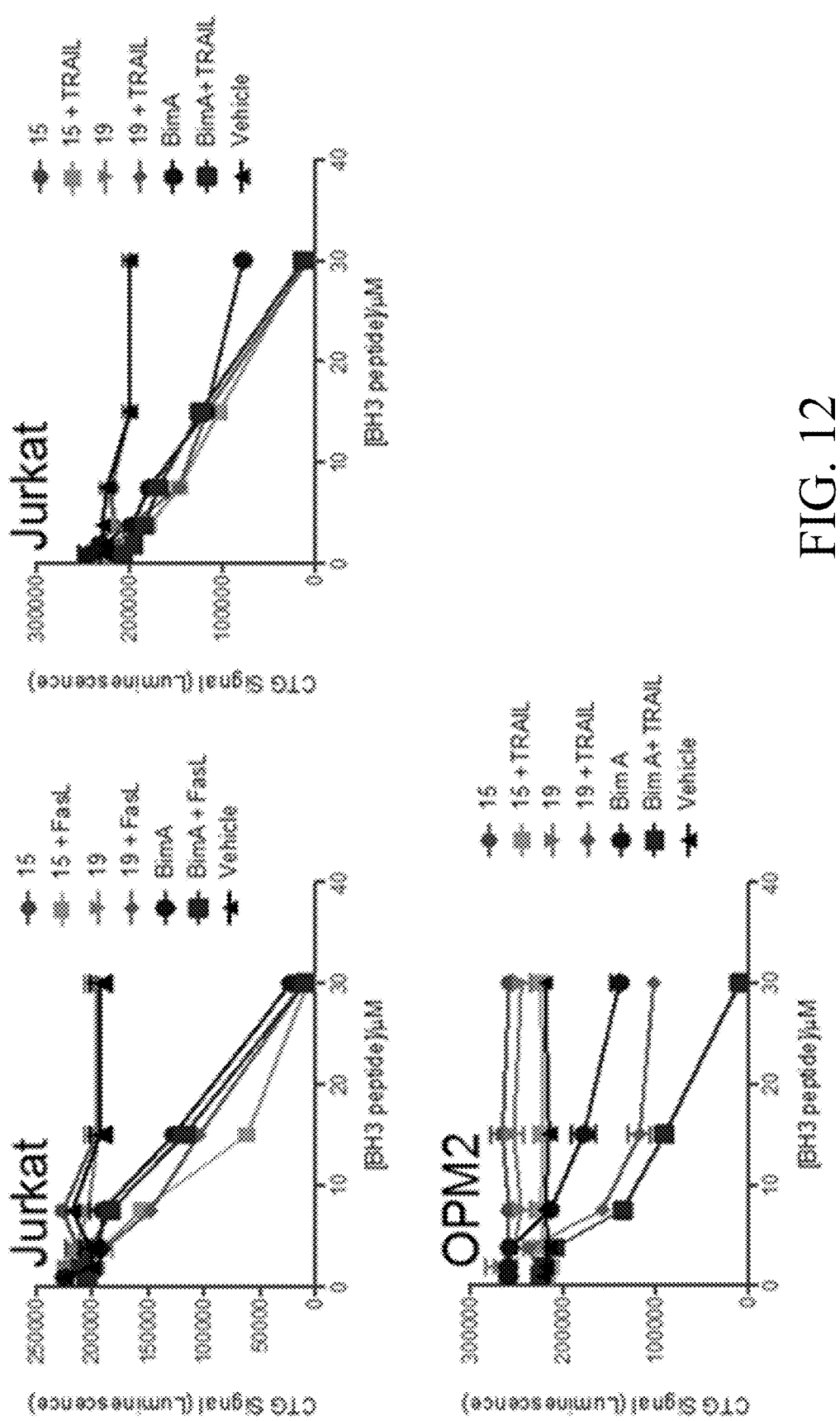

FIG. 12|Results of cell viability assay. Sensitization by Mcl-1-targeting stapled peptides (peptide 15 (M6r) (SEQ ID NO:14) and peptide 19 (M10r) (SEQ ID NO:18)) leads to cell death via cell death receptor signaling. Jurkat and OPM2 cells were exposed to stapled peptide singly and in combination with low-dose death receptor ligands, TRAIL and Fas ligand. Cell viability measured by CTG assay at 24 hours revealed dose-responsive apoptosis in serum-supplemented media (10% FBS).

Figure 13:
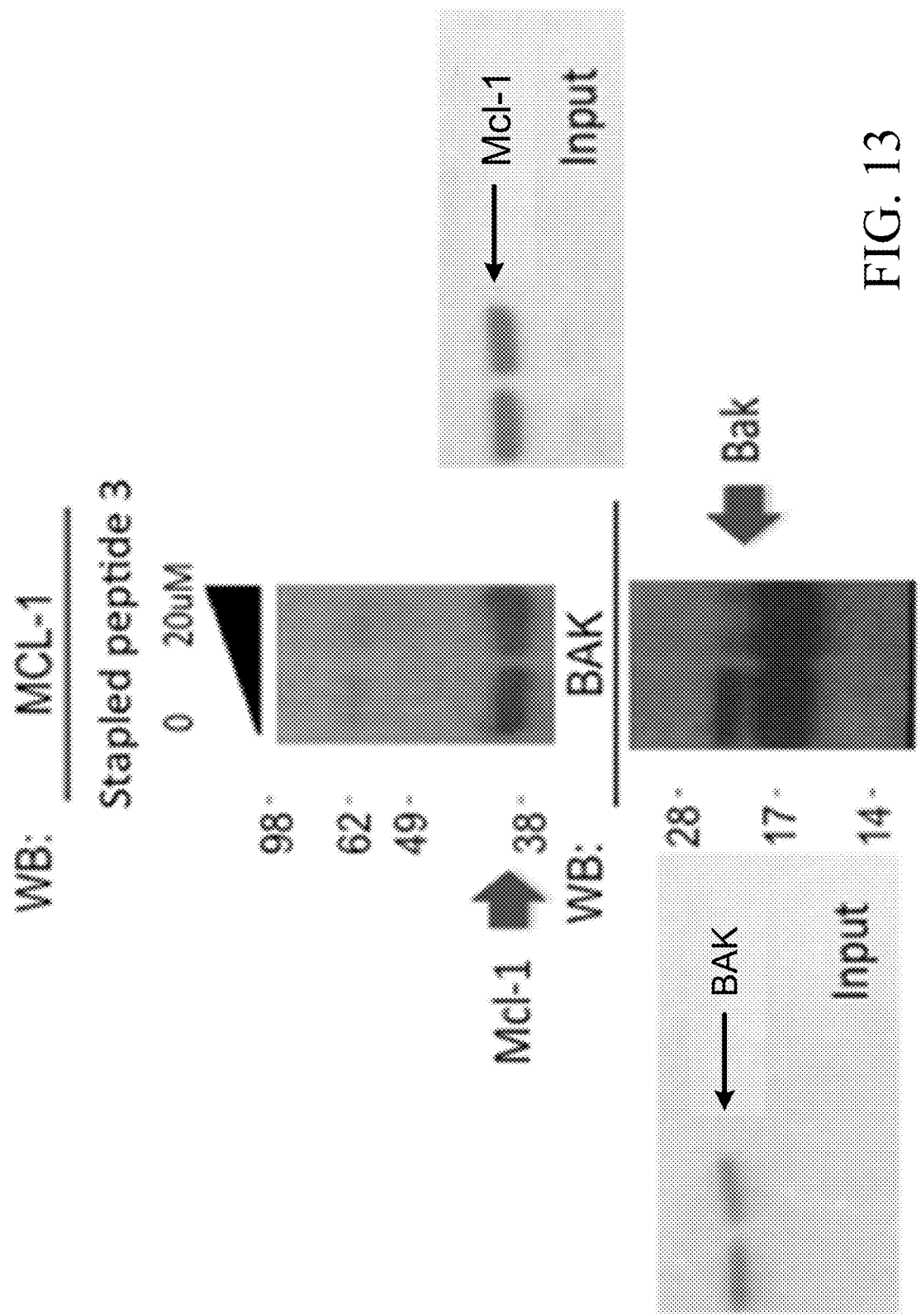

FIG. 13|Results of Mcl-1 immunoprecipitation and Bak western analysis. The interaction between Bak and Mcl-1 was disrupted by treatment of OCI-AML3 cell lysate with the most potent stapled peptide 3 (Mlr) (SEQ ID NO:9). The anti-Mcl-1 antibody immunoprecipitated the Mcl-1 (~40 kD). The same blot was probed with the Bak (~28 kD) antibody.

Figure 14:
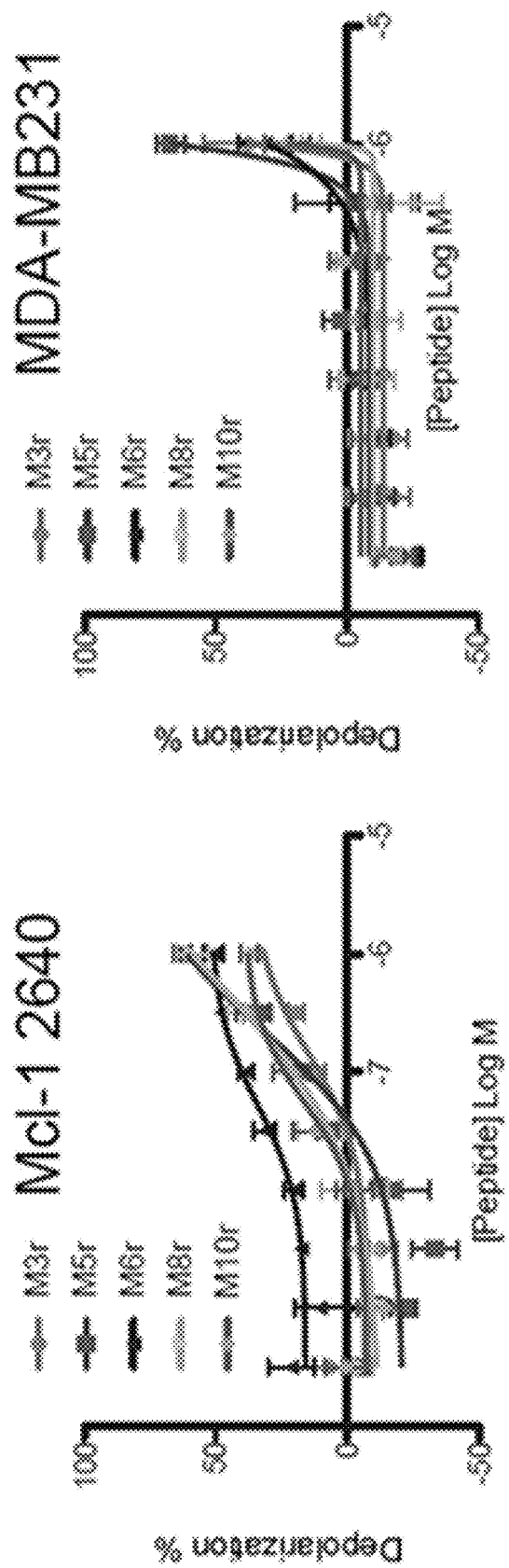

FIG. 14|Results of BH3 profiling, following cell permeabilization with digitonin. Left: Depolarization of the mitochondrial membrane of Mcl-1 2640 cells in response to treatment with different stapled peptides. EC50 values for M3r (SEQ ID NO:11), M5r (SEQ ID NO:13), M6r (SEQ ID NO:14), M8r (SEQ ID NO:16) and M10r (SEQ ID NO:18) are 158, 251, 50, 630, and 39 nM. Right: Depolarization of the mitochrondrial membrane of MDA-MB231 cells in response to treatment with different stapled peptides.

Figure 15:
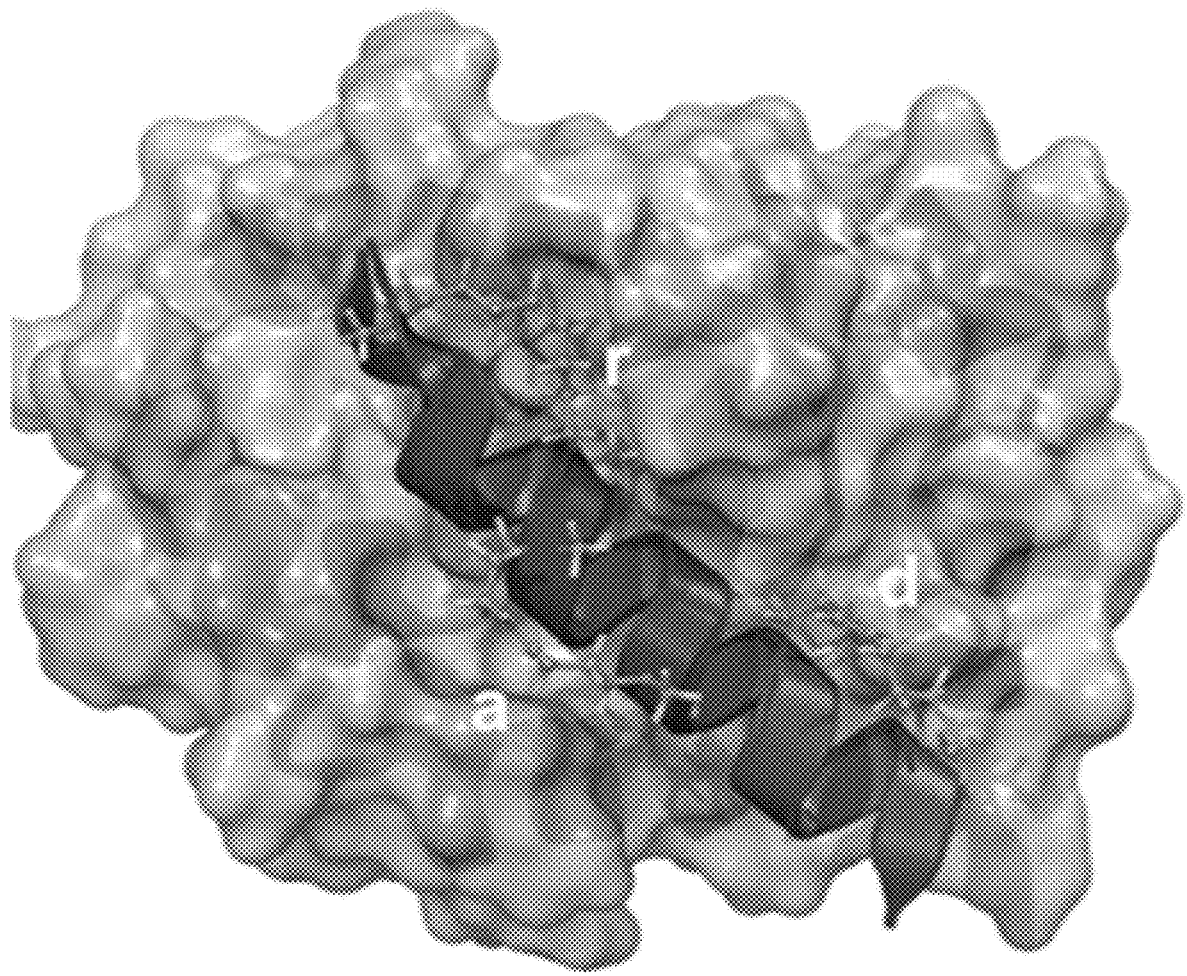

FIG. 15|Modeling of Mla (SEQ ID NO:7), Mld (SEQ ID NO:8) and M1r (SEQ ID NO:9) bound to Mcl-1, obtained through Bioluminate computational modeling. The Mcl-1: BH3 peptide crystal structure employed in the modeling was obtained from the protein databank (PDB:3MK8).

Figure 16:
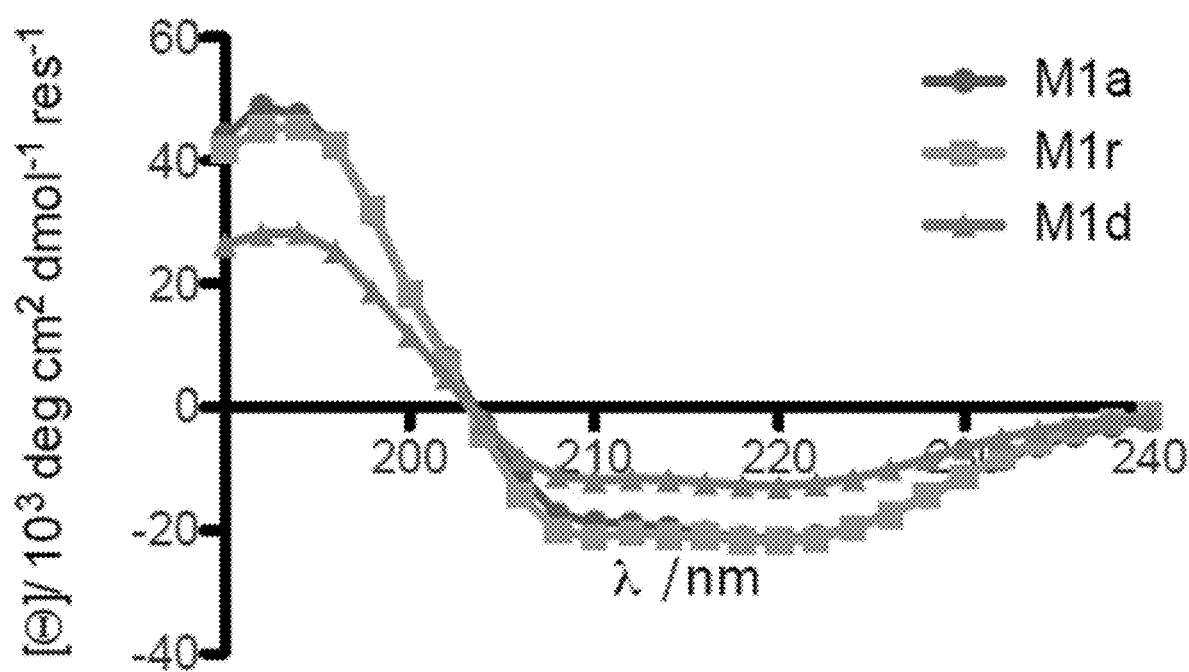

FIG. 16|Results of circular dichroism analysis of stapled peptides, dissolved in Tris buffer pH 7.4.

DETAILED DESCRIPTION

The present disclosure provides structurally stabilized Mcl-1-binding peptides comprising at least two modified amino acids joined by an internal (intramolecular) cross-link (or staple), wherein the at least two amino acids are separated by 3 or 6 amino acids. Stabilized peptides include stapled and/or stitched peptides.

Amino acids are the building blocks of the peptides herein. The term "amino acid" refers to a molecule containing both an amino group and a carboxyl group as well as a side chain Amino acids suitable for inclusion in the peptides disclosed herein include, without limitation, natural alpha-amino acids such as D- and L-isomers of the 20 common naturally occurring alpha-amino acids found in peptides (e.g., Ala (A), Arg (R), Asn (N), Cys (C), Asp (D), Gln (Q), Glu (E), Gly (G), His (H), Ile (I), leu (L), Lys (K), Met (M), Phe (F), Pro (P), Ser (S), Thr (T), Trp (W), Tyr (Y), and Val (V), unnatural alpha-amino acids (including, but not limited to α,α-disubstituted and N-alkylated amino acids), natural beta-amino acids (e.g., beta-alanine), and unnnatural beta-amino acids. Amino acids used in the construction of peptides of the present invention can be prepared by organic synthesis, or obtained by other routes, such as, for example, degradation of or isolation from a natural source.

There are many known unnatural amino acids any of which may be included in the peptides of the present invention. Some examples of unnatural amino acids are 4-hydroxyproline, desmosine, gamma-aminobutyric acid, beta-cyanoalanine, norvaline, 4-(E)-butenyl-4(R)-methyl-N-methyl-L-threonine, N-methyl-L-leucine, 1-amino-cyclopropanecarboxylic acid, 1-amino-2-phenyl-cyclopropanecarboxylic acid, 1-amino-cyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3- diaminopropionic acid, 2,4-diaminobutyric acid, 2-aminoheptanedioic acid, 4-(aminomethyl)benzoic acid, 4-aminobenzoic acid, ortho-, meta- and /para-substituted phenylalanines (e.g., substituted with —C(=O)C$_6$H$_5$; —CF$_3$; —CN; -halo; —NO2; CH$_3$), disubstituted phenylalanines, substituted tyrosines (e.g., further substituted with -Q=O) C$_6$H$_5$; —CF$_3$; —CN; -halo; —NO$_2$; CH$_3$), and statine. Additionally, amino acids can be derivatized to include amino acid residues that are hydroxylated, phosphorylated, sulfonated, acylated, and glycosylated, to name a few.

Useful amino acids include:

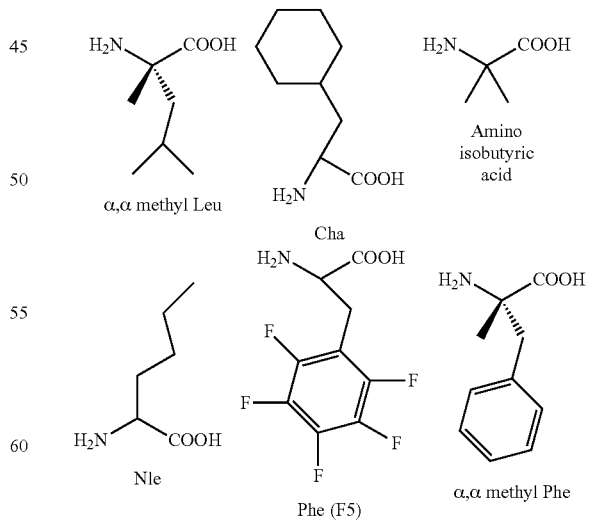

In some instances, peptides include only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a peptide or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc.

Therefore a compound comprising a polypeptide described herein, can include a polypeptide that is modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc.

In some instances, peptides can include (e.g., comprise, consist essentially of, or consist of) at least seven (e.g., 7, 8, 9, 10, 11, 12, 13, 14, 15, 16, 17, 18, 19, 20, 21, 22) contiguous amino acids of any of SEQ ID NOs: 1-32.

In some instances, a "conservative amino acid substitution" can include substitutions in which one amino acid residue is replaced with another amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Methods for determining percent identity between amino acid sequences are known in the art. For example, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 70%, 80%, 90%, or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The determination of percent identity between two amino acid sequences is accomplished using the BLAST 2.0 program. Sequence comparison is performed using an ungapped alignment and using the default parameters (Blossom 62 matrix, gap existence cost of 11, per residue gapped cost of 1, and a lambda ratio of 0.85). The mathematical algorithm used in BLAST programs is described in Altschul et al. (Nucleic Acids Res. 25:3389-3402, 1997).

As disclosed above, peptides herein include at least two modified amino acids that together form an internal (intramolecular) cross-link (or staple), wherein the at least two modified amino acids are separated by: (A) three amino acid (i.e., i, i+4) or (B) six amino acids (i.e., i, i+7). In the case of a cross- between i and i+4 the cross-link can be a C8 alkene (e.g,. with a single double bond between the $4^{th}$ and $5^{th}$ carbons) alkylene or alkenylene. In the case of a cross-link between i and i+7 the cross-link can be a C11, C12 or C13 alkylene or alkenylene. When the cross-link is an alkenylene there can one or more double bonds. In the case of a cross-link between i and i+4 the cross-link can be a C8 alkyl or alkene. In the case of a cross-link between i and i+7 the cross-link can be a C11, C12 or C13 alkyl or alkene (e.g., a C11 alkene having a single double bond). When the cross-link is an alkene there can be one or more double bonds.

"Peptide stapling" is a term coined from a synthetic methodology wherein two olefin-containing side-chains (e.g., cross-linkable side chains) present in a polypeptide chain are covalently joined (e.g., "stapled together") using a ring-closing metathesis (RCM) reaction to form a cross-linked ring (Blackwell et al., J. Org. Chem., 66: 5291-5302, 2001; Angew et al., Chem. Int. Ed. 37:3281, 1994). As used herein, the term "peptide stapling," includes the joining of two (e.g., at least one pair of) double bond-containing side-chains, triple bond-containing side-chains, or double bond-containing and triple bond-containing side chain, which may be present in a polypeptide chain, using any number of reaction conditions and/or catalysts to facilitate such a reaction, to provide a singly "stapled" polypeptide. The term "multiply stapled" polypeptides refers to those polypeptides containing more than one individual staple, and may contain two, three, or more independent staples of various spacings and compositions. Additionally, the term "peptide stitching," as used herein, refers to multiple and tandem "stapling" events in a single polypeptide chain to provide a "stitched" (e.g., tandem or multiply stapled) polypeptide, in which two staples, for example, are linked to a common residue. Peptide stitching is disclosed in WO 2008121767 and in WO 2010/068684, which are both hereby incorporated by reference. In some instances, staples, as used herein, can retain the unsaturated bond or can be reduced (e.g., as mentioned below in the stitching paragraph description).

While many peptide staples have all hydrocarbon cross-links, other type of cross-links or staples can be used. For example, triazole-containing (e.g., 1, 4 triazole or 1, 5 triazole) crosslinks can be used (Kawamoto et al. 2012 Journal of Medicinal Chemistry 55:1137; WO 2010/060112).

Stapling of a peptide using all-hydrocarbon cross-link has been shown to help maintain its native conformation and/or secondary structure, particularly under physiologically relevant conditions (Schafmiester et al., J. Am. Chem. Soc., 122:5891-5892, 2000; Walensky et al., Science, 305:1466-1470, 2004).

Stapling the polypeptide herein by an all-hydrocarbon crosslink predisposed to have an alpha-helical secondary structure can constrain the polypeptide to its native alpha-helical conformation. The constrained secondary structure may, for example, increase the peptide's resistance to proteolytic cleavage, may increase the peptide's thermal stability, may increase the peptide's hydrophobicity, may allow for better penetration of the peptide into the target cell's membrane (e.g., through an energy-dependent transport mechanism such as pinocytosis), and/or may lead to an improvement in the peptide's biological activity relative to the corresponding uncrosslinked (e.g., "unstitched" or "unstapled") peptide.

Stabilized peptides herein include at least two internally cross-linked or stapled amino acids, wherein the at least two amino acids are separated by three (i.e., i, i+4) or six (i.e., i, i+7) amino acids. While at least two amino acids are required to support an internal cross-link (e.g., a staple), additional pairs of internally cross-linked amino acids can be included in a peptide, e.g., to support additional internal cross-links (e.g., staples). For example peptides can include 1, 2 or 3 staples.

Alternatively or in addition, peptides can include three internally cross-linked or stitched amino acids, e.g., yielding two staples arising from a common origin. A peptide stitch includes at least three internally cross-linked amino acids, wherein the middle of the three amino acids forms an internal cross-link (between alpha carbons) with each of the two flanking (not immediately adjacent) modified amino acids. The alpha carbon of the core amino acid has side chains that are internal cross-links to the alpha carbons of other amino acids in the peptide, which can be saturated or not saturated. Amino acids cross-linked to the core amino acid can be separated from the core amino acid in either direction by 3 or 6 amino acids. The number of amino acids on either side of the core (e.g., between the core amino acid and an amino acid cross-linked to the core) can be the same or different.

As noted above an internal tether or cross-link can extend across the length of one helical turn (i.e., about 3.4 amino acids (i.e., i, i+4) or two helical turns (i.e., about 7 amino acids (i.e., i, i+7). Accordingly, amino acids positioned at i and i+4; or i and i+7 are candidates for chemical modification and cross-linking. Thus, for example, where a peptide has the sequence . . . $Xaa_1$, $Xaa_2$, $Xaa_3$, $Xaa_4$, $Xaa_5$, $Xaa_6$, $Xaa_7$, $Xaa_8$, $Xaa_9$ . . . , cross-links between $Xaa_1$ and $Xaa_5$, or between $Xaa_1$ and $Xaa_8$ are useful as are cross-links between $Xaa_2$ and $Xaa_6$, or between $Xaa_2$ and $Xaa_9$, etc.

The invention features a modified polypeptide of Formula (I),

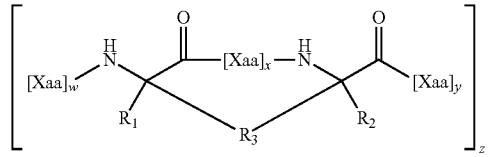

Formula (I)

or a pharmaceutically acceptable salt thereof, wherein;

each $R_1$ and $R_2$ are independently H or a $C_1$ to $C_{10}$ alkyl, alkenyl, alkynyl, arylalkyl, cycloalkylalkyl, heteroarylalkyl, or heterocyclylalkyl;

$R_3$ is alkylene, alkenylene or alkynylene (e.g., a $C_6$, $C_7$, $C_8$, $C_{11}$, $C_{12}$ or $C_{13}$ alkylene), or $[R_4'—K—R_4]_n$; each of which is substituted with 0-6 $R_5$;

$R_4$ and $R_4'$ are independently alkylene, alkenylene or alkynylene (e.g., each are independently a $C_1$, $C_2$, $C_3$, $C_4$, $C_5$, $C_6$, $C_7$, $C_8$, $C_9$ or $C_{10}$ alkylene, alkenylene or alkynylene);

$R_5$ is halo, alkyl, $OR_6$, $N(R_6)_2$, $SR_6$, $SO_2R_6$, $SO_2R_6$, $CO_2R_6$, $R_6$, a fluorescent moiety, or a radioisotope;

K is O, S, SO, $SO_2$, CO, $CO_2$, $CONR_6$, or

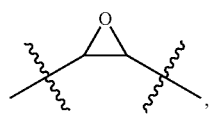 [SMILES: *C1OC1*]

aziridine, episulfide, diol, amino alcohol;
$R_6$ is H, alkyl, or a therapeutic agent;
n is 2, 3, 4 or 6;

x is an integer from 2-10 (e.g., 3 or 6);
w and y are independently an integer from 0-10 (e.g., 1, 2, 3, 4, 5, 6, 7, 8, 9, 10); and
each Xaa is independently an amino acid (e.g., one of the 20 naturally occurring amino acids or any naturally occurring non-naturally occurring amino acid);
wherein the polypeptide comprises at least 15 contiguous amino acids of SEQ ID NOs:1-32 or a variant thereof, or another polypeptide sequence described herein except that: (a) within the 15 contiguous (e.g., 15, 16, 17, 18, 19, 20, 21, 22, 23, 24, 24, 25, 26, 27, 28, 29, 30, 31, 32, 33, 34 or 35) amino acids of SEQ ID NO:1-32 the side chains of at least one pair (e.g., one or two pairs) of amino acids separated by 2, 3 or 6 amino acids is replaced by the linking group, $R_3$, which connects the alpha carbons of the pair of amino acids as depicted in Formula I; and (b) the alpha carbon of the first of the pair of amino acids is substituted with $R_1$ as depicted in formula I and the alpha carbon of the second of the pair of amino acids is substituted with $R_2$ as depicted in Formula I.

In another aspect, the invention features a modified polypeptide of Formula (II),

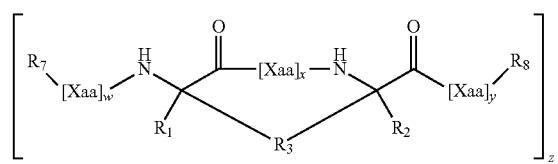

Formula (II)

or a pharmaceutically acceptable salt thereof,
wherein;
each $R_1$ and $R_2$ are independently H or a $C_1$ to $C_{10}$ alkyl, alkenyl, alkynyl, arylalkyl, cycloalkylalkyl, heteroarylalkyl, or heterocyclylalkyl;

$R_3$ is alkylene, alkenylene or alkynylene (e.g., a $C_6$, $C_7$, $C_8$, $C_{11}$, $C_{12}$ or $C_{13}$ alkylene) or $[R_4'—K—R_4]_n$; each of which is substituted with 0-6 $R_5$;

$R_4$ and $R_4'$ are independently alkylene, alkenylene or alkynylene (e.g., each are independently a $C_1$, $C_2$, $C_3$, $C_4$, $C_5$, $C_6$, $C_7$, $C_8$, $C_9$ or $C_{10}$ alkylene, alkenylene or alkynylene);

$R_5$ is halo, alkyl, $OR_6$, $NHR_6$, $N(R_6)_2$, $SR_6$, $SOR_6$, $SO_2R_6$, $CO_2R_6$, $R_6$, a fluorescent moiety, or a radioisotope;

K is O, S, SO, $SO_2$, CO, $CO_2$, $CONR_6$, or

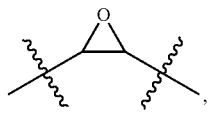

aziridine, episulfide, diol, amino alcohol, diamine;
$R_6$ is H, alkyl, or a therapeutic agent;
n is 2, 3, 4, 5, or 6;
x is an integer from 2-10 (e.g., 3 or 6);
w and y are independently an integer from 0-10 (e.g., 1, 2, 3, 4, 5, 6, 7, 8, 9, 10); and
each Xaa is independently an amino acid (e.g., one of the 20 naturally occurring amino acids or any naturally occurring non-naturally occurring amino acid);

R₇ is PEG, a tat protein, an affinity label, a targeting moiety, a fatty acid-derived acyl group, a biotin moiety, a fluorescent probe (e.g. fluorescein or rhodamine) linked via, e.g., a thiocarbamate or carbamate linkage; R₈ is H, OH, NH₂, NHR$_{8a}$, NR$_{8a}$R$_{8b}$;

wherein the polypeptide comprises at least 15 contiguous amino acids (e.g., 15, 16, 17, 18, 19, 20, 21, 22, 23, 24, 24, 25, 26, 27, 28, 29, 30, 31, 32, 33, 34 or 35) of SEQ ID NO: 1-32, or another polypeptide sequence described herein except that: (a) within the 15 contiguous amino acids of SEQ ID NO: 1-32 the side chains of at least one pair of amino acids separated by 2, 4 or 6 amino acids is replaced by the linking group, R₃, which connects the alpha carbons of the pair of amino acids as depicted in formula I; and (b) the alpha carbon of the first of the pair of amino acids is substituted with R₁ as depicted in Formula II and the alpha carbon of the second of the pair of amino acids is substituted with R₂ as depicted in Formula II.

In the case of Formula I or Formula II, the following embodiments are among those disclosed. In cases where x=2 (i.e., i+3 linkage), R3 can be a C7 alkylene, alkenylene. Where it is an alkenylene there can one or more double bonds. In cases where x=6 (i.e., i+4 linkage), R₃ can be a C11, C12 or C13 alkylene or alkenylene. Where it is an alkenylene there can one or more double bonds. In cases where x=3 (i.e., i+4 linkage), R₃ can be a C8 alkylene, alkenylene. Where it is an alkenylene there can one or more double bonds.

In certain instances, the two alpha, alpha disubstituted stereocenters (alpha carbons) are both in the R configuration or S configuration (e.g., i, i+4 cross-link), or one stereocenter is R and the other is S (e.g., i, i+7 cross-link). Thus, where Formula I is depicted as

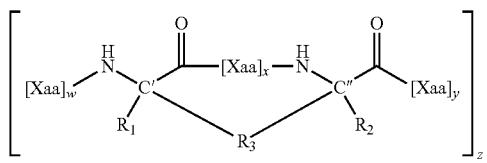

the C' and C" disubstituted stereocenters can both be in the R configuration or they can both be in the S configuration, for example when x is 3. When x is 6, the C' disubstituted stereocenter is in the R configuration and the C" disubstituted stereocenter is in the S configuration or the C' disubstituted stereocenter is in the S configuration and the C" disubstituted stereocenter is in the R configuration. The R₃ double bond may be in the E or Z stereochemical configuration. Similar configurations are possible for the carbons in Formula II corresponding to C' and C" in the formula depicted immediately above.

In some instances R₃ is [R₄—K—R₄']$_n$; and R₄ and R₄' are independently alkylene, alkenylene or alkynylene (e.g., each are independently a C1, C2, C3, C4, C5, C6, C7, C8, C9 or C10 alkylene, alkenylene or alkynylene In some instances, the polypeptide includes an amino acid sequence which, in addition to the amino acids side chains that are replaced by a cross-link, have 1, 2, 3, 4 or 5, 6, 7, 8, 9, 10, 11, 12 amino acid changes (e.g., conservative amino acid changes) in any of SEQ ID NOs: 1-32.

The tether can include an alkyl, alkenyl, or alkynyl moiety (e.g., C₆, C₈ or C₁₁ alkyl or a C₆, C₈ or C₁₁ alkenyl, or C₅, C₈ or C₁₁ alkynyl). The tethered amino acid can be alpha disubstituted (e.g., C₁-C₃ or methyl). [Xaa]$_y$ and [Xaa]$_w$ are peptides that can independently comprise at least 1, 2, 3, 4, 5, 6, 7, 8, 9, 10, 11, 12, 13, 14, 15, 16, 17, 18, 19, 20, 25, 26, 27, 28, 29, 30, 31, 32, 33, 34, or 35 contiguous amino acids of SEQ ID NOs: 1-32 and [Xaa]$_x$ is a peptide that can comprise 2, 3 or 6 contiguous amino acids of acids of SEQ ID NO: 1-32.

Peptides can contain one or more asymmetric centers and thus occur as racemates and racemic mixtures, single enantiomers, individual diastereomers and diastereomeric mixtures and geometric isomers (e.g. Z or cis and E or trans) of any olefins present. For example, peptides disclosed herein can exist in particular geometric or stereoisomeric forms, including, for example, cis- and trans-isomers, R- and S-enantiomers, diastereomers, (D)-isomers, (L)-isomers, the racemic mixtures thereof, and other mixtures thereof Enantiomers can be free (e.g., substantially free) of their corresponding enantiomer, and/or may also be optically enriched. "Optically enriched," as used herein, means that the compound is made up of a significantly greater proportion of one enantiomer. In certain embodiments substantially free means that a composition contains at least about 90% by weight of a preferred enantiomer. In other embodiments the compound is made up of at least about 95%, 98%, or 99% by weight of a preferred enantiomer. Preferred enantiomers may be isolated from racemic mixtures using techniques known in the art, including, but not limited to, for example, chiral high pressure liquid chromatography (HPLC) and the formation and crystallization of chiral salts or prepared by asymmetric syntheses (see, e.g., Jacques, et al, Enantiomers, Racemates and Resolutions (Wiley Interscience, New York, 1981); Wilen, S. H., et al., Tetrahedron 33:2725 (1977); Eliel, EX. Stereochemistry of Carbon Compounds (McGraw-Hill, NY, 1962); Wilen, S. H. Tables of Resolving Agents and Optical Resolutions p. 268 (EX. Eliel, Ed., Univ. of Notre Dame Press, Notre Dame, Ind. 1972). All such isomeric forms of these compounds are expressly included in the present invention.

Peptides can also be represented in multiple tautomeric forms, in such instances, the invention expressly includes all tautomeric forms of the compounds described herein (e.g., isomers in equilibrium (e.g., keto-enol), wherein alkylation at multiple sites can yield regioisomers), regioisomers, and oxidation products of the compounds disclosed herein (the invention expressly includes all such reaction products). All such isomeric forms of such compounds are included as are all crystal forms.

The symbol "⌇" when used as part of a molecular structure refers to a single bond or a trans or cis double bond.

The term "halo" refers to any radical of fluorine, chlorine, bromine or iodine. The term "alkyl" refers to a hydrocarbon chain that may be a straight chain or branched chain, containing the indicated number of carbon atoms. For example, C₁-C₁₀ indicates that the group may have from 1 to 10 (inclusive) carbon atoms in it. In the absence of any numerical designation, "alkyl" is a chain (straight or branched) having 1 to 20 (inclusive) carbon atoms in it. The term "alkylene" refers to a divalent alkyl (i.e., —R—).

The term "alkenyl" refers to a hydrocarbon chain that may be a straight chain or branched chain having one or more carbon-carbon double bonds in either Z or E geometric configurations. The alkenyl moiety contains the indicated number of carbon atoms. For example, C₂-C₁₀ indicates that the group may have from 2 to 10 (inclusive) carbon atoms in it. The term "lower alkenyl" refers to a C₂-C₈ alkenyl chain. In the absence of any numerical designation, "alkenyl" is a chain (straight or branched) having 2 to 20 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_2$-$C_{10}$ indicates that the group may have from 2 to 10 (inclusive) carbon atoms in it. The term "lower alkynyl" refers to a $C_2$-$C_8$ alkynyl chain. In the absence of any numerical designation, "alkynyl" is a chain (straight or branched) having 2 to 20 (inclusive) carbon atoms in it.

The term "aryl" refers to a 6-carbon monocyclic or 10-carbon bicyclic aromatic ring system wherein 0, 1, 2, 3, 4, or 5 atoms of each ring may be substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally may be optionally substituted. Preferred cycloalkyl groups include, without limitation, cyclopropyl, cyclobutyl, cyclopentyl, cyclopentenyl, cyclohexyl, cyclohexenyl, cyclohexadienyl, cycloheptyl, cycloheptadienyl, cycloheptatrienyl, cyclooctyl, cyclooctenyl, cyclooctadienyl, cyclooctatrienyl, and cyclooctynyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyrrolyl, pyridyl, furyl or furanyl, imidazolyl, 1,2,3-triazolyl, 1,2,4-triazolyl, benzimidazolyl, pyridazyl, pyrimidyl, thiophenyl, quinolinyl, indolyl, thiazolyl, oxazolyl, isoxazolyl and the like. The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, aziridinyl, oxiryl, thiiryl, morpholinyl, tetrahydrofuranyl, and the like.

The term "substituents" refers to a group "substituted" on an alkyl, cycloalkyl, aryl, heterocyclyl, or heteroaryl group at any atom of that group. Suitable substituents include, without limitation, halo, hydroxy, mercapto, oxo, nitro, haloalkyl, alkyl, alkaryl, aryl, aralkyl, alkoxy, thioalkoxy, aryloxy, amino, alkoxycarbonyl, amido, carboxy, alkanesulfonyl, alkylcarbonyl, azido, and cyano groups.

In some instances, the hydrocarbon tethers (i.e., cross links) described herein can be further manipulated. In one instance, a double bond of a hydrocarbon alkenyl tether, (e.g., as synthesized using a ruthenium-catalyzed ring closing metathesis (RCM)) can be oxidized (e.g., via epoxidation or dihydroxylation) to provide one of compounds below.

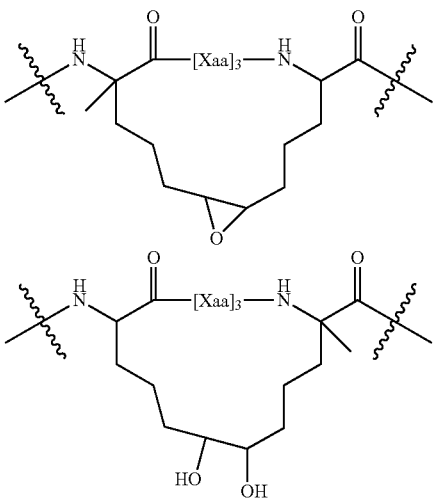

Either the epoxide moiety or one of the free hydroxyl moieties can be further functionalized. For example, the epoxide can be treated with a nucleophile, which provides additional functionality that can be used, for example, to attach a tag (e.g., a radioisotope or fluorescent tag). The tag can be used to help direct the compound to a desired location in the body or track the location of the compound in the body. Alternatively, an additional therapeutic agent can be chemically attached to the functionalized tether (e.g., an anti-cancer agent such as rapamycin, vinblastine, taxol, etc.). Such derivatization can alternatively be achieved by synthetic manipulation of the amino or carboxy-terminus of the polypeptide or via the amino acid side chain. Other agents can be attached to the functionalized tether, e.g., an agent that facilitates entry of the polypeptide into cells.

While hydrocarbon tethers have been described, other tethers are also envisioned. For example, the tether can include one or more of an ether, thioether, ester, amine, or amide moiety. In some cases, a naturally occurring amino acid side chain can be incorporated into the tether. For example, a tether can be coupled with a functional group such as the hydroxyl in serine, the thiol in cysteine, the primary amine in lysine, the acid in aspartate or glutamate, or the amide in asparagine or glutamine. Accordingly, it is possible to create a tether using naturally occurring amino acids rather than using a tether that is made by coupling two non-naturally occurring amino acids. It is also possible to use a single non-naturally occurring amino acid together with a naturally occurring amino acid.

It is further envisioned that the length of the tether can be varied. For instance, a shorter length of tether can be used where it is desirable to provide a relatively high degree of constraint on the secondary alpha-helical structure, whereas, in some instances, it is desirable to provide less constraint on the secondary alpha-helical structure, and thus a longer tether may be desired.

Additionally, while examples of tethers spanning from amino acids i to i+3, i to i+4; and i to i+7 have been described in order to provide a tether that is primarily on a single face of the alpha helix, the tethers can be synthesized to span any combinations of numbers of amino acids.

In some instances, alpha disubstituted amino acids are used in the polypeptide to improve the stability of the alpha helical secondary structure. However, alpha disubstituted amino acids are not required, and instances using mono-alpha substituents (e.g., in the tethered amino acids) are also envisioned.

The stapled polypeptides can include a drug, a toxin, a derivative of polyethylene glycol; a second polypeptide; a carbohydrate, etc. Where a polymer or other agent is linked to the stapled polypeptide is can be desirable for the composition to be substantially homogeneous.

The addition of polyethelene glycol (PEG) molecules can improve the pharmacokinetic and pharmacodynamic properties of the polypeptide. For example, PEGylation can reduce renal clearance and can result in a more stable plasma concentration. PEG is a water soluble polymer and can be represented as linked to the polypeptide as formula:

XO—$(CH_2CH_2O)_n$—$CH_2CH_2$—Y where n is 2 to 10,000 and X is H or a terminal modification, e.g., a $C_{1-4}$ alkyl; and Y is an amide, carbamate or urea linkage to an amine group (including but not limited to, the epsilon amine of lysine or the N-terminus) of the polypeptide. Y may also be a maleimide linkage to a thiol group (including but not limited to, the thiol group of cysteine). Other methods for linking PEG to a polypeptide, directly or indirectly, are known to those of ordinary skill in the art. The PEG can be linear or branched. Various forms of PEG including various functionalized derivatives are commercially available.

PEG having degradable linkages in the backbone can be used. For example, PEG can be prepared with ester linkages that are subject to hydrolysis. Conjugates having degradable PEG linkages are described in WO 99/34833; WO 99/14259, and U.S. Pat. No. 6,348,558.

In certain embodiments, macromolecular polymer (e.g., PEG) is attached to an agent described herein through an intermediate linker. In certain embodiments, the linker is made up of from 1 to 20 amino acids linked by peptide bonds, wherein the amino acids are selected from the 20 naturally occurring amino acids. Some of these amino acids may be glycosylated, as is well understood by those in the art. In other embodiments, the 1 to 20 amino acids are selected from glycine, alanine, proline, asparagine, glutamine, and lysine. In other embodiments, a linker is made up of a majority of amino acids that are sterically unhindered, such as glycine and alanine. Non-peptide linkers are also possible. For example, alkyl linkers such as —$NH(CH_2)_nC(O)$—, wherein n=2-20 can be used. These alkyl linkers may further be substituted by any non-sterically hindering group such as lower alkyl (e.g., $C_1$-$C_6$) lower acyl, halogen (e.g., Cl, Br), CN, $NH_2$, phenyl, etc. U.S. Pat. No. 5,446,090 describes a bifunctional PEG linker and its use in forming conjugates having a peptide at each of the PEG linker termini.

The stapled peptides can also be modified, e.g., to further facilitate cellular uptake or increase in vivo stability, in some embodiments. For example, acylating or PEGylating a peptidomimetic macrocycle facilitates cellular uptake, increases bioavailability, increases blood circulation, alters pharmacokinetics, decreases immunogenicity and/or decreases the needed frequency of administration. Therefore the compounds comprising a peptide disclosed herein can comprise a peptide that has been modified, e.g., to further facilitate cellular uptake or increase in vivo stability, in some embodiments.

In some embodiments, the stapled peptides disclosed herein have an enhanced ability to penetrate cell membranes (e.g., relative to non-stapled peptides).

Methods of synthesizing the compounds of the described herein are known in the art. Nevertheless, the following exemplary method may be used. It will be appreciated that the various steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 3d. Ed., John Wiley and Sons (1999); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof The peptides of this invention can be made by chemical synthesis methods, which are well known to the ordinarily skilled artisan. See, for example, Fields et al., Chapter 3 in Synthetic Peptides: A User's Guide, ed. Grant, W. H. Freeman & Co., New York, N.Y., 1992, p. 77. Hence, peptides can be synthesized using the automated Merrifield techniques of solid phase synthesis with the α-$NH_2$ protected by either t-Boc or Fmoc chemistry using side chain protected amino acids on, for example, an Applied Biosystems Peptide Synthesizer Model 430A or 431.

One manner of making of the peptides described herein is using solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Any side chain functional groups are protected with base stable, acid labile groups.

Longer peptides could be made by conjoining individual synthetic peptides using native chemical ligation. Alternatively, the longer synthetic peptides can be synthesized by well-known recombinant DNA techniques. Such techniques are provided in well-known standard manuals with detailed protocols. To construct a gene encoding a peptide of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

The peptides can be made in a high-throughput, combinatorial fashion, e.g., using a high-throughput multiple channel combinatorial synthesizer available from Advanced Chemtech.

Peptide bonds can be replaced, e.g., to increase physiological stability of the peptide, by: a retro-inverso bonds (C(O)—NH); a reduced amide bond (NH—$CH_2$); a thiomethylene bond (S—$CH_2$ or $CH_2$—S); an oxomethylene bond (O—$CH_2$ or $CH_2$—O); an ethylene bond ($CH_2$—$CH_2$); a thioamide bond (C(S)—NH); a trans-olefin bond (CH=CH); a fluoro substituted trans-olefin bond (CF=CH); a ketomethylene bond (C(O)—CHR) or CHR—

C(O) wherein R is H or $CH_3$; and a fluoro-ketomethylene bond $C(O)$—CFR or CFR—$C(O)$ wherein R is H or F or $CH_3$.

The polypeptides can be further modified by: acetylation, amidation, biotinylation, cinnamoylation, farnesylation, fluoresceination, formylation, myristoylation, palmitoylation, phosphorylation (Ser, Tyr or Thr), stearoylation, succinylation and sulfurylation. As indicated above, peptides can be conjugated to, for example, polyethylene glycol (PEG); alkyl groups (e.g., C1-C20 straight or branched alkyl groups); fatty acid radicals; and combinations thereof.

Therefore a compound comprising a polypeptide described herein can include a polypeptide that is modified by: acetylation, amidation, biotinylation, cinnamoylation, farnesylation, fluoresceination, formylation, myristoylation, palmitoylation, phosphorylation (Ser, Tyr or Thr), stearoylation, succinylation and sulfurylation. As indicated above, a compound comprising a polypeptide can include peptides that can be conjugated to, for example, polyethylene glycol (PEG); alkyl groups (e.g., C1-C20 straight or branched alkyl groups); fatty acid radicals; and combinations thereof.

α,α-Disubstituted non-natural amino acids containing olefinic side chains of varying length can be synthesized by known methods (Williams et al. J. Am. Chem. Soc., 113: 9276, 1991; Schafmeister et al., J. Am. Chem Soc., 122: 5891, 2000; and Bird et al., Methods Enzymol., 446:369, 2008; Bird et al, Current Protocols in Chemical Biology, 2011). For peptides where an i linked to i+7 staple is used (two turns of the helix stabilized) either one S5 amino acid and one R8 is used or one S8 amino acid and one R5 amino acid is used. R8 is synthesized using the same route, except that the starting chiral auxiliary confers the R-alkyl-stereoisomer. Also, 8-iodooctene is used in place of 5-iodopentene. Inhibitors are synthesized on a solid support using solid-phase peptide synthesis (SPPS) on MBHA resin (see, e.g., WO 2010/148335).

Fmoc-protected α-amino acids (other than the olefinic amino acids Fmoc-$S_5$—OH, Fmoc-$R_8$-OH, Fmoc-$R_8$—OH, Fmoc-$S_8$—OH and Fmoc-$R_5$—OH), 2-(6-chloro-1-H-benzotriazole-1-yl)-1,1,3,3-tetramethylaminium hexafluorophosphate (HCTU), and Rink Amide MBHA are commercially available from, e.g., Novabiochem (San Diego, Calif.). Dimethylformamide (DMF), N-methyl-2-pyrrolidinone (NMP), N,N-diisopropylethylamine (DIEA), trifluoroacetic acid (TFA), 1,2-dichloroethane (DCE), fluorescein isothiocyanate (FITC), and piperidine are commercially available from, e.g., Sigma-Aldrich. Olefinic amino acid synthesis is reported in the art (Williams et al., Org. Synth., 80:31, 2003).

In some instances, peptides can include a detectable label. As used herein, a "label" refers to a moiety that has at least one element, isotope, or functional group incorporated into the moiety which enables detection of the peptide to which the label is attached. Labels can be directly attached (ie, via a bond) or can be attached by a linker (e.g., such as, for example, a cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene, or any combination thereof, which can make up a linker). Labels can be attached to a peptide at any position that does not interfere with the biological activity or characteristic of the inventive polypeptide that is being detected.

Labels can include: labels that contain isotopic moieties, which may be radioactive or heavy isotopes, including, but not limited to, $^2H$, $^3H$, $^{13}C$, $^{14}C$, $^{15}N$, $^{31}P$, $^{32}P$, $^{35}S$, $^{67}Ga$, $^{99m}Tc$ (Tc-99m), $^{111}In$, $^{123}I$, $_{125}I$, $^{169}Yb$, and $^{186}Re$; labels that include immune orimmunoreactive moieties, which may be antibodies or antigens, which may be bound to enzymes (e.g., such as horseradish peroxidase); labels that are colored, luminescent, phosphorescent, or include fluorescent moieties (e.g., such as the fluorescent label FITC); labels that have one or more photoaffinity moieties; labels that have ligand moieties with one or more known binding partners (such as biotin-streptavidin, FK506-FKBP, etc.).

In some instances, labels can include one or more photoaffinity moieties for the direct elucidation of intermolecular interactions in biological systems. A variety of known photophores can be employed, most relying on photoconversion of diazo compounds, azides, or diazirines to nitrenes or carbenes (see, e.g., Bayley, H., Photogenerated Reagents in Biochemistry and Molecular Biology (1983), Elsevier, Amsterdam, the entire contents of which are incorporated herein by reference). In certain embodiments of the invention, the photoaffinity labels employed are o-, m- and p-azidobenzoyls, substituted with one or more halogen moieties, including, but not limited to 4-azido-2,3,5,6-tetrafluorobenzoic acid.

Labels can also be or can serve as imaging agents. Exemplary imaging agents include, but are not limited to, those used in positron emissions tomography (PET), computer assisted tomography (CAT), single photon emission computerized tomography, x-ray, fluoroscopy, and magnetic resonance imaging (MRI); anti-emetics; and contrast agents. Exemplary diagnostic agents include but are not limited to, fluorescent moieties, luminescent moieties, magnetic moieties; gadolinium chelates (e.g., gadolinium chelates with DTPA, DTPA-BMA, DOTA and HP-DO3A), iron chelates, magnesium chelates, manganese chelates, copper chelates, chromium chelates, iodine-based materials useful for CAT and x-ray imaging, and radionuclides. Suitable radionuclides include, but are not limited to, $^{123}I$, $^{125}I$, $^{130}I$, $^{131}I$, $^{133}I$, $^{135}I$, $^{47}Sc$, $^{72}As$, $^{72}Se$, $^{90}Y$, $^{88}Y$, $^{97}Ru$, $^{100}Pd$, $^{101}mRh$, $^{119}Sb$, $^{128}Ba$, $^{197}Hg$, $^{211}At$, $^{212}Bi$, $^{212}Pb$, $^{109}Pd$, $^{111}In$, $^{67}Ga$, $^{68}Ga$, $^{67}Cu$, $^{75}Br$, $^{77}Br$, $^{99}mTc$, $^{14}C$, $^{13}N$, $^{15}0$, $^{32}P$, $^{33}P$, and $^{18}F$.

Fluorescent and luminescent moieties include, but are not limited to, a variety of different organic or inorganic small molecules commonly referred to as "dyes," "labels," or "indicators." Examples include, but are not limited to, fluorescein, rhodamine, acridine dyes, Alexa dyes, cyanine dyes, etc. Fluorescent and luminescent moieties may include a variety of naturally occurring proteins and derivatives thereof, e.g., genetically engineered variants. For example, fluorescent proteins include green fluorescent protein (GFP), enhanced GFP, red, blue, yellow, cyan, and sapphire fluorescent proteins, reef coral fluorescent protein, etc. Luminescent proteins include luciferase, aequorin and derivatives thereof. Numerous fluorescent and luminescent dyes and proteins are known in the art (see, e.g., U.S. Patent Publication 2004/0067503; Valeur, B., "Molecular Fluorescence: Principles and Applications," John Wiley and Sons, 2002; and Handbook of Fluorescent Probes and Research Products, Molecular Probes, 9th edition, 2002).

Again, methods suitable for obtaining (e.g., synthesizing), stapling, and purifying the peptides disclosed herein are also known in the art (see, e.g., Bird et. al., Methods in Enzymol., 446:369-386 (2008); Bird et al, Current Protocols in Chemical Biology, 2011; Walensky et al., Science, 305:1466-1470 (2004); Schafineister et al., J. Am. Chem. Soc., 122:5891-5892 (2000); U.S. patent application Ser. No. 12/525,123, filed Mar. 18, 2010; and U.S. Pat. No. 7,723,468, issued May 25, 2010, each of which are hereby incorporated by reference in their entirety).

In some embodiments, the peptides are substantially free of non-stapled peptide contaminants or are isolated. Methods for purifying peptides include, for example, synthesizing the peptide on a solid-phase support. Following cyclization, the solid-phase support may be isolated and suspended in a solution of a solvent such as DMSO, DMSO/dichloromethane mixture, or DMSO/NMP mixture. The DMSO/dichloromethane or DMSO/NMP mixture may comprise about 30%, 40%, 50% or 60% DMSO. In a specific embodiment, a 50%/50% DMSO/NMP solution is used. The solution may be incubated for a period of 1, 6, 12 or 24 hours, following which the resin may be washed, for example with dichloromethane or NMP. In one embodiment, the resin is washed with NMP. Shaking and bubbling an inert gas into the solution may be performed.

Pharmaceutical Compositions

One or more of the stabilized peptides disclosed herein (e.g., one or more of SEQ ID NOs: 1-32) can be formulated for use as or in pharmaceutical compositions. Such compositions can be formulated or adapted for administration to a subject via any route, e.g., any route approved by the Food and Drug Administration (FDA). Exemplary methods are described in the FDA's CDER Data Standards Manual, version number 004 (which is available at fda.give/cder/dsm/DRG/drg00301.htm). For example, compositions can be formulated or adapted for administration by inhalation (e.g., oral and/or nasal inhalation (e.g., via nebulizer or spray)), injection (e.g., intravenously, intra-arterial, subdermally, intraperitoneally, intramuscularly, and/or subcutaneously); and/or for oral administration, transmucosal administration, and/or topical administration (including topical (e.g., nasal) sprays and/or solutions). In some instances, pharmaceutical compositions can include an effective amount of one or more stabilized peptides. The terms "effective amount" and "effective to treat," as used herein, refer to an amount or a concentration of one or more compounds or a pharmaceutical composition described herein utilized for a period of time (including acute or chronic administration and periodic or continuous administration) that is effective within the context of its administration for causing an intended effect or physiological outcome (e.g., treatment of cancer).

Pharmaceutical compositions of this invention can include one or more peptides and any pharmaceutically acceptable carrier and/or vehicle. In some instances, pharmaceuticals can further include one or more additional therapeutic agents in amounts effective for achieving a modulation of disease or disease symptoms.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, may also be advantageously used to enhance delivery of compounds of the formulae described herein.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intra-cutaneous, intra-venous, intra-muscular, intra-articular, intra-arterial, intra-synovial, intra-sternal, intra-thecal, intra-lesional and intra-cranial injection or infusion techniques.

Pharmaceutical compositions can be in the form of a solution or powder for inhalation and/or nasal administration. Such compositions may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

Pharmaceutical compositions can be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

Alternatively or in addition, pharmaceutical compositions can be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

In some embodiments, the present disclosure provides methods for using any one or more of the peptides or pharmaceutical compositions (indicated below as 'X') disclosed herein in the following methods:

Substance X for use as a medicament in the treatment of one or more diseases or conditions disclosed herein (e.g., cancer, referred to in the following examples as 'Y'). Use of substance X for the manufacture of a medicament for the treatment of Y; and substance X for use in the treatment of Y.

In some instances, one or more peptides disclosed herein can be conjugated, for example, to a carrier protein. Such conjugated compositions can be monovalent or multivalent. For example, conjugated compositions can include one peptide disclosed herein conjugated to a carrier protein. Alternatively, conjugated compositions can include two or more peptides disclosed herein conjugated to a carrier.

As used herein, when two entities are "conjugated" to one another they are linked by a direct or indirect covalent or non-covalent interaction. In certain embodiments, the association is covalent. In other embodiments, the association is non-covalent. Non-covalent interactions include hydrogen bonding, van der Waals interactions, hydrophobic interactions, magnetic interactions, electrostatic interactions, etc. An indirect covalent interaction is when two entities are covalently connected, optionally through a linker group.

Carrier proteins can include any protein that increases or enhances immunogenicity in a subject. Exemplary carrier proteins are described in the art (see, e.g., Fattom et al., Infect. Immun., 58:2309-2312, 1990; Devi et al., Proc. Natl. Acad. Sci. USA 88:7175-7179, 1991; Li et al., Infect. Immun. 57:3823-3827, 1989; Szu et al., Infect. Immun. 59:4555-4561,1991; Szu et al., J. Exp. Med. 166:1510-1524, 1987; and Szu et al., Infect. Immun. 62:4440-4444, 1994). Polymeric carriers can be a natural or a synthetic material containing one or more primary and/or secondary amino groups, azido groups, or carboxyl groups. Carriers can be water soluble.

Methods of Treatment

The disclosure includes methods of using the peptides herein for the prophylaxis and/or treatment of cancer. The terms "treat" or "treating," as used herein, refers to partially or completely alleviating, inhibiting, ameliorating, and/or relieving the disease or condition from which the subject is suffering.

In general, methods include selecting a subject and administering to the subject an effective amount (e.g. a therapeutically effective amount) of one or more of the peptides herein, e.g., in or as a pharmaceutical composition, and optionally repeating administration as required for the prophylaxis or treatment of a cancer.

Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

EXAMPLES

Example 1: Identification and Characterization of Mcl-1 Specific Peptides

Three Mcl-1-specific peptides were discovered while screening a yeast surface display library of Bim-BH3 domain variants. BH3 sequences from two clones (B3 and A12) were chosen for further study as soluble peptides. Synthetic peptides of 23 amino acids with the sequences of B3 and A12 and an N-terminal fluorescein were made and tested in solution for binding to KSBcl-2 and five human Bcl-2 family proteins (FIG. 1; see Table 1 for all sequences). These experiments showed that the identified peptides that bound to KSBci-2 and Mcl-1 in preference to Bcl-2, Bfl-1, Bcl-w, and to a lesser extent Bcl-xL.

TABLE 1

Sequences of Peptides Used for Fluorescence Anisotropy and BH3 Profiling Assays

| Peptides | Sequence<br>    2      3      4<br>abcdefgabcdefgabcdefg |
|---|---|
| MS1 | RPEIWMTQGLRRLGDEINAYYAR |
| MS2 | RPEIWLTQSLQRLGDEINAYYAR |
| MS3 | RPEIWLTQHLQRLGDEINAYYAR |
| A12 | RPEIWMGQGLRRLGDEINAYYAR |
| B3 | RPEIWLGQSLQRLGDEINAYYAR |
| G9 | RPEIWLGQHLQRLGDEINAYYAR |
| NoxaA | AELPPEFAAQLRKIGDKVYC |
| Bim | RPEIWIAQELRRIGDEFNAYYAR |
| Bim_A2eT | RPEIWIT̲QELRRIGDEFNAYYAR |
| Bim_A2eT_12dM | RPEIWM̲T̲QELRRIGDEFNAYYAR |
| Bim_A2eT_E2gG | RPEIWIT̲QG̲LRRIGDEFNAYYAR |
| Bim_A2eT_I3dL | RPEIWIT̲QELRR̲L̲GDEFNAYYAR |
| Bim_A2eT_F4al | RPEIWIT̲QELRRIGDE̲I̲NAYYAR |

Because the peptides we identified bound tightly to Mcl-1 and showed good specificity for Mcl-1 over other human Bcl-2 family members, we chose to develop them further as Mcl-1 binders.

Figure 2:
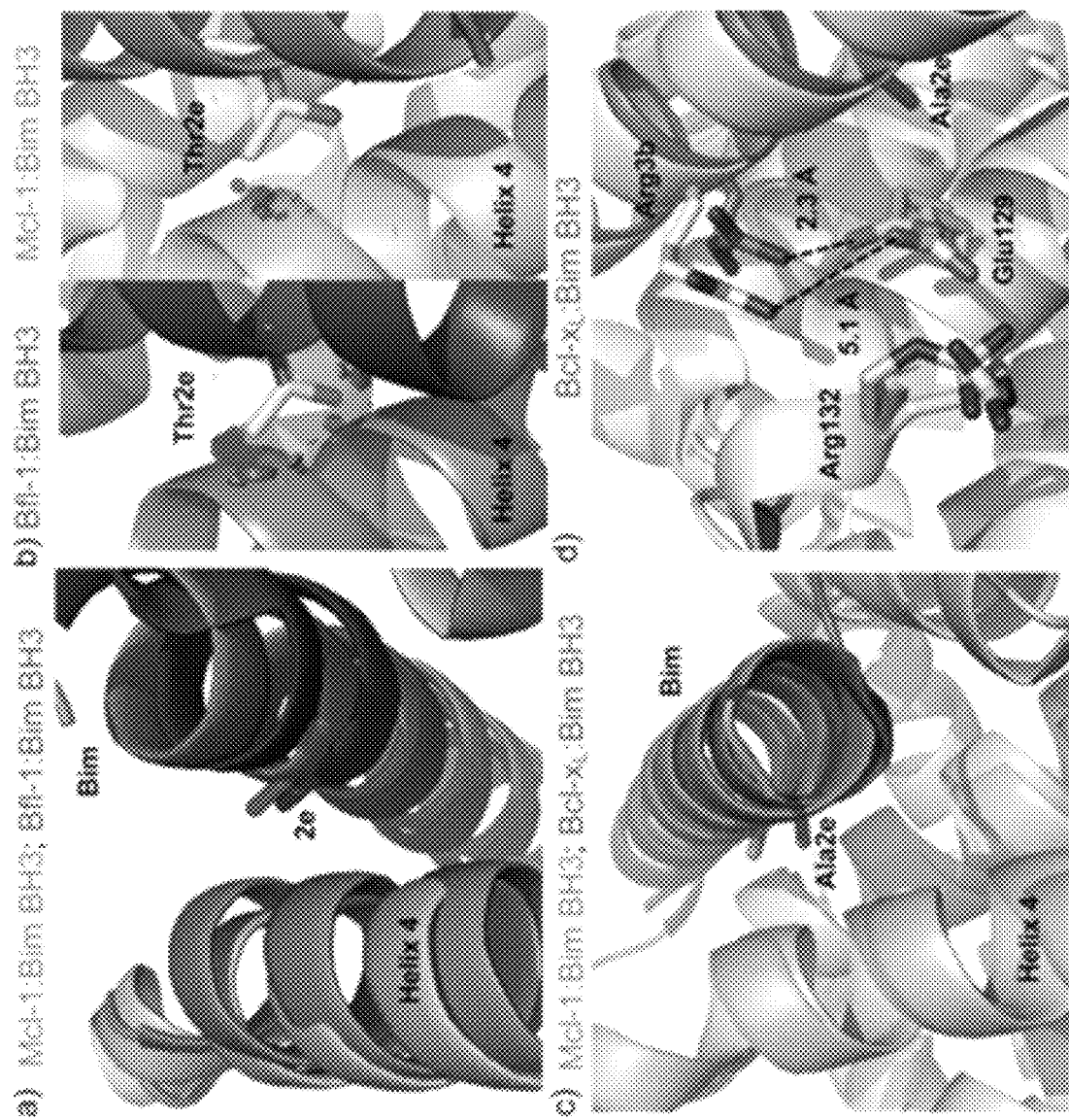
FIG. 2|Modeling of binding of peptides.

We sought to improve the Mcl-1 binding selectivity of peptides identified in screening using rational mutagenesis. Wild-type Bim has an alanine at position 2e (see Table 1 for peptide position labels), and SPOT-array tests of Bim BH3 point mutants have shown that glycine at 2e, found in B3, A12, and G9 (a point mutant of B3 that was also identified in screening), is tolerated by or increases binding to all of the receptors. Threonine at 2e was identified using SPOT arrays as a mutation that could decrease binding to Bfl-1, Bcl-xL, Bcl-2, and Bcl-w, while maintaining strong binding to Mcl-1. The specificity of peptides corresponding to B3, A12, and G9 was greatly improved by replacing the glycine at the 2e position with a threonine, generating the MS1, MS2, and MS3 variants (for Mcl-1 specific), corresponding to the sequences of A12, B3, and G9 with a G2eT mutation, respectively. MS1, MS2, and MS3 labeled with an N-terminal fluorescein were tested for binding to the five human Bcl-2 receptors in fluorescence anisotropy assays. As shown in FIG. 1, all three peptides bound Mcl-1 with Kd≤2 nM. MS1 bound with Kd>1 µM to the other four receptors. MS2 bound with micromolar affinity to Bcl-xL, Bcl-2, and Bfl-1 and bound in the hundred-nanomolar range to Bcl-w. MS3 also displayed micromolar affinity for Bcl-xL and Bcl-2 and several-hundred nanomolar affinity to Bcl-w and Bfl-1. In contrast, the NoxaA BH3 peptide from murine Noxa, for which no binding up to 2500 nM for Bcl-xL, Bcl-2, Bcl-w, or Bfl-1 is reported in the literature, bound Mcl-1 more weakly than the three designed peptides, with a Kd of 46 nM (FIG. 1). NoxaA is the most Mcl-1-selective natural BH3, and a NoxaA BH3 peptide is routinely used in BH3 profiling assays to detect apoptotic resistance dependent upon Mcl-1. Compared to NoxaA, the three designed peptides MS1, MS2 and MS3 have high affinity for Mcl-1 and also show high specificity against Bcl-xL, Bcl-2, Bcl-w, and Bfl-1. To assess the influence of the N-terminal fluorescein dye on binding, we tested a subset of unlabeled peptides, MS1, MS2, Bim, and NoxaA in competition with a fluorescently labeled Bim variant. The Ki values for Mcl-1 binding to MS1, MS2, and NoxaA were weaker than the Kd values determined using labeled peptides. The Ki for MS1 binding to Mcl-1 was between 8 and 24 nM, depending on the fitting. The competition experiments indicated that MS1 is between ~40- and 190-fold specific for Mcl-1 over Bcl-w, the next-tightest binding family member. Competition experiments also confirmed that MS1 and MS2 are considerably tighter binders to Mcl-1 than is NoxaA; NoxaA binding to Mcl-1 was very weak and thus difficult to quantify with the competition assay. A peptide corresponding to the BH3 region of Bim binds very tightly to all receptors. To better understand the determinants of binding specificity for MS1, MS2, and MS3, we sought to identify residues in these peptides that differ from Bim and destabilize interactions with receptors other than Mcl-1. The 2eT mutation was vital in generating highly Mcl-1-specific peptides. This single point mutation in Bim (giving Bim_A2eT, Table 1) provides a 6-fold reduction in Bcl-xL binding and over 20-fold reduction in Bcl-2, Bcl-w, and Bfl-1 binding in a peptide with the wild-type Bim background (FIG. 1). Likewise, introducing 2eT into library peptides A12 and B3 reduced binding to Bfl-1, Bcl-2, and Bcl-xL by ~100-fold and gave a more moderate ~10-fold reduction in Bcl-w binding affinity. Thus, it is clear that threonine at position 2e is highly destabilizing for all human Bcl-2 receptors other than Mcl-1, in several different peptide contexts. Position 2e is conserved as small (alanine, glycine, serine) in natural BH3 sequences. Mcl-1 can bind BH3 peptides with larger residues at position 2e, including Bim_A2eT and a peptide corresponding to the Mcl-1 BH3 region, which has a leucine at position 2e. To look for possible reasons that the other Bcl-2 paralogs cannot accommodate threonine at position 2e, we compared structures of Bcl-xL, Bfl-1, and Mcl-1 bound to the BH3 region of Bim (3FDL, 2VM6, and 2PQK, respectively). As shown in FIG. 2a, helix 4 of Bfl-1 is closer to the peptide near the 2e position than is helix 4 in Mcl-1. Simple modeling of preferred threonine rotamers at 2e on static Mcl-1:Bim BH3 and Bfl-1:Bim BH3 structures illustrates that threonine is easily accommodated in the Mcl-1 structure in Bfl-1 (FIG. 2b). In the Bcl-xL:Bim BH3 structure, the BH3 peptide is positioned slightly differently in the groove, resulting in Ala2e being oriented further into the groove than in the Mcl-1:Bim BH3 structure (FIG. 2c). Rearrangement of Bcl-xL helix 4 would likely be required to accommodate threonine, and such rearrangement could be disfavored if it led to disruption of a three-residue salt-bridge network that forms in the Bcl-xL:Bim BH3 structure between Glu129 and Arg132 of Bcl-xL (on helix 4) and Arg3b of Bim (FIG. 2d). This network cannot be formed in a structure like that of Mcl-1:Bim BH3 or Mcl-1:Mcl-1 BH3 (in which position 2e is leucine), because the equivalent of Bcl-xL residue 129 is farther away from peptide position 3b in this complex. The charged residues in Bcl-xL that participate in salt-bridge formation are also conserved in Bcl-2, suggesting that a similar mechanism might operate to disfavor threonine or larger residues at 2e for that protein. MS1, MS2, and MS3 all have different substitutions at 2g, which is a glutamate in wild-type Bim and is typically a medium-to-large residue in other known BH3 regions. MS1, our most selective peptide, has a glycine at this position, and mutating glutamate to glycine at position 2g in Bim_A2eT decreased binding to all receptors. The change in affinity for Mcl-1 could not be quantified, but affinities for Bfl-1, Bcl-2, Bclw, and Bcl-xL were reduced an additional 2-8 fold-compared to Bim_A2eT. Thus, glycine at 2g provides some of the negative design disfavoring interactions with off-target receptors, although at the cost of weakening binding to the Mcl-1 target (FIG. 1). Three mutations in peptides MS1, MS2, and MS3 occur in positions that are usually conserved as hydrophobic in known BH3 motifs (positions 2d, 3d, and 4a). When tested in the Bim_A2eT context, I2dM (found in MS1) provided a roughly 4-fold reduction in binding to Bcl-xL, Bcl-2, Bcl-w, and Bfl-1 (FIG. 1). Notably, significant decreases in Bcl-w binding for Bim_A2eT_E2gG and Bim_A2eT_I2dM may explain why MS1 is more selective for Mcl-1 vs Bcl-w than are MS2 and MS3, which have different mutations at 2g and 2d. Mutation I3dL reduced binding of Bim_A2eT to Bfl-1 by 4-fold, while this mutation increased binding slightly to Bcl-xL, Bcl-2, and Bcl-w (FIG. 1). The F4aI mutation increased Bim_A2eT binding slightly to Bfl-1 and Bcl-w but decreased binding by 6- and 3-fold to Bcl-xL and Bcl-2, respectively (FIG. 1). Position 4a is a well-documented source of specificity for Mcl-1 binding. Mutagenesis studies and peptide library screens have demonstrated that Bcl-xL binds preferentially to peptides that include a phenylalanine or tyrosine to fill the enclosed hydrophobic pocket near 4a, whereas Mcl-1 tolerates a wide variety of substitutions at this position.

Figure 3:
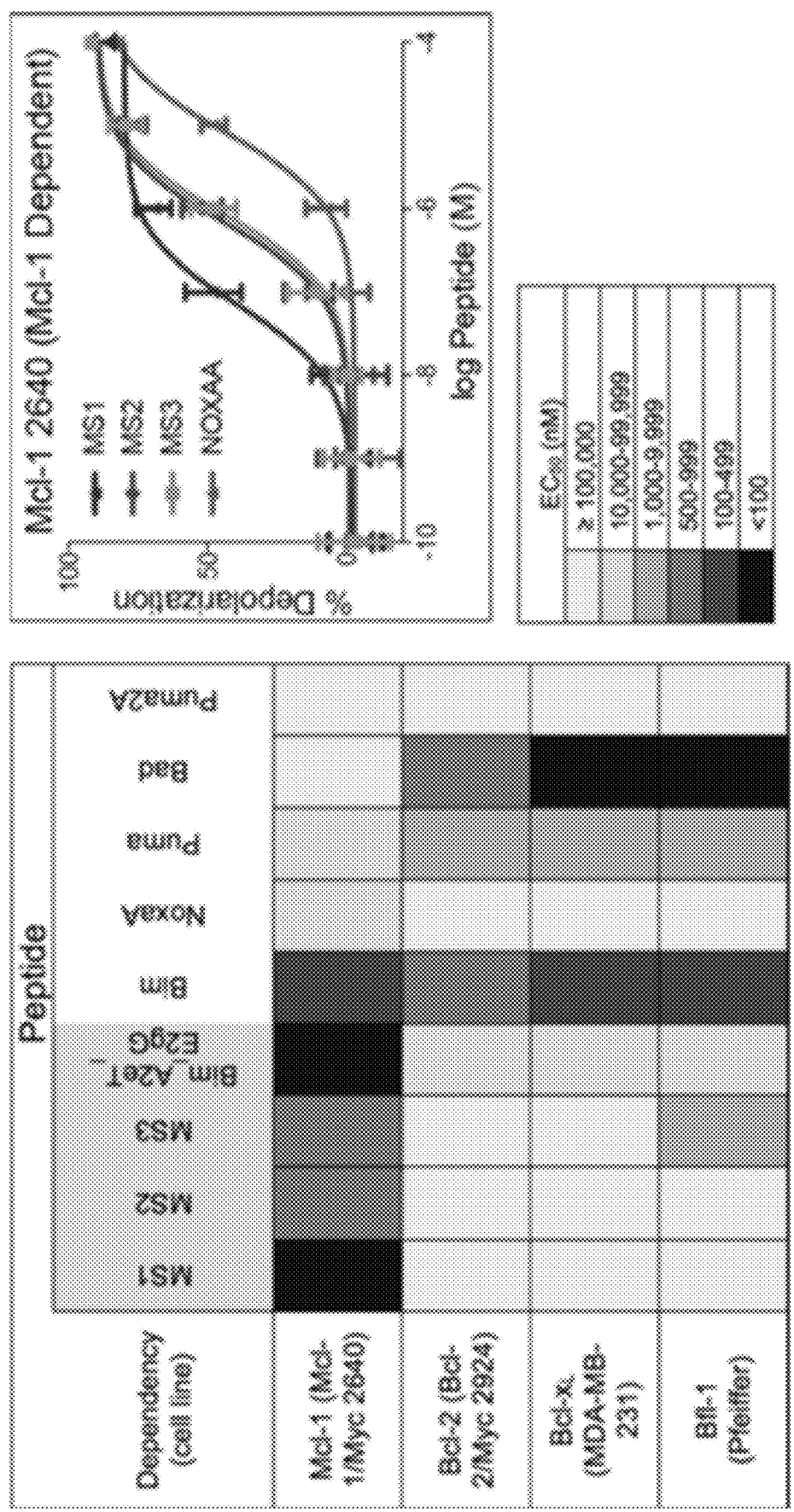
FIG. 3|Results of BH3 profiling studies.

A whole-cell BH3 profiling assay was used to test the specificity of our Mcl-1-binding peptides in several cell lines with differing dependencies on Bcl-2, Mcl-1, Bcl-xL, or Bfl-1. In this assay, permeabilized cells were treated with increasing doses of BH3 peptides, and mitochondrial outer membrane permeabilization (MOMP) was monitored using the dye JC-1 (see below). EC50 values for BH3 profiling experiments involving peptides from this study are given in FIG. 3. Mcl-1/Myc 2640 is an engineered murine leukemia cell line overexpressing murine Mcl-1 and Myc, and Bcl-2/Myc 2924 is a similarly engineered cell line overexpressing human Bcl-2. By Western blot and BH3 profiling, these cells exhibit Mcl-1 and Bcl-2 dependencies, respectively. MS1, MS2, and MS3 elicited potent mitochondrial depolarization responses in Mcl-/Myc 2640, with EC50 values of 70 nM, 700 nM, and 860 nM, respectively. These peptides were much more potent than NoxaA in this assay (EC50=20 µM). Human and murine Mcl-1 are over 90% identical in the Bcl-2 domain and 94% identical in the BH3 binding groove. Human multiple myeloma cell lines dependent upon Mcl-1 (as indicated by response to NoxaA and Bad) gave EC50 values of 2.5-3.3 µM for MS1, compared to EC50 values>100 µM for NoxaA. Thus, multiple Mcl-1-dependent cell lines were much more sensitive to MS1 than to NoxaA. MS1 and MS2 were highly selective in BH3 profiling. In a Bcl-2-dependent line, EC50 values were >100 µM for MS1, MS2, MS3, and NoxaA. MDA-MB-231 is a human breast cancer cell line that has been shown to have a Bcl-xL-dependent profile. EC50 values for MS1, MS2, MS3, and NoxaA were over 100 µM for MDA-MB-231 cells. MS1 and MS2 showed EC50 values>100 µM in Pfeiffer, a lymphoma line with high Bfl-1 mRNA expression that has previously been shown to exhibit a Bfl-l-dependent BH3 profile. MS3 gave a stronger response in Pfeiffer than MS1 or MS2, but MS3 also exhibited tighter Bfl-1 binding by fluorescence anisotropy (FIG. 1). Finally, Bim_A2eT_E2gG, which showed modest specificity for Mcl-1 by fluorescence anisotropy (FIG. 1), exhibited a strong depolarization response in Mcl-1/Myc 2640 and a depolarization response intermediate to that of Bim and MS1 in Bcl-2/Myc 2924, MDA-MB-231, and Pfeiffer. Thus, in vitro binding specificities are replicated in BH3 profiling assays in cell lines showing all of the currently identified dependencies on Bcl-xL, Bcl-2, Mcl-1, and Bfl-1, as a Bcl-w-dependent cell line has not yet been identified or constructed. The engineered peptides tested here were derived from Bim BH3, which is an activator BH3 peptide. Nevertheless, these peptides did not cause strong depolarization in cell lines that are not dependent upon Mcl-1, indicating that they act as sensitizers rather than activators in these assays. Depolarization activity was specific to the Bcl-2 pathway, because the peptides did not depolarize mitochondria in the Bax/Bak-deficient cell line Su-DHL10.

Cellular BH3 Profiling Assay

Assay plates were produced by serial dilution of each peptide from 200 µM to 0.2 nM using 10-fold dilutions in DTEB (Derived from Trehalose Experimental Buffer: 135 mM trehalose, 50 mM KCl, 20 µM EDTA, 20 µM EGTA, 0.1% BSA, 5 mM succinate, 10 mM HEPES-KOH pH 7.5) containing 0.005% w/v digitonin, 10 mM 2-mercaptoethanol, 2 µM JC-1, and 20 mg mL-1 oligomycin. Triplicate wells for each peptide were made for each cell line by adding 15 µL of the peptide dilutions to each well of a black, untreated 384-well plate. Control wells containing no peptide or 20 µM FCCP (carbonyl cyanide-4(trifluoromethoxy) phenylhydrazone, a chemical uncoupler of oxidative phosphorylation) were included for zero and complete depolarization, respectively. Multiple plates were produced from the same stock and frozen at −80 ° C. for later use. Frozen plates were brought to RT prior to use, cells were suspended in DTEB at a density of 1.34×106 cells/mL, and 15 µL of cell suspension was added to each well of the dilution series to yield wells ranging from 0.1 nM to 100 µM peptide and 20000 cells/well. Fluorescence of JC-1 aggregates was measured at 590 nm with 545 nm excitation on a Tecan Safire2 at 5 min intervals for 3 h. The area under each signal-vs-time curve was calculated and normalized to the untreated and FCCP values to produce the percent depolarization. Curves were plotted as the log [peptide] vs percent depolarization, with sigmoidal dose—response curves fitted using Graphpad PRISM 6. For curves without an upper baseline, an upper limit on the EC50 was estimated by fitting the curve with the upper baseline fixed at 100% depolarization, as this was the upper limit reached by most curves with a complete upper baseline.

Example 2: Stabilized Peptides Retain Selectivity

Internal cross-links were used to create a number of stabilized variants of a peptide (M1), related to MS1, and having the sequence:

IWNleTQGLRRLGDEINAYYARR. (SEQ ID NO: 6)

as follows:

M1 SAHBa:
IWNleTQGLRXLGDXINAYYARR (SEQ ID NO: 7)

M1 SAHBd:
IWNleXQGLXRLGDEINAYYARR (SEQ ID NO: 9)

M1 SAHBf:
IWNleTQGLRRLGDEIXAYYXRR (SEQ ID NO: 8)

Figure 4:
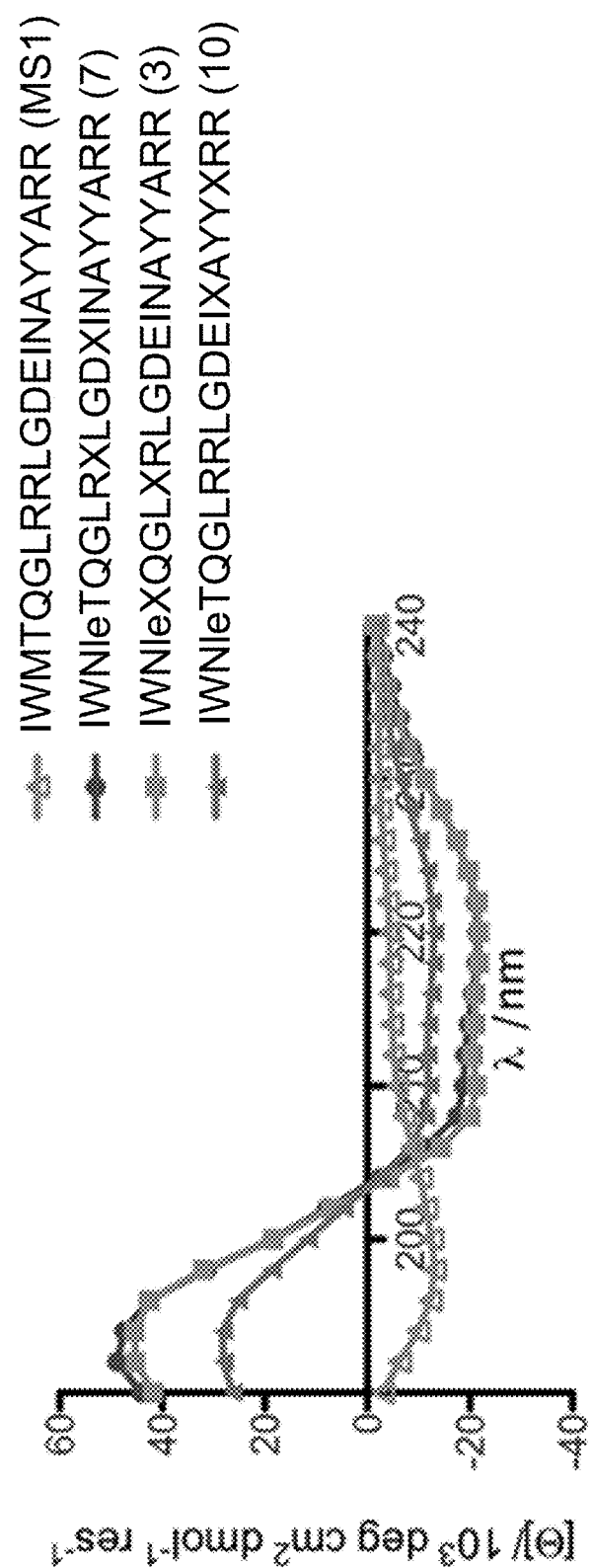
FIG. 4|Results of studies assessing the alpha-helicity of various internally cross-linked peptides. Circular dichroism analysis illustrating helicity of stapled peptides 3 (SEQ ID NO:9), 7 (SEQ ID NO:7), and 10 (SEQ ID NO:8) and the non-stapled peptide of the amino acid sequence IWMTQGLRRLGDEINAYYARR (SEQ ID NO:54), dissolved in Tris buffer pH.7.4.

As shown in FIG. 4, peptide 3 (SEQ ID NO:9) (M1 SAHBd) exhibited the highest alpha-helical content. As shown in Table 2, this peptide also appeared to have the greatest selectivity for Mcl-1 over Bcl-xL, Bcl-2, Bclw and Bfl 1.

TABLE 2

| Peptide | IC$_{50\%}$ (95% confidence interval) Receptor | |
|---|---|---|
| | Mcl-1 | BclxL Bcl-2 Bclw Bfl1 |
| M1 | 2982 ± 220 | >10000 |
| M1 SAHBa | 757 ± 15 | >10000 |
| M1 SAHBd | 90 | >10000 |
| M1 SAHBf | 859 ± 22 | >10000 |

Figure 5:
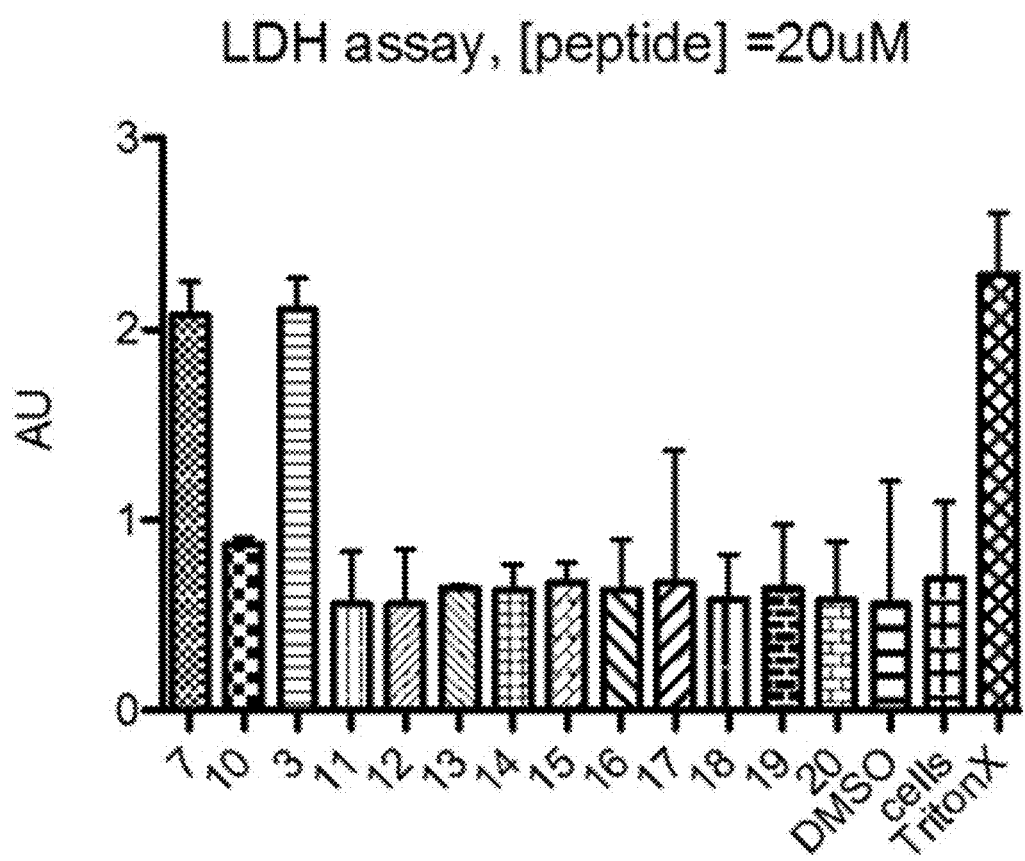
FIG. 5|Results of studies assessing non-specific cell-lysis by internally cross-linked peptides. Lactate dehydrogenase release assays (LDH) identified membrane-disruptive peptides 3 (SEQ ID NO:9) and 7 (SEQ ID NO:7); tested in MEF cells. Peptides 7, 10, 3, and 11-20 are SEQ ID NOs: 7, 8, 9, and 10-19 respectively.

Additional studies examined the non-specific cell lysis activity of peptide 3 (SEQ ID NO:9) (M1 SAHBd) and certain sequence variants of peptide 3 (SEQ ID NO:9) (M1 SAHBd). The results of this analysis are presented in FIG. 5.

Further studies examined the cellular uptake of M1 SAHBd and a number of sequence variants, including length variants. The various stabilized peptides (M2 SAHBd-M11 SAHBd) (SEQ ID NOs:10-19), all retaining the same internal cross-link present in M1 SAHBd, varied in net charge. As shown in FIG. 6, certain alterations improved cell uptake but reduced affinity to Mcl-1.

Next, a whole-cell BH3 profiling assay (described above) was used to test the specificity of our Mcl-1-binding peptides in several cell lines with differing dependencies on Bcl-2, Mcl-1, Bcl-xL/Bcl-xL, or Bfl-1. In this assay, permeabilized cells were treated with increasing doses of stabilized peptides, and mitochondrial outer membrane permeabilization (MOMP) was monitored using the dye JC-1. The results of the analysis are present in FIG. 7 which shows that select peptides are more specific for Bcl-2 than the BH3 domain of BIM, BID, PUMA, BMF, NOXA, MS1 and HRK.

Example 3: Additional Stabilized Peptides with Mcl-1 Specificity

An additional peptide, B1 having the sequence IWFAQEIDRIGDEVNAYYARR (SEQ ID NO:23) was stabilized by the insertion of an internal cross at position A, position F, or position D to create three different stabilized peptides, B1 SAHBa, B1 SAHBf and B1 SAHBd. Cellular uptake was assessed for each stabilized peptide and the native B1 peptide. In addition two variants of B1, differing in length from B1 were created: IWFAQEIDRIGDEVNAY-
YAR (B2; SEQ ID NO:31) and EIWFAQEIDRIGDEVNAY-
YAR (B3; SEQ ID NO:32).

Cellular uptake of the stabilized variants of B2 and B3, each having an internal cross-link at position D was assessed. The results of this study is presented in FIG. 8, where higher values for cellular average intensity indicate greater cell permeability and X indicates the amino acids whose side chain has been replace by a hydrocarbon internal cross-link.

The above-described variants of peptide B1 were also analyzed for binding specificity alongside two additional variants of B1 having an internal cross-link at either position G (IWFAXEIDXIGDEVNAYYARR; B1 SAHBg; SEQ ID NO:29) or position H (XWFAQEIXRIGDEVNAYYARR; B1 SAHBh; SEQ ID NO:30) and peptides corresponding to the BH3 domain of BIM, BID, PUMA, BMF, NOXA, MS1 and HRK using the a whole-cell BH3 profiling assay (described above). The results of the analysis are presented in FIG. 9.

Figure 10A:
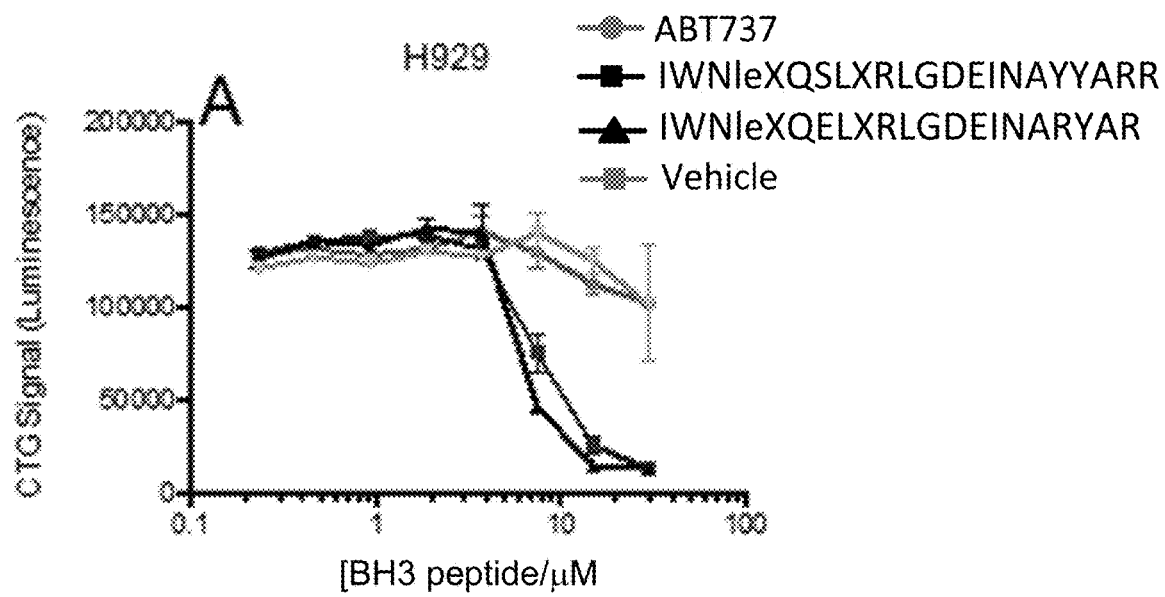
FIG. 10A. shows the results of a cell viability assay in Mcl-1-dependent H929 multiple myeloma cells.
Figure 10B:
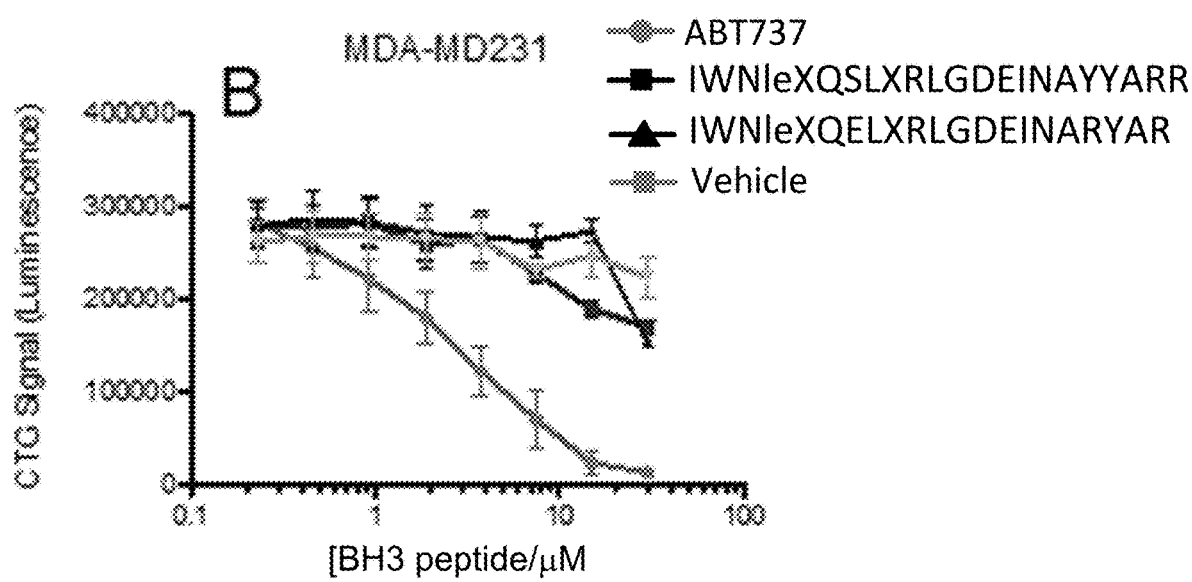
FIG. 10B. shows the results of a cell viability assay in $Bcl_{XL}$-dependent MDA-MB231.

Example 4: Quantification of Cell-Killing Potential of Peptides with Mcl-1 Specificity The function of peptides with Mcl-1 specificity was quantified in cells; we assayed peptides for the cell killing that depends on Mcl-1 inhibition (FIG. 10). The effect of engineered stapled peptides on cell viability was assessed with cell lines engineered to be dependent on Bcl-$_{XL}$ or Mcl-1 for survival. This was performed because cancer cells are often redundantly protected by multiple Bcl-2 family members, and in this experiment our goal was to engineer Mcl-1 selective inhibitors that are less effective against Bcl-$x_L$ or other anti-apoptotic family members (for many of which selective inhibitors already exist). We used H929 (FIG. 10A) and MDA-MB231 (FIG. 10B) cells, for which survival is dependent on over-expression of Mcl-1 or Bcl-$_{XL}$, respectively. Treatment of Mcl-1 expressing cells (H929) with Mcl-1 selective inhibitors (IWNleXQSLXRLGDEIN-AYYARR (SEQ ID NO:14) and IWNleXQELXRLGDEIN-ARYAR (SEQ ID NO:18)) resulted in dose-dependent cell killing, as assessed by CellTiter-Glo (CTG) (Promega) luminescence. These peptides induced rapid killing of the cells with IC50 values as low as 4-7 µM in H929 cells whereas these peptides remained inactive in MDA-MB23. Bcl-2 selective inhibitor ABT-737 served as a control. This compound is not active in H929 but caused a clear dose-dependent reduction in cell viability in MDA-MB231.

Cell viability was measured by CTG assay at 24 hours in the presence of increasing concentration of ABT 737, IWN-leXQSLXRLGDEINAYYARR (SEQ ID NO:14) and IWN-leXQELXRLGDEINARYAR (SEQ ID NO:18) in BclxL-dependent MDA-MB231 (FIG. 10B) and Mcl-1-dependent H929 multiple myeloma cells (FIG. 10A). Data are mean and s.d. for experiments performed in at least duplicate. Vehicle is DMSO.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound comprising an internally cross-linked polypeptide comprising the amino acid sequence:

F1 G1 A2 B2 C2 D2 E2 F2 G2 A3 B3 C3 D3 E3 F3 G3 A4 B4 C4 D4 E4 F4 G4 A5, (SEQ ID NO: 1)

wherein:
F1 is R or is missing;
G1 is P or is missing;
A2 is E or is missing;
B2 is I;
C2 is W;
D2 is M, L, F, I, or norleuicine (Nle);
E2 is T, A, V, or Aib;
F2 is Q, or R;
G2 is G, H, E, or S;
A3 is L, or I;
B3 is R, D, Q, Aib, or Me-Leu;
C3 is R;
D3 is L, or I;
E3 is G;
F3 is D;
G3 is E;
A4 is I, V, or F;
B4 is N;
C4 is A;
D4 is Y or R;
E4 is Y;
F4 is A or is missing;
G4 is R or is missing;
A5 is R or is missing; and
the side chains of two amino acids separated by two, three or six amino acids are replaced by an internal cross-link; the side chains of three amino acids are replaced by an internal stitch; the side chains of four amino acids are replaced by internal cross-links or internal stitches,; or the side chains of at least four amino acids are replaced by internal cross-links, internal stitches, or a combination of internal cross-links and stitches, wherein the cross-link is between the alpha carbons of: E2 and B3; F2 and C3; or B4 and F4.

2. The compound of claim 1 wherein the side chains of two amino acids separated by 3 or 6 amino acids are replaced by an internal cross-link.

3. The compound of claim 2 wherein the internal cross-link is an alkylene or alkenylene group.

4. The compound of claim 3 wherein the alkylene or alkenylene is a C7, C8, C9, C10, C11, C12 or C13 alkylene or alkenylene.

5. A compound comprising a polypeptide having a sequence selected from the group consisting of:

RPEIWMTQGLRRLGDEINAYYAR, (SEQ ID NO: 2)

IWNleTQGLRRLGDEINAYYARR, (M1; SEQ ID NO: 6)

and

IWFAQEIDRIGDEVNAYYARR; (B1; SEQ ID NO: 23)

wherein: none or one, of the amino acids are replaced by another amino acid, and the side chains of two amino acids are replaced by an internal crosslink, wherein the cross-link is between the alpha carbons of: E2 and B3; F2 and C3; or B4 and F4.

6. The compound of claim 1 comprising a peptide selected from:

RPEIWMXQGLXRLGDEINAYYA; (SEQ ID NO: 3)

RPEIWMTQGLRXLGDXINAYYA; (SEQ ID NO: 4)

RPEIWMTQGLRRLGDEINAYYR; (SEQ ID NO: 5)

EIWMXQGLXRLGDEINAYYA; (SEQ ID NO: 20)

PEIWMTQGLRXLGDXINAYYA; (SEQ ID NO: 21)

PEIWMTQGLRRLGDEINAYYR; (SEQ ID NO: 22)

IWNleTQGLRRLGDEINAYYARR; (SEQ ID NO: 6)

IWNleTQGLRXLGDXINAYYARR; (SEQ ID NO: 7)

IWNleTQGLRRLGDEIXAYYXRR; (SEQ ID NO: 8)

IWNleXQGLXRLGDEINAYYARR; (SEQ ID NO: 9)

IWNleXQGLXRLGDEINAYYAR; (SEQ ID NO: 10)

EIWNleXQGLXRLGDEINAYYAR; (SEQ ID NO: 11)

EIWNleXQGLXRLGDEINAYYA; (SEQ ID NO: 12)

IWNleXQELXRLGDEINAYYARR; (SEQ ID NO: 13)

IWNleXQSLXRLGDEINAYYARR; (SEQ ID NO: 14)

-continued

IWNleXQSLXRLGDEINAYYAR; (SEQ ID NO: 15)

IWNleXQEDCRLGDEINAYYAR; (SEQ ID NO: 16)

IWNleXQGLXRLGDEINARYAR; (SEQ ID NO: 17)

IWNleXQEDCRLGDEINARYAR; (SEQ ID NO: 18)

IWNleXRGLXRLGDEINAYYAR; (SEQ ID NO: 19)

IWFAQEIDRIGDEVNAYYARR; (SEQ ID NO: 23)

IWFAQEIDXIGDXVNAYYARR; (SEQ ID NO: 24)

IWFAQEIDRIGDEVXAYYXRR; (SEQ ID NO: 25)

IWFXQEIXRIGDEVNAYYARR; (SEQ ID NO: 26)

IWFXQEIXRIGDEVNAYYAR; (SEQ ID NO: 27)

EIWFXQEIXRIGDEVNAYYAR; (SEQ ID NO: 28)

IWFAXEIDXIGDEVNAYYARR; and (SEQ ID NO: 29)

XWFAQEIXRIGDEVNAYYARR; (SEQ ID NO: 30)

and
wherein X represents an amino acid whose side chain has been replaced by an internal cross-link.

7. The compound of claim 1 the cross-link is a C8 alkylene or a C11 alkylene.

8. The compound of claim 1, wherein A3 is L, D3 is L, E3 is G, F3 is D, and A4 is I or V.

9. The compound of claim 8, wherein the amino acid sequence of the peptide comprises IWNleXQELXRLGDEINARYAR (SEQ ID NO:18), and wherein X represents an amino acid whose side chain has been replaced by an internal cross-link.

10. The compound of claim 1, wherein A3 is L, D3 is I, E3 is G, F3 is D, and A4 is I.

11. The compound of claim 1, wherein A3 is I, D3 is L, E3 is G, F3 is D, and A4 is I.

12. The compound of claim 1, wherein A3 is I, D3 is isoleucine, E3 is G, F3 is D, and A4 is I.

13. The compound of claim 1, wherein the amino acid sequence of the peptide comprises a sequence selected from the group consisting of:

IWFAQEIDRIGDEVNAYYAR. (SEQ ID NO: 31)

EIWFAQEIDRIGDEVNAYYAR, (SEQ ID NO: 32)

RPEIWLTQSLQRLGDEINAYYAR, (SEQ ID NO: 33)

RPEIWLTQHLQRLGDEINAYYAR, (SEQ ID NO: 34)

RPEIWITQELRRIGDEINAYYAR, (SEQ ID NO: 44)

IWMTQGLRRLGDEINAYYAR, (SEQ ID NO: 45)

RPEIWNleTQGLRRLGDEINAYYAR, and (SEQ ID NO: 53)

IWMTQGLRRLGDEINAYYARR. (SEQ ID NO: 54)

14. The compound of claim 1, wherein the amino acid sequence of the peptide comprises a sequence selected from the group consisting of:

IXNleTQXIRRLGDEINAYYARR, (SEQ ID NO: 46)

IWXTQGXRRLGDEINAYYARR, (SEQ ID NO: 47)

IWNleTQXLRRXGDEINAYYARR, (SEQ ID NO: 48)

IWNleTQGXRRLXDEINAYYARR, (SEQ ID NO: 49)

IWNleTQGLXRLGXEINAYYARR, (SEQ ID NO: 50)

IWNleTQGLRRLXDEIXAYYARR, and (SEQ ID NO: 51)

IWNleTQGLRRLGDXINAXYARR; (SEQ ID NO: 52)

and wherein X represents an amino acid side chain has been replaced by an internal cross-link.

15. A pharmaceutical composition comprising the compound of claim 1.

16. The compound of claim 6, wherein the amino acid sequence of the peptide comprises IWNleXQSLXRLGDEINAYYARR (SEQ ID NO:14), wherein X represents an amino acid whose side chain has been replaced by an internal cross-link.

* * * * *

SEQUENCE LISTING

```
<160> NUMBER OF SEQ ID NOS: 54

<210> SEQ ID NO 1
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide that binds human Mcl-1
<220> FEATURE:
<221> NAME/KEY: MOD_RES
<222> LOCATION: (1)..(1)
<223> OTHER INFORMATION: R or a conservative substitution or not present
<220> FEATURE:
<221> NAME/KEY: MOD_RES
<222> LOCATION: (2)..(2)
<223> OTHER INFORMATION: P or a conservative substitution or not present
<220> FEATURE:
<221> NAME/KEY: MOD_RES
<222> LOCATION: (3)..(3)
<223> OTHER INFORMATION: E or a conservative substitution or not present
<220> FEATURE:
<221> NAME/KEY: MOD_RES
<222> LOCATION: (4)..(4)
<223> OTHER INFORMATION: I or a conservative substitution
<220> FEATURE:
<221> NAME/KEY: MOD_RES
<222> LOCATION: (5)..(5)
<223> OTHER INFORMATION: W or a conservative substitution
<220> FEATURE:
<221> NAME/KEY: MOD_RES
<222> LOCATION: (6)..(6)
<223> OTHER INFORMATION: M or a conservative substitution, L or a
      conservative substitution, F or a conservative substitution or
      norleucine
<220> FEATURE:
```

```
<221> NAME/KEY: MOD_RES
<222> LOCATION: (7)..(7)
<223> OTHER INFORMATION: T or a conservative substitution, A or a
      conservative substitution, V or a conservative substitution, Aib
      or a conservative substitution
<220> FEATURE:
<221> NAME/KEY: MOD_RES
<222> LOCATION: (8)..(8)
<223> OTHER INFORMATION: Q or a conservative substitution, R or a
      conservative substitution
<220> FEATURE:
<221> NAME/KEY: MOD_RES
<222> LOCATION: (9)..(9)
<223> OTHER INFORMATION: G, H, E, S or a conservative substitution of
      one of G, H, E, and S
<220> FEATURE:
<221> NAME/KEY: MOD_RES
<222> LOCATION: (10)..(10)
<223> OTHER INFORMATION: L or a conservative substitution, I or a
      conservative substitution
<220> FEATURE:
<221> NAME/KEY: MOD_RES
<222> LOCATION: (11)..(11)
<223> OTHER INFORMATION: R or a conservative substitution, D or a
      conservative substitution, Q or a conservative substitution, Aib
      or a conservative substitution, Me-Leu or a conservative
      substitution
<220> FEATURE:
<221> NAME/KEY: MOD_RES
<222> LOCATION: (12)..(12)
<223> OTHER INFORMATION: R or a conservative substitution
<220> FEATURE:
<221> NAME/KEY: MOD_RES
<222> LOCATION: (13)..(13)
<223> OTHER INFORMATION: L or a conservative substitution, I or a
      conservative substitution
<220> FEATURE:
<221> NAME/KEY: MOD_RES
<222> LOCATION: (14)..(14)
<223> OTHER INFORMATION: G or a conservative substitution
<220> FEATURE:
<221> NAME/KEY: MOD_RES
<222> LOCATION: (15)..(15)
<223> OTHER INFORMATION: D or a conservative substitution
<220> FEATURE:
<221> NAME/KEY: MOD_RES
<222> LOCATION: (16)..(16)
<223> OTHER INFORMATION: E or a conservative substitution
<220> FEATURE:
<221> NAME/KEY: MOD_RES
<222> LOCATION: (17)..(17)
<223> OTHER INFORMATION: I or a conservative substitution, V or a
      conservative substitution
<220> FEATURE:
<221> NAME/KEY: MOD_RES
<222> LOCATION: (18)..(18)
<223> OTHER INFORMATION: N or a conservative substitution
<220> FEATURE:
<221> NAME/KEY: MOD_RES
<222> LOCATION: (19)..(19)
<223> OTHER INFORMATION: A or a conservative substitution
<220> FEATURE:
<221> NAME/KEY: MOD_RES
<222> LOCATION: (20)..(20)
<223> OTHER INFORMATION: Y or a conservative substitution
<220> FEATURE:
<221> NAME/KEY: MOD_RES
<222> LOCATION: (21)..(21)
<223> OTHER INFORMATION: Y or a conservative substitution
<220> FEATURE:
<221> NAME/KEY: MOD_RES
<222> LOCATION: (22)..(22)
<223> OTHER INFORMATION: A or a conservative substitution
<220> FEATURE:
<221> NAME/KEY: MOD_RES
<222> LOCATION: (23)..(23)
<223> OTHER INFORMATION: R or a conservative substitution or not present
<220> FEATURE:
<221> NAME/KEY: MOD_RES
```

```
<222> LOCATION: (24)..(24)
<223> OTHER INFORMATION: R or a conservative or not present
<220> FEATURE:
<223> OTHER INFORMATION: See specification as filed for detailed
      description of substitutions and preferred embodiments

<400> SEQUENCE: 1

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa
            20

<210> SEQ ID NO 2
<211> LENGTH: 23
<212> TYPE: PRT
<213> ORGANISM: Homo sapiens
<220> FEATURE:
<223> OTHER INFORMATION: See specification as filed for detailed
      description of substitutions and preferred embodiments

<400> SEQUENCE: 2

Arg Pro Glu Ile Trp Met Thr Gln Gly Leu Arg Arg Leu Gly Asp Glu
1               5                   10                  15

Ile Asn Ala Tyr Tyr Ala Arg
            20

<210> SEQ ID NO 3
<211> LENGTH: 22
<212> TYPE: PRT
<213> ORGANISM: Homo sapiens
<220> FEATURE:
<221> NAME/KEY: MOD_RES
<222> LOCATION: (7)..(7)
<223> OTHER INFORMATION: Any amino acid available for cross-linking
<220> FEATURE:
<221> NAME/KEY: MISC_FEATURE
<222> LOCATION: (7)..(11)
<223> OTHER INFORMATION: Cross-link between residues
<220> FEATURE:
<221> NAME/KEY: MOD_RES
<222> LOCATION: (11)..(11)
<223> OTHER INFORMATION: Any amino acid available for cross-linking

<400> SEQUENCE: 3

Arg Pro Glu Ile Trp Met Xaa Gln Gly Leu Xaa Arg Leu Gly Asp Glu
1               5                   10                  15

Ile Asn Ala Tyr Tyr Ala
            20

<210> SEQ ID NO 4
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide that binds human Mcl-1
<220> FEATURE:
<221> NAME/KEY: MOD_RES
<222> LOCATION: (12)..(12)
<223> OTHER INFORMATION: Any amino acid available for cross-linking
<220> FEATURE:
<221> NAME/KEY: MISC_FEATURE
<222> LOCATION: (12)..(16)
<223> OTHER INFORMATION: Cross-link between residues
<220> FEATURE:
<221> NAME/KEY: MOD_RES
<222> LOCATION: (16)..(16)
<223> OTHER INFORMATION: Any amino acid available for cross-linking

<400> SEQUENCE: 4
```

```
Arg Pro Glu Ile Trp Met Thr Gln Gly Leu Arg Xaa Leu Gly Asp Xaa
1               5                   10                  15

Ile Asn Ala Tyr Tyr Ala
            20

<210> SEQ ID NO 5
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide that binds human Mcl-1

<400> SEQUENCE: 5

Arg Pro Glu Ile Trp Met Thr Gln Gly Leu Arg Arg Leu Gly Asp Glu
1               5                   10                  15

Ile Asn Ala Tyr Tyr Arg
            20

<210> SEQ ID NO 6
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide that binds human Mcl-1
<220> FEATURE:
<221> NAME/KEY: MOD_RES
<222> LOCATION: (3)..(3)
<223> OTHER INFORMATION: Norleucine
<220> FEATURE:
<223> OTHER INFORMATION: See specification as filed for detailed
      description of substitutions and preferred embodiments

<400> SEQUENCE: 6

Ile Trp Xaa Thr Gln Gly Leu Arg Arg Leu Gly Asp Glu Ile Asn Ala
1               5                   10                  15

Tyr Tyr Ala Arg Arg
            20

<210> SEQ ID NO 7
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide that binds human Mcl-1
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (9)..(9)
<223> OTHER INFORMATION: Any amino acid available for cross-linking
<220> FEATURE:
<221> NAME/KEY: MISC_FEATURE
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Any amino acid available for cross-linking
<220> FEATURE:
<223> OTHER INFORMATION: See specification as filed for detailed
      description of substitutions and preferred embodiments

<400> SEQUENCE: 7

Ile Trp Xaa Thr Gln Gly Leu Arg Xaa Leu Gly Asp Xaa Ile Asn Ala
```

```
1               5                   10                  15

Tyr Tyr Ala Arg Arg
            20

<210> SEQ ID NO 8
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide that binds human Mcl-1
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (15)..(15)
<223> OTHER INFORMATION: Any amino acid available for cross-linking
<220> FEATURE:
<221> NAME/KEY: MISC_FEATURE
<222> LOCATION: (15)..(19)
<223> OTHER INFORMATION: Cross-link between residues
<220> FEATURE:
<221> NAME/KEY: MOD_RES
<222> LOCATION: (19)..(19)
<223> OTHER INFORMATION: Any amino acid available for cross-linking
<220> FEATURE:
<223> OTHER INFORMATION: See specification as filed for detailed
      description of substitutions and preferred embodiments

<400> SEQUENCE: 8

Ile Trp Xaa Thr Gln Gly Leu Arg Arg Leu Gly Asp Glu Ile Xaa Ala
1               5                   10                  15

Tyr Tyr Xaa Arg Arg
            20

<210> SEQ ID NO 9
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide that binds human Mcl-1
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (4)..(4)
<223> OTHER INFORMATION: Any amino acid available for cross-linking
<220> FEATURE:
<221> NAME/KEY: MISC_FEATURE
<222> LOCATION: (4)..(8)
<223> OTHER INFORMATION: Cross-link between residues
<220> FEATURE:
<221> NAME/KEY: MOD_RES
<222> LOCATION: (8)..(8)
<223> OTHER INFORMATION: Any amino acid available for cross-linking
<220> FEATURE:
<223> OTHER INFORMATION: See specification as filed for detailed
      description of substitutions and preferred embodiments

<400> SEQUENCE: 9

Ile Trp Xaa Xaa Gln Gly Leu Xaa Arg Leu Gly Asp Glu Ile Asn Ala
1               5                   10                  15

Tyr Tyr Ala Arg Arg
            20

<210> SEQ ID NO 10
```

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide that binds human Mcl-1
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (4)..(4)
<223> OTHER INFORMATION: Any amino acid available for cross-linking
<220> FEATURE:
<221> NAME/KEY: MISC_FEATURE
<222> LOCATION: (4)..(8)
<223> OTHER INFORMATION: Cross-link between residues
<220> FEATURE:
<221> NAME/KEY: MOD_RES
<222> LOCATION: (8)..(8)
<223> OTHER INFORMATION: Any amino acid available for cross-linking
<220> FEATURE:
<223> OTHER INFORMATION: See specification as filed for detailed
      description of substitutions and preferred embodiments

<400> SEQUENCE: 10

Ile Trp Xaa Xaa Gln Gly Leu Xaa Arg Leu Gly Asp Glu Ile Asn Ala
1               5                   10                  15

Tyr Tyr Ala Arg
            20

<210> SEQ ID NO 11
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide that binds human Mcl-1
<220> FEATURE:
<221> NAME/KEY: MOD_RES
<222> LOCATION: (4)..(4)
<223> OTHER INFORMATION: Norleucine
<220> FEATURE:
<221> NAME/KEY: MOD_RES
<222> LOCATION: (5)..(5)
<223> OTHER INFORMATION: Any amino acid available for cross-linking
<220> FEATURE:
<221> NAME/KEY: MISC_FEATURE
<222> LOCATION: (5)..(9)
<223> OTHER INFORMATION: Cross-link between residues
<220> FEATURE:
<221> NAME/KEY: MOD_RES
<222> LOCATION: (9)..(9)
<223> OTHER INFORMATION: Any amino acid available for cross-linking
<220> FEATURE:
<223> OTHER INFORMATION: See specification as filed for detailed
      description of substitutions and preferred embodiments

<400> SEQUENCE: 11

Glu Ile Trp Xaa Xaa Gln Gly Leu Xaa Arg Leu Gly Asp Glu Ile Asn
1               5                   10                  15

Ala Tyr Tyr Ala Arg
            20

<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide that binds human Mcl-1
<220> FEATURE:
```

```
<221> NAME/KEY: MOD_RES
<222> LOCATION: (4)..(4)
<223> OTHER INFORMATION: Norleucine
<220> FEATURE:
<221> NAME/KEY: MOD_RES
<222> LOCATION: (5)..(5)
<223> OTHER INFORMATION: Any amino acid available for cross-linking
<220> FEATURE:
<221> NAME/KEY: MISC_FEATURE
<222> LOCATION: (5)..(9)
<223> OTHER INFORMATION: Cross-link between residues
<220> FEATURE:
<221> NAME/KEY: MOD_RES
<222> LOCATION: (9)..(9)
<223> OTHER INFORMATION: Any amino acid available for cross-linking
<220> FEATURE:
<223> OTHER INFORMATION: See specification as filed for detailed
      description of substitutions and preferred embodiments

<400> SEQUENCE: 12

Glu Ile Trp Xaa Xaa Gln Gly Leu Xaa Arg Leu Gly Asp Glu Ile Asn
1               5                   10                  15

Ala Tyr Tyr Ala
            20

<210> SEQ ID NO 13
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide that binds human Mcl-1
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (4)..(4)
<223> OTHER INFORMATION: Any amino acid available for cross-linking
<220> FEATURE:
<221> NAME/KEY: MISC_FEATURE
<222> LOCATION: (4)..(8)
<223> OTHER INFORMATION: Cross-link between residues
<220> FEATURE:
<221> NAME/KEY: MOD_RES
<222> LOCATION: (8)..(8)
<223> OTHER INFORMATION: Any amino acid available for cross-linking
<220> FEATURE:
<223> OTHER INFORMATION: See specification as filed for detailed
      description of substitutions and preferred embodiments

<400> SEQUENCE: 13

Ile Trp Xaa Xaa Gln Glu Leu Xaa Arg Leu Gly Asp Glu Ile Asn Ala
1               5                   10                  15

Tyr Tyr Ala Arg Arg
            20

<210> SEQ ID NO 14
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide that binds human Mcl-1
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (4)..(4)
<223> OTHER INFORMATION: Any amino acid available for cross-linking
```

```
<220> FEATURE:
<221> NAME/KEY: MISC_FEATURE
<222> LOCATION: (4)..(8)
<223> OTHER INFORMATION: Cross-link between residues
<220> FEATURE:
<221> NAME/KEY: MOD_RES
<222> LOCATION: (8)..(8)
<223> OTHER INFORMATION: Any amino acid available for cross-linking
<220> FEATURE:
<223> OTHER INFORMATION: See specification as filed for detailed
      description of substitutions and preferred embodiments

<400> SEQUENCE: 14

Ile Trp Xaa Xaa Gln Ser Leu Xaa Arg Leu Gly Asp Glu Ile Asn Ala
1               5                   10                  15

Tyr Tyr Ala Arg Arg
            20

<210> SEQ ID NO 15
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide that binds human Mcl-1
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (4)..(4)
<223> OTHER INFORMATION: Any amino acid available for cross-linking
<220> FEATURE:
<221> NAME/KEY: MISC_FEATURE
<222> LOCATION: (4)..(8)
<223> OTHER INFORMATION: Cross-link between residues
<220> FEATURE:
<221> NAME/KEY: MOD_RES
<222> LOCATION: (8)..(8)
<223> OTHER INFORMATION: Any amino acid available for cross-linking
<220> FEATURE:
<223> OTHER INFORMATION: See specification as filed for detailed
      description of substitutions and preferred embodiments

<400> SEQUENCE: 15

Ile Trp Xaa Xaa Gln Ser Leu Xaa Arg Leu Gly Asp Glu Ile Asn Ala
1               5                   10                  15

Tyr Tyr Ala Arg
            20

<210> SEQ ID NO 16
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide that binds human Mcl-1
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (4)..(4)
<223> OTHER INFORMATION: Any amino acid available for cross-linking
<220> FEATURE:
<221> NAME/KEY: MISC_FEATURE
<222> LOCATION: (4)..(8)
<223> OTHER INFORMATION: Cross-link between residues
<220> FEATURE:
<221> NAME/KEY: MOD_RES
<222> LOCATION: (8)..(8)
```

```
<223> OTHER INFORMATION: Any amino acid available for cross-linking
<220> FEATURE:
<223> OTHER INFORMATION: See specification as filed for detailed
      description of substitutions and preferred embodiments

<400> SEQUENCE: 16

Ile Trp Xaa Xaa Gln Glu Leu Xaa Arg Leu Gly Asp Glu Ile Asn Ala
1               5                   10                  15

Tyr Tyr Ala Arg
            20

<210> SEQ ID NO 17
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide that binds human Mcl-1
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (4)..(4)
<223> OTHER INFORMATION: Any amino acid available for cross-linking
<220> FEATURE:
<221> NAME/KEY: MISC_FEATURE
<222> LOCATION: (4)..(8)
<223> OTHER INFORMATION: Cross-link between residues
<220> FEATURE:
<221> NAME/KEY: MOD_RES
<222> LOCATION: (8)..(8)
<223> OTHER INFORMATION: Any amino acid available for cross-linking
<220> FEATURE:
<223> OTHER INFORMATION: See specification as filed for detailed
      description of substitutions and preferred embodiments

<400> SEQUENCE: 17

Ile Trp Xaa Xaa Gln Gly Leu Xaa Arg Leu Gly Asp Glu Ile Asn Ala
1               5                   10                  15

Arg Tyr Ala Arg
            20

<210> SEQ ID NO 18
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide that binds human Mcl-1
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (4)..(4)
<223> OTHER INFORMATION: Any amino acid available for cross-linking
<220> FEATURE:
<221> NAME/KEY: MISC_FEATURE
<222> LOCATION: (4)..(8)
<223> OTHER INFORMATION: Cross-link between residues
<220> FEATURE:
<221> NAME/KEY: MOD_RES
<222> LOCATION: (8)..(8)
<223> OTHER INFORMATION: Any amino acid available for cross-linking
<220> FEATURE:
<223> OTHER INFORMATION: See specification as filed for detailed
      description of substitutions and preferred embodiments

<400> SEQUENCE: 18
```

```
Ile Trp Xaa Xaa Gln Glu Leu Xaa Arg Leu Gly Asp Glu Ile Asn Ala
1               5                   10                  15

Arg Tyr Ala Arg
            20

<210> SEQ ID NO 19
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide that binds human Mcl-1
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (4)..(4)
<223> OTHER INFORMATION: Any amino acid available for cross-linking
<220> FEATURE:
<221> NAME/KEY: MISC_FEATURE
<222> LOCATION: (4)..(8)
<223> OTHER INFORMATION: Cross-link between residues
<220> FEATURE:
<221> NAME/KEY: MOD_RES
<222> LOCATION: (8)..(8)
<223> OTHER INFORMATION: Any amino acid available for cross-linking
<220> FEATURE:
<223> OTHER INFORMATION: See specification as filed for detailed
      description of substitutions and preferred embodiments

<400> SEQUENCE: 19

Ile Trp Xaa Xaa Arg Gly Leu Xaa Arg Leu Gly Asp Glu Ile Asn Ala
1               5                   10                  15

Tyr Tyr Ala Arg
            20

<210> SEQ ID NO 20
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide that binds human Mcl-1
<220> FEATURE:
<221> NAME/KEY: MOD_RES
<222> LOCATION: (5)..(5)
<223> OTHER INFORMATION: Any amino acid available for cross-linking
<220> FEATURE:
<221> NAME/KEY: MISC_FEATURE
<222> LOCATION: (5)..(9)
<223> OTHER INFORMATION: Cross-link between residues
<220> FEATURE:
<221> NAME/KEY: MOD_RES
<222> LOCATION: (9)..(9)
<223> OTHER INFORMATION: Any amino acid available for cross-linking

<400> SEQUENCE: 20

Glu Ile Trp Met Xaa Gln Gly Leu Xaa Arg Leu Gly Asp Glu Ile Asn
1               5                   10                  15

Ala Tyr Tyr Ala
            20

<210> SEQ ID NO 21
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide that binds human Mcl-1
```

```
<220> FEATURE:
<221> NAME/KEY: MOD_RES
<222> LOCATION: (11)..(11)
<223> OTHER INFORMATION: Any amino acid available for cross-linking
<220> FEATURE:
<221> NAME/KEY: MISC_FEATURE
<222> LOCATION: (11)..(15)
<223> OTHER INFORMATION: Cross-link between residues
<220> FEATURE:
<221> NAME/KEY: MOD_RES
<222> LOCATION: (15)..(15)
<223> OTHER INFORMATION: Any amino acid available for cross-linking

<400> SEQUENCE: 21

Pro Glu Ile Trp Met Thr Gln Gly Leu Arg Xaa Leu Gly Asp Xaa Ile
1               5                   10                  15

Asn Ala Tyr Tyr Ala
            20

<210> SEQ ID NO 22
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide that binds human Mcl-1

<400> SEQUENCE: 22

Pro Glu Ile Trp Met Thr Gln Gly Leu Arg Arg Leu Gly Asp Glu Ile
1               5                   10                  15

Asn Ala Tyr Tyr Arg
            20

<210> SEQ ID NO 23
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide that binds human Mcl-1
<220> FEATURE:
<223> OTHER INFORMATION: See specification as filed for detailed
      description of substitutions and preferred embodiments

<400> SEQUENCE: 23

Ile Trp Phe Ala Gln Glu Ile Asp Arg Ile Gly Asp Glu Val Asn Ala
1               5                   10                  15

Tyr Tyr Ala Arg Arg
            20

<210> SEQ ID NO 24
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide that binds human Mcl-1
<220> FEATURE:
<221> NAME/KEY: MOD_RES
<222> LOCATION: (9)..(9)
<223> OTHER INFORMATION: Any amino acid available for cross-linking
<220> FEATURE:
<221> NAME/KEY: MISC_FEATURE
<222> LOCATION: (9)..(13)
<223> OTHER INFORMATION: Cross-link between residues
<220> FEATURE:
<221> NAME/KEY: MOD_RES
<222> LOCATION: (13)..(13)
<223> OTHER INFORMATION: Any amino acid available for cross-linking
<220> FEATURE:
```

```
<223> OTHER INFORMATION: See specification as filed for detailed
      description of substitutions and preferred embodiments

<400> SEQUENCE: 24

Ile Trp Phe Ala Gln Glu Ile Asp Xaa Ile Gly Asp Xaa Val Asn Ala
1               5                   10                  15

Tyr Tyr Ala Arg Arg
            20

<210> SEQ ID NO 25
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide that binds human Mcl-1
<220> FEATURE:
<221> NAME/KEY: MOD_RES
<222> LOCATION: (15)..(15)
<223> OTHER INFORMATION: Any amino acid available for cross-linking
<220> FEATURE:
<221> NAME/KEY: MISC_FEATURE
<222> LOCATION: (15)..(19)
<223> OTHER INFORMATION: Cross-link between residues
<220> FEATURE:
<221> NAME/KEY: MOD_RES
<222> LOCATION: (19)..(19)
<223> OTHER INFORMATION: Any amino acid available for cross-linking
<220> FEATURE:
<223> OTHER INFORMATION: See specification as filed for detailed
      description of substitutions and preferred embodiments

<400> SEQUENCE: 25

Ile Trp Phe Ala Gln Glu Ile Asp Arg Ile Gly Asp Glu Val Xaa Ala
1               5                   10                  15

Tyr Tyr Xaa Arg Arg
            20

<210> SEQ ID NO 26
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide that binds human Mcl-1
<220> FEATURE:
<221> NAME/KEY: MOD_RES
<222> LOCATION: (4)..(4)
<223> OTHER INFORMATION: Any amino acid available for cross-linking
<220> FEATURE:
<221> NAME/KEY: MISC_FEATURE
<222> LOCATION: (4)..(8)
<223> OTHER INFORMATION: Cross-link between residues
<220> FEATURE:
<221> NAME/KEY: MOD_RES
<222> LOCATION: (8)..(8)
<223> OTHER INFORMATION: Any amino acid available for cross-linking
<220> FEATURE:
<223> OTHER INFORMATION: See specification as filed for detailed
      description of substitutions and preferred embodiments

<400> SEQUENCE: 26

Ile Trp Phe Xaa Gln Glu Ile Xaa Arg Ile Gly Asp Glu Val Asn Ala
1               5                   10                  15

Tyr Tyr Ala Arg Arg
            20

<210> SEQ ID NO 27
<211> LENGTH: 20
<212> TYPE: PRT
```

```
<213> ORGANISM: Artificial Sequence
<220> FEATURE:
<223> OTHER INFORMATION: Description of Artificial Sequence: Synthetic
      peptide that binds human Mcl-1
<220> FEATURE:
<221> NAME/KEY: MOD_RES
<222> LOCATION: (4)..(4)
<223> OTHER INFORMATION: Any amino acid available for cross-linking
<220> FEATURE:
<221> NAME/KEY: MISC_FEATURE
<222> LOCATION: (4)..(8)
<223> OTHER INFORMATION: Cross-link between residues
<220> FEATURE:
<221> NAME/KEY: MOD_RES
<222> LOCATION: (8)..(8)
<223> OTHER INFORMATION: Any amino acid available for cross-linking
<220> FEATURE:
<223> OTHER INFORMATION: See specification as filed for detailed
      description of substitutions and preferred embodiments

<400> SEQUENCE: 27

Ile Trp Phe Xaa Gln Glu Ile Xaa Arg Ile Gly Asp Glu Val Asn Ala
1               5                   10                  15

Tyr Tyr Ala Arg
            20

<210> SEQ ID NO 28
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide that binds human Mcl-1
<220> FEATURE:
<221> NAME/KEY: MOD_RES
<222> LOCATION: (5)..(5)
<223> OTHER INFORMATION: Any amino acid available for cross-linking
<220> FEATURE:
<221> NAME/KEY: MISC_FEATURE
<222> LOCATION: (5)..(9)
<223> OTHER INFORMATION: Cross-link between residues
<220> FEATURE:
<221> NAME/KEY: MOD_RES
<222> LOCATION: (9)..(9)
<223> OTHER INFORMATION: Any amino acid available for cross-linking
<220> FEATURE:
<223> OTHER INFORMATION: See specification as filed for detailed
      description of substitutions and preferred embodiments

<400> SEQUENCE: 28

Glu Ile Trp Phe Xaa Gln Glu Ile Xaa Arg Ile Gly Asp Glu Val Asn
1               5                   10                  15

Ala Tyr Tyr Ala Arg
            20

<210> SEQ ID NO 29
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide that binds human Mcl-1
<220> FEATURE:
<221> NAME/KEY: MOD_RES
<222> LOCATION: (5)..(5)
<223> OTHER INFORMATION: Any amino acid available for cross-linking
<220> FEATURE:
<221> NAME/KEY: MISC_FEATURE
<222> LOCATION: (5)..(9)
<223> OTHER INFORMATION: Cross-link between residues
<220> FEATURE:
<221> NAME/KEY: MOD_RES
<222> LOCATION: (9)..(9)
```

```
<223> OTHER INFORMATION: Any amino acid available for cross-linking
<220> FEATURE:
<223> OTHER INFORMATION: See specification as filed for detailed
      description of substitutions and preferred embodiments

<400> SEQUENCE: 29

Ile Trp Phe Ala Xaa Glu Ile Asp Xaa Ile Gly Asp Glu Val Asn Ala
1               5                   10                  15

Tyr Tyr Ala Arg Arg
            20

<210> SEQ ID NO 30
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide that binds human Mcl-1
<220> FEATURE:
<221> NAME/KEY: MOD_RES
<222> LOCATION: (1)..(1)
<223> OTHER INFORMATION: Any amino acid available for cross-linking
<220> FEATURE:
<221> NAME/KEY: MISC_FEATURE
<222> LOCATION: (1)..(8)
<223> OTHER INFORMATION: Cross-link between residues
<220> FEATURE:
<221> NAME/KEY: MOD_RES
<222> LOCATION: (8)..(8)
<223> OTHER INFORMATION: Any amino acid available for cross-linking
<220> FEATURE:
<223> OTHER INFORMATION: See specification as filed for detailed
      description of substitutions and preferred embodiments

<400> SEQUENCE: 30

Xaa Trp Phe Ala Gln Glu Ile Xaa Arg Ile Gly Asp Glu Val Asn Ala
1               5                   10                  15

Tyr Tyr Ala Arg Arg
            20

<210> SEQ ID NO 31
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide that binds human Mcl-1

<400> SEQUENCE: 31

Ile Trp Phe Ala Gln Glu Ile Asp Arg Ile Gly Asp Glu Val Asn Ala
1               5                   10                  15

Tyr Tyr Ala Arg
            20

<210> SEQ ID NO 32
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide that binds human Mcl-1

<400> SEQUENCE: 32

Glu Ile Trp Phe Ala Gln Glu Ile Asp Arg Ile Gly Asp Glu Val Asn
1               5                   10                  15

Ala Tyr Tyr Ala Arg
            20
```

<210> SEQ ID NO 33
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide that binds human Mcl-1

<400> SEQUENCE: 33

Arg Pro Glu Ile Trp Leu Thr Gln Ser Leu Gln Arg Leu Gly Asp Glu
1               5                   10                  15

Ile Asn Ala Tyr Tyr Ala Arg
            20

<210> SEQ ID NO 34
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide that binds human Mcl-1

<400> SEQUENCE: 34

Arg Pro Glu Ile Trp Leu Thr Gln His Leu Gln Arg Leu Gly Asp Glu
1               5                   10                  15

Ile Asn Ala Tyr Tyr Ala Arg
            20

<210> SEQ ID NO 35
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide that binds human Mcl-1

<400> SEQUENCE: 35

Arg Pro Glu Ile Trp Met Gly Gln Gly Leu Arg Arg Leu Gly Asp Glu
1               5                   10                  15

Ile Asn Ala Tyr Tyr Ala Arg
            20

<210> SEQ ID NO 36
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide that binds human Mcl-1

<400> SEQUENCE: 36

Arg Pro Glu Ile Trp Leu Gly Gln Ser Leu Gln Arg Leu Gly Asp Glu
1               5                   10                  15

Ile Asn Ala Tyr Tyr Ala Arg
            20

<210> SEQ ID NO 37
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide that binds human Mcl-1

<400> SEQUENCE: 37

Arg Pro Glu Ile Trp Leu Gly Gln His Leu Gln Arg Leu Gly Asp Glu
1               5                   10                  15

Ile Asn Ala Tyr Tyr Ala Arg
            20

<210> SEQ ID NO 38
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide that binds human Mcl-1

<400> SEQUENCE: 38

Ala Glu Leu Pro Pro Glu Phe Ala Ala Gln Leu Arg Lys Ile Gly Asp
1               5                   10                  15

Lys Val Tyr Cys
            20

<210> SEQ ID NO 39
<211> LENGTH: 23
<212> TYPE: PRT
<213> ORGANISM: Homo sapiens

<400> SEQUENCE: 39

Arg Pro Glu Ile Trp Ile Ala Gln Glu Leu Arg Arg Ile Gly Asp Glu
1               5                   10                  15

Phe Asn Ala Tyr Tyr Ala Arg
            20

<210> SEQ ID NO 40
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide that binds human Mcl-1

<400> SEQUENCE: 40

Arg Pro Glu Ile Trp Ile Thr Gln Glu Leu Arg Arg Ile Gly Asp Glu
1               5                   10                  15

Phe Asn Ala Tyr Tyr Ala Arg
            20

<210> SEQ ID NO 41
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide that binds human Mcl-1

<400> SEQUENCE: 41

Arg Pro Glu Ile Trp Met Thr Gln Glu Leu Arg Arg Ile Gly Asp Glu
1               5                   10                  15

Phe Asn Ala Tyr Tyr Ala Arg
            20

<210> SEQ ID NO 42
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide that binds human Mcl-1

<400> SEQUENCE: 42

Arg Pro Glu Ile Trp Ile Thr Gln Gly Leu Arg Arg Ile Gly Asp Glu
1               5                   10                  15

Phe Asn Ala Tyr Tyr Ala Arg
            20

<210> SEQ ID NO 43
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide that binds human Mcl-1

<400> SEQUENCE: 43

Arg Pro Glu Ile Trp Ile Thr Gln Glu Leu Arg Arg Leu Gly Asp Glu
1               5                   10                  15

Phe Asn Ala Tyr Tyr Ala Arg
            20

<210> SEQ ID NO 44
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide that binds human Mcl-1

<400> SEQUENCE: 44

Arg Pro Glu Ile Trp Ile Thr Gln Glu Leu Arg Arg Ile Gly Asp Glu
1               5                   10                  15

Ile Asn Ala Tyr Tyr Ala Arg
            20

<210> SEQ ID NO 45
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide that binds human Mcl-1

<400> SEQUENCE: 45

Ile Trp Met Thr Gln Gly Leu Arg Arg Leu Gly Asp Glu Ile Asn Ala
1               5                   10                  15

Tyr Tyr Ala Arg
            20

<210> SEQ ID NO 46
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide that binds human Mcl-1
<220> FEATURE:
<221> NAME/KEY: MOD_RES
<222> LOCATION: (2)..(2)
<223> OTHER INFORMATION: Any amino acid available for cross-linking
<220> FEATURE:
<221> NAME/KEY: MISC_FEATURE
<222> LOCATION: (2)..(6)
<223> OTHER INFORMATION: Cross-link between residues
<220> FEATURE:
<221> NAME/KEY: MOD_RES
<222> LOCATION: (3)..(3)

<223> OTHER INFORMATION: Norleucine
<220> FEATURE:
<221> NAME/KEY: MOD_RES
<222> LOCATION: (6)..(6)
<223> OTHER INFORMATION: Any amino acid available for cross-linking

<400> SEQUENCE: 46

Ile Xaa Xaa Thr Gln Xaa Ile Arg Arg Leu Gly Asp Glu Ile Asn Ala
1               5                   10                  15

Tyr Tyr Ala Arg Arg
            20

<210> SEQ ID NO 47
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide that binds human Mcl-1
<220> FEATURE:
<221> NAME/KEY: MOD_RES
<222> LOCATION: (3)..(3)
<223> OTHER INFORMATION: Any amino acid available for cross-linking
<220> FEATURE:
<221> NAME/KEY: MISC_FEATURE
<222> LOCATION: (3)..(7)
<223> OTHER INFORMATION: Cross-link between residues
<220> FEATURE:
<221> NAME/KEY: MOD_RES
<222> LOCATION: (7)..(7)
<223> OTHER INFORMATION: Any amino acid available for cross-linking

<400> SEQUENCE: 47

Ile Trp Xaa Thr Gln Gly Xaa Arg Arg Leu Gly Asp Glu Ile Asn Ala
1               5                   10                  15

Tyr Tyr Ala Arg Arg
            20

<210> SEQ ID NO 48
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide that binds human Mcl-1
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (6)..(6)
<223> OTHER INFORMATION: Any amino acid available for cross-linking
<220> FEATURE:
<221> NAME/KEY: MISC_FEATURE
<222> LOCATION: (6)..(10)
<223> OTHER INFORMATION: Cross-link between residues
<220> FEATURE:
<221> NAME/KEY: MOD_RES
<222> LOCATION: (10)..(10)
<223> OTHER INFORMATION: Any amino acid available for cross-linking

<400> SEQUENCE: 48

Ile Trp Xaa Thr Gln Xaa Leu Arg Arg Xaa Gly Asp Glu Ile Asn Ala
1               5                   10                  15

Tyr Tyr Ala Arg Arg
            20

<210> SEQ ID NO 49
<211> LENGTH: 21

```
<212> TYPE: PRT
<213> ORGANISM: Artificial Sequence
<220> FEATURE:
<223> OTHER INFORMATION: Description of Artificial Sequence: Synthetic
      peptide that binds human Mcl-1
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (7)..(7)
<223> OTHER INFORMATION: Any amino acid available for cross-linking
<220> FEATURE:
<221> NAME/KEY: MISC_FEATURE
<222> LOCATION: (7)..(11)
<223> OTHER INFORMATION: Cross-link between residues
<220> FEATURE:
<221> NAME/KEY: MOD_RES
<222> LOCATION: (11)..(11)
<223> OTHER INFORMATION: Any amino acid available for cross-linking

<400> SEQUENCE: 49

Ile Trp Xaa Thr Gln Gly Xaa Arg Arg Leu Xaa Asp Glu Ile Asn Ala
1               5                   10                  15

Tyr Tyr Ala Arg Arg
            20

<210> SEQ ID NO 50
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide that binds human Mcl-1
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (8)..(8)
<223> OTHER INFORMATION: Any amino acid available for cross-linking
<220> FEATURE:
<221> NAME/KEY: MISC_FEATURE
<222> LOCATION: (8)..(12)
<223> OTHER INFORMATION: Cross-link between residues
<220> FEATURE:
<221> NAME/KEY: MOD_RES
<222> LOCATION: (12)..(12)
<223> OTHER INFORMATION: Any amino acid available for cross-linking

<400> SEQUENCE: 50

Ile Trp Xaa Thr Gln Gly Leu Xaa Arg Leu Gly Xaa Glu Ile Asn Ala
1               5                   10                  15

Tyr Tyr Ala Arg Arg
            20

<210> SEQ ID NO 51
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide that binds human Mcl-1
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (11)..(11)
<223> OTHER INFORMATION: Any amino acid available for cross-linking
```

```
<220> FEATURE:
<221> NAME/KEY: MISC_FEATURE
<222> LOCATION: (11)..(15)
<223> OTHER INFORMATION: Cross-link between residues
<220> FEATURE:
<221> NAME/KEY: MOD_RES
<222> LOCATION: (15)..(15)
<223> OTHER INFORMATION: Any amino acid available for cross-linking

<400> SEQUENCE: 51

Ile Trp Xaa Thr Gln Gly Leu Arg Arg Leu Xaa Asp Glu Ile Xaa Ala
1               5                   10                  15

Tyr Tyr Ala Arg Arg
            20

<210> SEQ ID NO 52
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide that binds human Mcl-1
<220> FEATURE:
<221> NAME/KEY: MOD_RES
<222> LOCATION: (3)..(3)
<223> OTHER INFORMATION: Norleucine
<220> FEATURE:
<221> NAME/KEY: MOD_RES
<222> LOCATION: (13)..(13)
<223> OTHER INFORMATION: Any amino acid available for cross-linking
<220> FEATURE:
<221> NAME/KEY: MISC_FEATURE
<222> LOCATION: (13)..(17)
<223> OTHER INFORMATION: Cross-link between residues
<220> FEATURE:
<221> NAME/KEY: MOD_RES
<222> LOCATION: (17)..(17)
<223> OTHER INFORMATION: Any amino acid available for cross-linking

<400> SEQUENCE: 52

Ile Trp Xaa Thr Gln Gly Leu Arg Arg Leu Gly Asp Xaa Ile Asn Ala
1               5                   10                  15

Xaa Tyr Ala Arg Arg
            20

<210> SEQ ID NO 53
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide that binds human Mcl-1
<220> FEATURE:
<221> NAME/KEY: MOD_RES
<222> LOCATION: (6)..(6)
<223> OTHER INFORMATION: Norleucine

<400> SEQUENCE: 53

Arg Pro Glu Ile Trp Xaa Thr Gln Gly Leu Arg Arg Leu Gly Asp Glu
1               5                   10                  15

Ile Asn Ala Tyr Tyr Ala Arg
            20

<210> SEQ ID NO 54
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide that binds human Mcl-1
```

<400> SEQUENCE: 54

Ile Trp Met Thr Gln Gly Leu Arg Arg Leu Gly Asp Glu Ile Asn Ala
1               5                   10                  15

Tyr Tyr Ala Arg Arg
            20